(12) United States Patent
Gaugler et al.

(10) Patent No.: US 10,258,027 B2
(45) Date of Patent: Apr. 16, 2019

(54) AUTODISSEMINATION OF AN INSECT-GROWTH REGULATOR FOR INSECT MANAGEMENT

(71) Applicant: Rutgers, The State University of New Jersey, New Brunswick, NJ (US)

(72) Inventors: Randy Gaugler, North Brunswick, NJ (US); Devi Suman, New Brunswick, NJ (US); Yi Wang, South River, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/050,439

(22) Filed: Feb. 22, 2016

(65) Prior Publication Data
US 2016/0242403 A1 Aug. 25, 2016

Related U.S. Application Data

(63) Continuation-in-part of application No. 13/863,359, filed on Apr. 15, 2013, now Pat. No. 9,265,247, (Continued)

(51) Int. Cl.
*A01M 1/20* (2006.01)
*A01M 1/02* (2006.01)
(Continued)

(52) U.S. Cl.
CPC ............ *A01M 1/2005* (2013.01); *A01M 1/02* (2013.01); *A01M 1/20* (2013.01); *A01M 1/2011* (2013.01);
(Continued)

(58) Field of Classification Search
CPC ............ A01M 1/00; A01M 1/02; A01M 1/10; A01M 1/06; A01M 1/20; A01M 1/2005; A01M 1/2016
(Continued)

(56) References Cited

U.S. PATENT DOCUMENTS 1,018,277 A * 2/1912 Suhre .............................. 43/121
1,882,380 A * 10/1932 Braun ..................... A01M 1/02
43/107
(Continued)

FOREIGN PATENT DOCUMENTS

ES 2076893 A1 * 11/1995
JP 10146145 A * 6/1998
(Continued)

OTHER PUBLICATIONS

Yu et al., Autodissemination of a beet armyworm (*Lepidoptera: Noctuidae*) baculovirus under laboratory conditions, Journal of Economic Entomology, 1997, 1187-1194, 90.
(Continued)

*Primary Examiner* — Darren W Ark
(74) *Attorney, Agent, or Firm* — Kathleen D. Rigaut; Howson & HowsonLLP

(57) ABSTRACT

The described invention provides a gel formulation of a composition comprising at least one insecticide in an amount effective to control an insect larval population, an apparatus for autodissmenination of an insecticide for insect management containing (1) a reservoir (2) a transfer plate and cover, and (3) a mesh component, a method and a system for autodissemination for effectively controlling an insect larval population. Also disclosed is an improvised biphasic autodissemination station for control of undesirable insect populations.

19 Claims, 26 Drawing Sheets
(8 of 26 Drawing Sheet(s) Filed in Color)

Related U.S. Application Data which is a continuation-in-part of application No. PCT/US2011/056106, filed on Oct. 13, 2011.

(60) Provisional application No. 61/490,449, filed on May 26, 2011, provisional application No. 61/393,681, filed on Oct. 15, 2010.

(51) Int. Cl.
*A01N 25/04* (2006.01)
*A01N 25/00* (2006.01)
*A01N 25/24* (2006.01)

(52) U.S. Cl.
CPC ........... *A01M 1/2016* (2013.01); *A01N 25/00* (2013.01); *A01N 25/04* (2013.01); *A01N 25/24* (2013.01); *A01M 2200/011* (2013.01); *A01M 2200/012* (2013.01)

(58) Field of Classification Search
USPC ............................. 43/132.1, 131, 107, 121
See application file for complete search history.

(56) References Cited

U.S. PATENT DOCUMENTS

| | | | | |
|---|---|---|---|---|
| 2,167,978 A | * | 8/1939 | Jennerich | A01M 1/2005 43/121 |
| 2,606,391 A | * | 8/1952 | McGrew | A01M 1/02 43/121 |
| 3,303,599 A | * | 2/1967 | Ballard | A01M 1/106 43/131 |
| 3,851,417 A | * | 12/1974 | Wunsche | A01M 1/02 43/121 |
| 3,997,999 A | * | 12/1976 | Evans | A01M 1/02 43/107 |
| 4,030,233 A | * | 6/1977 | Wunsche | A01M 1/02 43/121 |
| 4,035,946 A | * | 7/1977 | Rapp | A01M 25/004 43/131 |
| 4,156,321 A | * | 5/1979 | Capizzi | A01M 1/02 43/114 |
| 4,218,843 A | * | 8/1980 | Clarke, Jr. | A01M 1/2055 43/131 |
| 4,263,740 A | * | 4/1981 | Hemsarth | A01M 1/02 43/121 |
| 4,316,344 A | * | 2/1982 | Carlsen | A01M 1/14 43/121 |
| 4,328,636 A | * | 5/1982 | Johnson | A01K 39/0106 43/107 |
| 4,395,842 A | * | 8/1983 | Margulies | A01M 1/02 43/121 |
| 4,485,582 A | | 12/1984 | Morris et al. | |
| 4,608,774 A | * | 9/1986 | Sherman | A01M 1/02 43/121 |
| 4,631,857 A | * | 12/1986 | Kase | A01M 1/20 43/131 |
| 4,671,010 A | | 6/1987 | Conlee et al. | |
| 4,690,775 A | | 9/1987 | Schott et al. | |
| 4,701,326 A | * | 10/1987 | Nelsen | A01N 63/00 119/6.7 |
| 4,751,082 A | * | 6/1988 | Schaerffenberg | A01N 63/04 424/93.5 |
| 4,753,799 A | * | 6/1988 | Nelsen | A01N 63/00 119/6.7 |
| 4,925,663 A | * | 5/1990 | Stimac | A01N 63/04 424/93.5 |
| 4,970,822 A | * | 11/1990 | Sherman | A01M 1/2011 431/31 |
| 5,042,194 A | * | 8/1991 | Cohen | A01M 1/2011 43/131 |
| 5,057,315 A | * | 10/1991 | Gunner | A01M 1/2011 43/132.1 |
| 5,057,316 A | * | 10/1991 | Gunner | A01M 1/2011 43/132.1 |
| 5,123,201 A | * | 6/1992 | Reiter | A01M 1/026 43/121 |
| 5,141,744 A | * | 8/1992 | Chang | A01N 25/006 424/409 |
| 5,182,879 A | * | 2/1993 | Hopkins | A01M 1/04 43/131 |
| 5,189,831 A | * | 3/1993 | Miller | A01M 1/2011 43/132.1 |
| 5,238,681 A | * | 8/1993 | Chang | A01N 25/006 43/131 |
| 5,310,552 A | * | 5/1994 | Gunner | A01M 1/2011 43/131 |
| 5,359,807 A | * | 11/1994 | Jackson | A01M 1/2016 43/131 |
| 5,406,741 A | * | 4/1995 | Little | A01M 23/08 43/64 |
| 5,413,784 A | * | 5/1995 | Wright | A01N 25/006 424/84 |
| 5,427,784 A | * | 6/1995 | Gunner | A01M 1/2011 43/131 |
| 5,452,540 A | * | 9/1995 | Dowd | A01M 1/02 43/107 |
| 5,516,513 A | * | 5/1996 | Wright | A01N 63/04 424/405 |
| 5,824,328 A | | 10/1998 | Levy | |
| 5,896,697 A | * | 4/1999 | Kang | A01M 1/02 43/107 |
| 5,983,557 A | * | 11/1999 | Perich | A01M 1/04 43/131 |
| 5,983,558 A | * | 11/1999 | Las | A01M 1/2005 43/131 |
| 6,041,543 A | * | 3/2000 | Howse | A01M 1/02 43/132.1 |
| 6,185,861 B1 | * | 2/2001 | Perich | A01M 1/04 43/131 |
| 6,301,827 B1 | * | 10/2001 | Lankster | A01M 1/02 43/107 |
| 6,327,810 B1 | * | 12/2001 | Howse | A01M 1/02 43/121 |
| 6,346,262 B1 | * | 2/2002 | Levy | A01N 25/10 43/131 |
| 6,389,740 B2 | * | 5/2002 | Perich | A01M 1/04 43/131 |
| 6,391,328 B1 | | 5/2002 | Levy | |
| 6,708,443 B2 | * | 3/2004 | Hall | A01M 1/02 43/132.1 |
| 6,886,293 B2 | * | 5/2005 | Forehand | A01M 1/106 43/107 |
| 7,073,287 B2 | * | 7/2006 | Lau | A01M 1/02 43/107 |
| 7,134,238 B2 | * | 11/2006 | Forehand | A01M 1/106 43/107 |
| 7,434,351 B2 | * | 10/2008 | Bette | A01M 1/106 43/131 |
| 7,669,362 B2 | * | 3/2010 | Cwiklinski | A01M 1/02 43/107 |
| 7,694,455 B1 | * | 4/2010 | Bowden | A01M 1/106 43/132.1 |
| 7,946,077 B2 | * | 5/2011 | Fukuhara | A01M 1/106 43/132.1 |
| 8,109,035 B2 | * | 2/2012 | Bowden | A01M 1/106 43/132.1 |
| 8,181,384 B2 | * | 5/2012 | Lebost | A01M 1/02 43/107 |
| 8,844,465 B2 | * | 9/2014 | Holland | A01M 1/106 119/6.5 |
| 9,192,151 B2 | * | 11/2015 | Koehler | A01M 1/2005 |
| 9,237,741 B2 | * | 1/2016 | Barrera | A01M 1/026 |
| 9,265,247 B2 | * | 2/2016 | Gaugler | A01N 25/00 |
| 9,295,246 B2 | * | 3/2016 | Koehler | A01M 1/20 |
| 9,532,560 B2 | * | 1/2017 | Osinga | A01M 1/2016 |
| 9,554,567 B2 | * | 1/2017 | Koehler | A01M 1/2005 |
| 2006/0191189 A1 | | 8/2006 | Mayo et al. | |
| 2007/0081969 A1 | | 4/2007 | McGee et al. | |

(56) References Cited

U.S. PATENT DOCUMENTS

| | | | | |
|---|---|---|---|---|
| 2010/0031556 A1* | 2/2010 | Kupfer | | A01M 1/2011 43/131 |
| 2010/0139151 A1* | 6/2010 | Cwiklinski | | A01M 1/02 43/107 |
| 2011/0038839 A1* | 2/2011 | Jackson | | A01G 1/04 424/93.5 |
| 2012/0110892 A1* | 5/2012 | Lloyd | | A01M 1/106 43/107 |
| 2015/0121746 A1* | 5/2015 | Osinga | | A01M 1/2016 43/132.1 |
| 2016/0128313 A1* | 5/2016 | Barrera | | A01M 1/026 43/107 |
| 2017/0000101 A1* | 1/2017 | Gaugler | | A01M 1/165 |
| 2017/0105402 A1* | 4/2017 | Koehler | | A01M 1/20 |

FOREIGN PATENT DOCUMENTS

| | | | | |
|---|---|---|---|---|
| JP | 2005087199 A | * | 4/2005 | |
| JP | 2006223276 A | * | 8/2006 | |
| JP | 2007236359 A | * | 9/2007 | |
| JP | WO 2008035545 A1 | * | 3/2008 | A01M 1/106 |
| JP | WO 2010041342 A1 | * | 4/2010 | A01M 1/106 |
| JP | WO 2012026047 A1 | * | 3/2012 | A01M 1/106 |
| KR | 20120005614 A | * | 1/2012 | |
| WO | WO 2006046067 A1 | * | 5/2006 | A01M 1/2005 |
| WO | WO 2007073591 A2 | * | 7/2007 | A01M 1/02 |

OTHER PUBLICATIONS

Klein et al., An attractant trap for autodissemination of entomopathogenic fungi into populations of the Japanese beetle *Popillia japonica* (Coleoptera: Scarabaeidae), Biocontrol Science and Technology, 1999, 151-158, 9.

Lacey et al., Factors influencing parasitism of adult Japanese beetles by entomopathogenic nematodes. Entomophaga, 1993, 501-9, 38.

Dowd et al., Autodissemination of Beauveria bassiana by sap beetles (*Coleoptera: Nitidulidae*) to overwintering sites. Biocontrol Science and Technology, 2003, 65-75, 13.

Ponnusamy et al., Diversity of bacterial communities in container habitats of mosquitoes, Microb Ecol. 2008, 593-603, 56(4).

Vezzani et al., The effect of shade on the container index and pupal productivity of the mosquitoes *Aedes aegypti* and *Culex pipiens* breeding in artificial containers, Medical and Veterinary Enzymology, 2009, 78-84, 23.

Ponnusamy et al., Oviposition responses of the mosquitoes *Aedes aegypti* and *Aedes albopictus* to experimental plant infusions in laboratory bioassays, Journal of Chemical Ecology, 2010, 709-719, 36.

Trexler et al., Laboratory and field evaluations of oviposition responses of Aedes albopictus and Aedes triseriatus (Diptera: Culicidae) to oak leaf infusions, Journal of Medical Entomology, 1998, 967-976, 35.

Itoh et al., Utilization of bloodfed females of Aedes aegypti as a vehicle for the transfer of the insect growth regulator, pyriproxyfen, to larval habitats, Tropical Medicine, 1994, 243-248, 36.

Chism et al., Horizontal transfer of the insect growth regulator pyriproxyfen to larval microcosms by gravid *Aedes albopictus* and *Ochlerotatus triseriatus* mosquitoes in the laboratory, Medical and Veterinary Entomology, 2003, 211-220, 17.

Devine et al., Using adult mosquitoes to transfer insecticides to *Aedes aegypti* larval habitats, Proceedings of the National Academy of Sciences, USA, 2009, 11530-11534, 106.

Mavale et al., Venereal transmission of chikungunya virus by *Aedes aegypti* mosquitoes (Diptera: Culicidae), American Journal of Tropical Medicine & Hygiene, 2010, 1242-1244, 83.

Thompson et al., Venereal transmission of LaCrosse virus from male to female Aedes triseriatus, American Journal of Tropical Medicine & Hygiene, 1978, 187-196, 27.

Weinzierl et al., Insects Atractants and Traps, 1995, 1-9, Urbana, Ill. : Office of Agricultural Entomology, University of Illinois at Urbana-Champaign, College of Agriculture, Cooperative Extension Service, Urbana-Champaign, U.S.A.

Vail et al., Autodissemination of Plodia interpunctella (Hiibner) (Lepidoptera: Pyralidae) granulosis virus by healthy adults, Journal of Stored Products Research, 1993, 71-74, 29.

Moya et al., Evaluation of lufenuron as a chemosterilant against fruit flies of the genus *Anastrepha* (Diptera:66 Tephritidae), Pest Management Science, 2010, 657-663, 66.

Chadee et al., Egg-laying yellow fever mosquitoes avoid sites containing eggs laid by themselves or by conspecifics, Entomologia Experimentalis et Applicata, 1990, 295-298, 57.

Sihuincha et al., Potential use of pyriproxyfen for control of Aedes aegypti (Diptera: Culicidae) in Iquitos, Peru, Journal of Medical Entomology, 2005, 620-630, 42.

Suman et al., Point-source and area-wide field studies of pyriproxyfen autodissemination against urban container-inhabiting mosquitoes, Acta Tropica, 2014, 96-103, 135.

Gaugler et al., An autodissemination station for the transfer of an insect growth regulator to mosquito oviposition sites, Medical and Veterinary Entomology, 2012, 37-45, 26.

Snetselaar et al., Development and evaluation of a novel contamination device that targets multiple life-stages of *Aedes aegypti*, Parasites & Vectors, 2014, 1-10, 7:200.

* cited by examiner

FIG. 2A
FIG. 2B
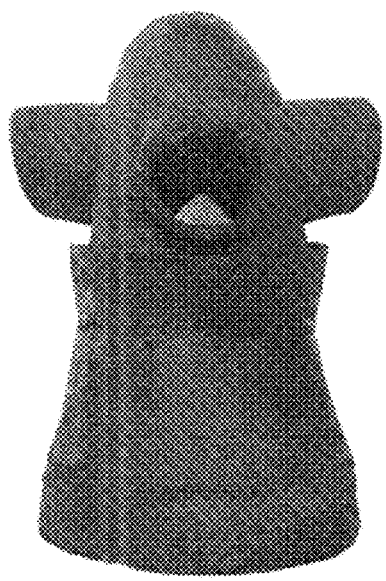
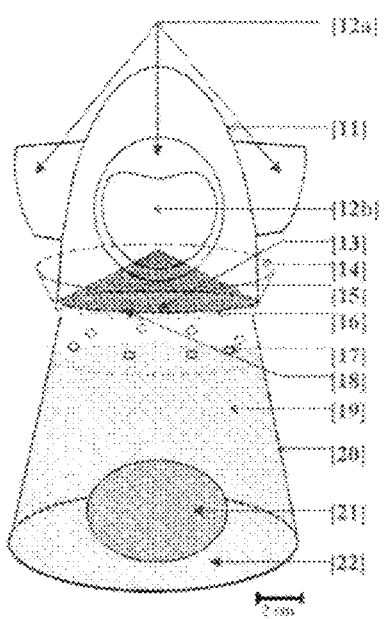

FIG. 4A Uncoated 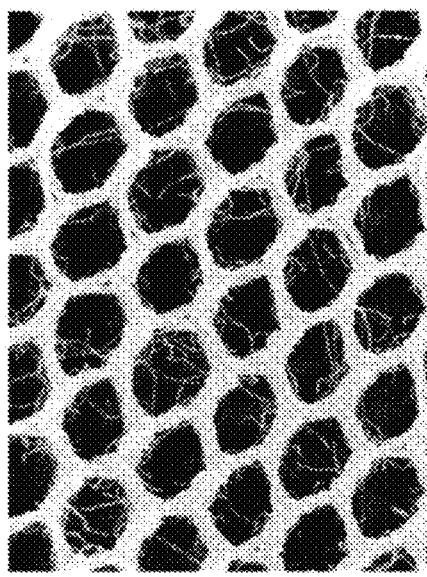 FIG. 4B Coated 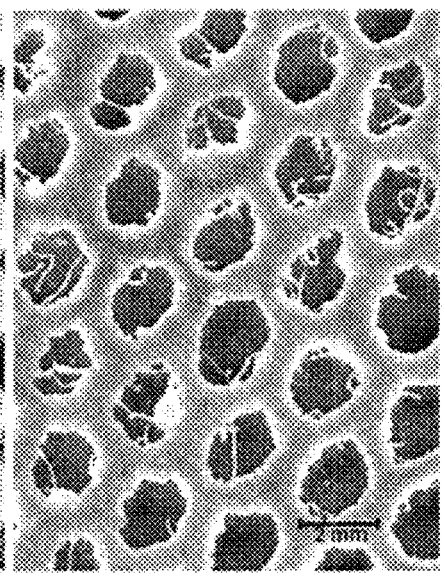

FIG. 5A  Abdomen
FIG. 5B  Foreleg Tarsi
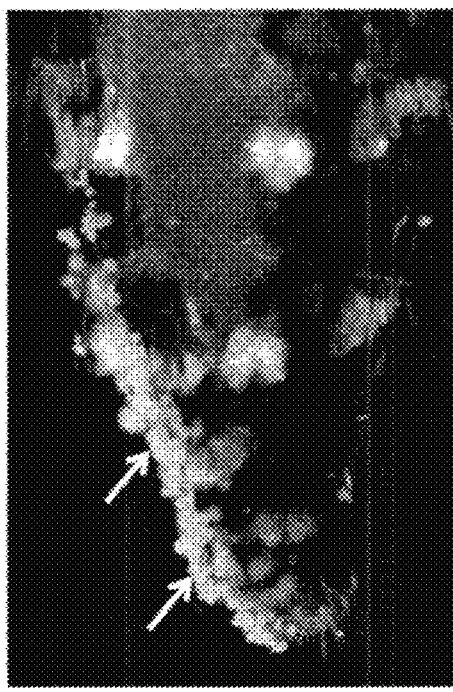

FIG. 6A  Virgin Female
FIG. 6B  Oviposition Seeking Female
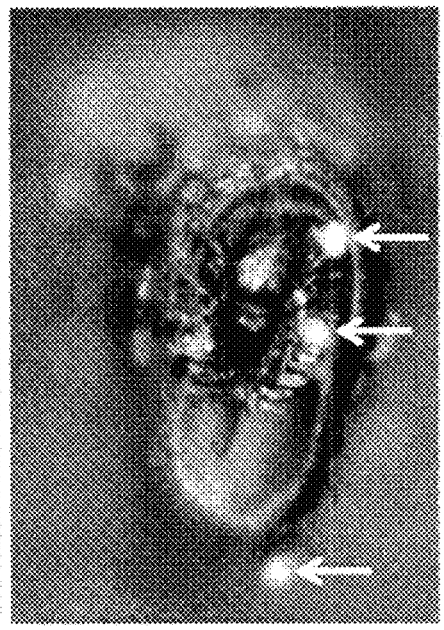

FIG. 10A  Before
FIG. 10B  After
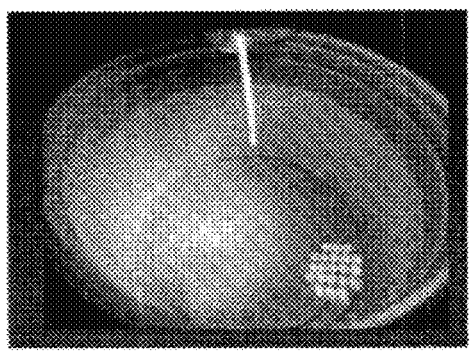
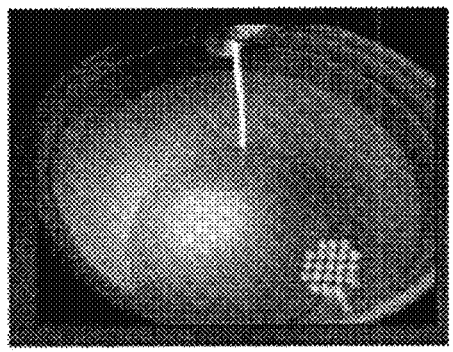

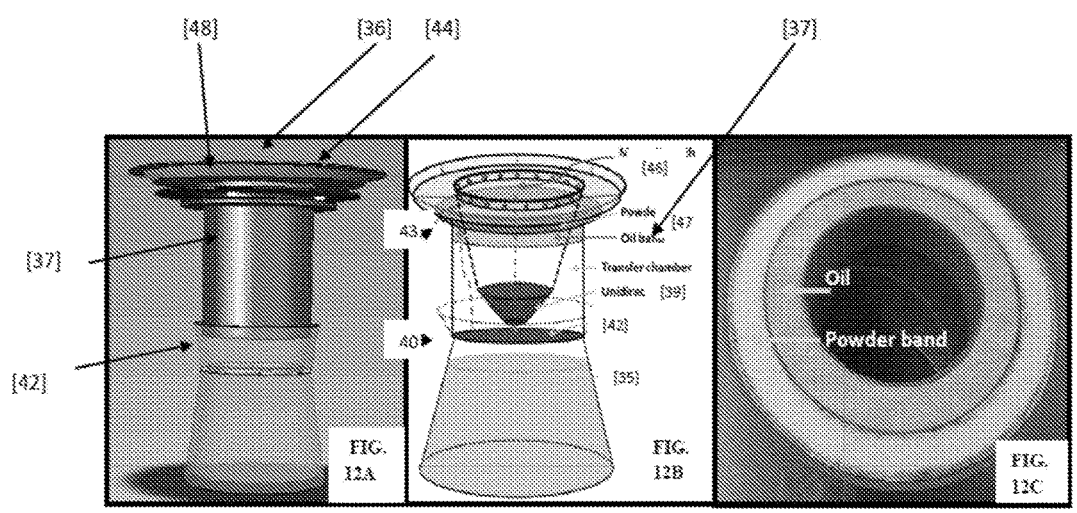

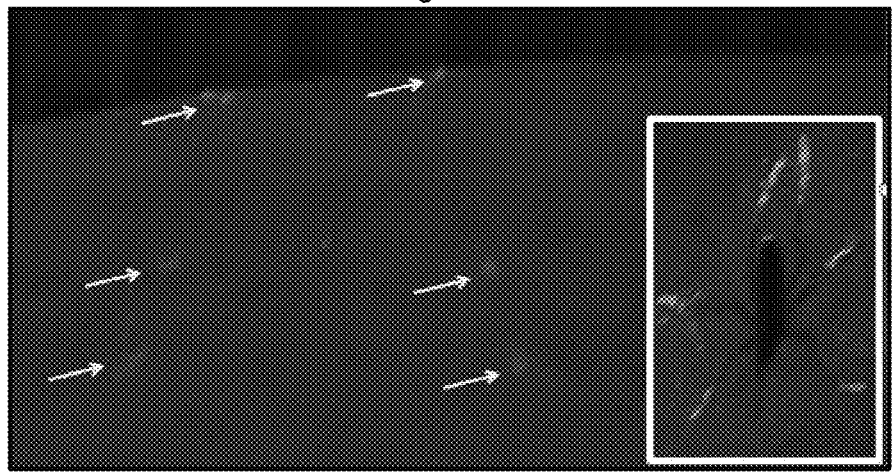
Figure 15
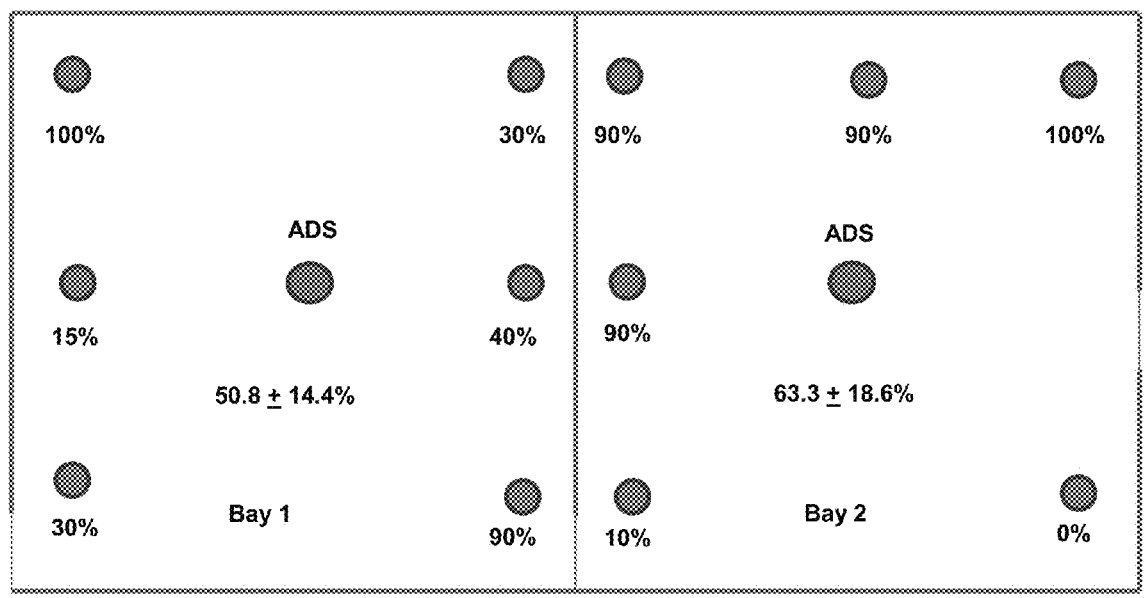
FIG. 16A
FIG. 16B

AUTODISSEMINATION OF AN INSECT-GROWTH REGULATOR FOR INSECT MANAGEMENT

CROSS REFERENCE TO RELATED APPLICATIONS

This application is a continuation-in-part application of U.S. patent application Ser. No. 13/863,359, filed Apr. 15, 2013, now U.S. Pat. No. 9,265,247, which is a continuation in part of PCT/US2011/56106 filed Oct. 13, 2011 which in turn claims priority from U.S. provisional patent application Ser. No. 61/393,681, entitled "Apparatus for autodissemination of an insect growth regulator for insect management", filed Oct. 15, 2010, and U.S. provisional patent application Ser. No. 61/490,449, entitled "Autodisseminated gel formulation in pest management", filed May 26, 2011. The entire disclosure of each of these applications is incorporated herein by reference.

STATEMENT OF GOVERNMENT FUNDING

This invention was made with government support under Grant Number 4-32131 awarded by the Department of Defense, Deployed WarFighter Protection Research Program and the Cooperative Agreement, Grant Numbers USDA-ARS-58-6615-8-105 and USDA-ARS-58-0208-0-066 awarded by the U.S. Department of Agriculture, Agricultural Research Service and NIH-SBIR Grant Number IR43AI096563-01A1. The government has certain rights in the invention.

FIELD OF THE INVENTION

The described invention relates to insect vectors, and methods and apparatus for control thereof.

BACKGROUND

Several publications and patent documents are cited through the specification in order to describe the state of the art to which this invention pertains. Each of these citations is incorporated herein by reference as though set forth in full.

Insects are arthropods of the class Insecta. They have an adult stage characterized by a hard exoskeleton, 3 pairs of jointed legs, and a body segmented into head, thorax, and abdomen. Insects comprise the most diverse and numerous class of the animal kingdom and include numerous species of mosquitoes, grasshoppers, true bugs, flies, fleas, bees, wasps, ants, lice, moths, and beetles. The number of species is estimated at between 6 and 10 million, with more than a million species already described. Because, insects represent more than half of all known living organisms and potentially represent more than 90% of the differing life forms on Earth, human contact with insects is unavoidable. Exposure to biting or stinging insects or to their remains can range in severity from benign or barely noticeable to life threatening.

Container mosquitoes are prime public and veterinary health threats. Peridomestic containers, such as tire ruts, buckets, tarps, stock tanks, cans, discarded tires, and container-laden trash piles provide reservoirs that allow peridomestic mosquitoes to come in close contact with people, livestock, and companion animals. Such mosquitoes are difficult to control.

Some of the most effective means of controlling mosquito vectors of disease include those that are insecticidal. Insecticidal means include the use of adulticides as space sprays or indoor residual applications; insecticide-treated materials (ITMs), such as curtains or bed nets; and the application of larvicides to aquatic habitats. However, the primary challenges of realizing sufficient coverage of an insect population, especially at large or on spatially complex scales, remain, due to the uncertainty over the relative productivity of specific habitats, the consequent need to identify and treat potential sites, and local constraints on financial and human resources.

Conventional control methods focusing on treating or eliminating larval habitats generally are only efficient when individual larval sources are large and not numerous. However, these approaches are opposite to the actual distribution of container mosquito larval habitats, which tend to be small, plentiful, and reside in areas where host contact is maximal.

Autodissemination is a pest management method in which insects contaminated with a biological or chemical active ingredient transfer lethal doses horizontally or vertically to other insects by means of mating, oviposition, aggregation, and other behaviors. Autodissemination with insect vectored entomopathogen dissemination is well known. Autodissemination has also been used in the management of agricultural pests using dusting methods with powder formulations of insecticides. However, powder formulations are prone to loss over time due to grooming behavior of a number of insects, including mosquitoes, thus reducing efficacy.

Autodissemination has been used to disperse entomopathogens, such as entomopathogenic fungi, baculoviruses and nematodes (See, e.g., Soper, R. (1978). Autodissemination of entomopathogens: fungi. *Future Strategies in Pest Management Systems* (ed. by G. E. Allen, C M. Ignoffo & R. P. Jaques) pp. 63-65. Proceedings of the National Science Foundation. United States Department of Agriculture and the University of Florida Workshop on Microbial Control of Insect Pests, Gainesville, Fla.; Yu, Z. & Brown, G. C (1997). Autodissemination of a beet armyworm (Lepidoptera: Noctuidae) baculovirus under laboratory conditions. *Journal of Economic Entomology*, 90, 1187-1194; Klein, M. G. & Lacey, L. A. (1999) An attractant trap for autodissemination of entomopathogenic fungi into populations of the Japanese beetle Popillia japonica (Coleoptera: Scarabaeidae). *Biocontrol Science and Technology*, 9, 151-158; Lacey, L., Bettencourt, A., Garrett, F., Simoes N. & Gaugler, R. (1993) Factors influencing parasitism of adult Japanese beetles by entomopathogenic nematodes. *Entomophaga*, 38, 501-9; Autoinoculating device for contaminating insects with active agents. U.S. Pat. No. 5,452,540; Method and apparatus for autodissemination of insect pathogens. U.S. Pat. No. 5,359,807; Dowd, P. F. & Vega, F. E. (2003) Autodissemination of *Beauveria bassiana* by sap beetles (Coleoptera: Nitidulidae) to overwintering sites. *Biocontrol Science and Technology*, 13, 65-75).

Pyriproxyfen is a pyridine-based insect growth regulator. It is a mosquito larvicide that does not impair adult activity (Kawada et al., 1993), is active at extraordinarily low concentrations (Aedes aegypti L. LC50=0.023 ppb or 200× the activity of temephos), and females can serve as a vehicle for transferring insecticides to other larval habitats (Schlein & Pener, 1990). It generally is effective against a variety of arthropoda, possesses reduced risk, low resistance potential, and extraordinary mosquito efficacy. However, chemical insecticides, such as insect growth regulators have seen minimal use against insects, such as container mosquitoes, for a number of reasons, including inability of replication and killing of contaminated insects restricting effective dispersal.

The described invention addresses the above issues by providing a system, apparati and gel formulations for autodissemination of an insect-growth regulator for insect management. The described invention is inexpensive, biodegradable, requires no maintenance, offers extended toxicant activity, and maximizes topical transfer of the toxicant by manipulating gravid female search behavior. The gel formulations are easy to transfer to an insect body part, are difficult for insects to clean from an insect body part, are easy to transfer from an insect to target sites, have extended time of efficacy and poses minimum environmental hazard and health risk.

SUMMARY OF THE INVENTION

According to one aspect, the described invention provides an autodisseminated gel formulation of a composition for autodissemination for management of insect populations, the gel formulation of the composition comprising: (1) an effective amount of at least one active ingredient; (2) at least one carrier; (3) at least one sticking agent; and (4) at least one emulsifying agent. According to one embodiment, the at least one active ingredient comprises an insecticide. According to one embodiment, the insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof. According to one embodiment, the at least one carrier is selected from the group consisting of a hydrocarbon, a fatty alcohol, a fatty acid, a glyceride, an ester of fatty acid, and a combination thereof. According to one embodiment, the at least one sticking agent is selected from the group consisting of a hydrocarbon, a fatty alcohol, a fatty acid, a glyceride, an ester of fatty acid, and a combination thereof. According to one embodiment, the at least one emulsifying agent is selected from the group consisting of a non-ionic emulsifying agent, an anionic emulsifying agent and a cationic emulsifying agent, and a combination thereof.

According to one embodiment, the gel formulation further comprises at least one particulate ingredient. According to one embodiment, the at least one particulate ingredient is selected from the group consisting of a clay powder, a silica powder, a talc powder, and a combination thereof. According to one embodiment, the gel formulation topically contaminates an insect. According to one embodiment, the insect is selected from the group consisting of a mosquito, a grasshopper, a true bug, a fly, a flea, a bee, a wasp, an ant, a louse, a moth, and a beetle, a member of *Arthropoda*, and a combination thereof. According to one embodiment, the insect is selected from the group consisting of an insect seeking oviposition, an insect seeking mating, an insect seeking aggregation behavior, an insect engaged in feeding, an insect engaged in overwintering, an insect engaged in foraging, and a combination thereof. According to one embodiment, the gel formulation is capable of being applied on an applicator that attracts the insect, wherein the gel formulation is capable of transferring to an insect body part, of sticking to such insect body part, and of being released from the insect body part into a target aqueous body where the insect propagates. According to one embodiment, the gel formulation is capable of controlling at least one larval population of the insect by interrupting the insect life cycle.

According to one embodiment, the at least one active ingredient is present at a concentration effective to kill at least 60%, at least 65%, at least 70%, at least 75%, at least 80%, at least 85%, at least 90%, at least 95%, at least 96%, at least 97%, at least 98%, at least 99%, or 100% of the larval population in the target aqueous body by release from a single contaminated gravid female insect.

According to one embodiment, the applicator is selected from the group consisting of: (I) an apparatus for autodissemination, the apparatus comprising: (1) a cap component, wherein the cap component comprises (i) a plurality of openings, and (ii) a plurality of auto-filling holes; (2) a cup component, wherein the cup component comprises (i) a water absorbing gel; (ii) a plurality of overflow protection holes, and (iii) a weighted base; (3) a mesh component, wherein the mesh component is coated with the gel formulation; (II) an apparatus for autodissemination, the apparatus comprising: (1) a cap component, wherein the cap component comprises (i) a transfer chamber; (ii) a plurality of of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component, wherein the mesh component is coated with the gel formulation; and (III) an apparatus for autodissemination, the apparatus comprising: (1) a cap component, wherein the cap component comprises (i) a transfer chamber; (ii) at least one horizontal entrance opening; (iii) a plurality of vertical window openings; (iv) a plurality of window shields, wherein each window shield is coated with the gel formulation on its inner surface and cover a vertical window opening and containing an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component.

According to another aspect, the described invention provides an apparatus for autodissemination to topically contaminate an insect, the apparatus comprising: (1) a cap component, wherein the cap component comprises (i) a plurality of openings, and (ii) a plurality of auto-filling holes; (2) a cup component, wherein the cup component comprises (i) a water containing reservoir; and (ii) a plurality of overflow protection holes; and (3) a mesh component. According to one embodiment, at least one of the cap component and the cup component comprise: a molded optionally biodegradable material, wherein the molded optionally biodegradable material is selected from the group consisting of wet shredded cardboard, a pasteboard, a cellulose-based material, or combinations thereof; and a binder, wherein the binder is a binder selected from the group consisting of a corn starch, peat moss, an egg carton, rice hulls, a newspaper, straw, a natural polymer(s), or combinations thereof. According to one embodiment, at least one of the cap component and the cup component further comprise a waterproofing agent, wherein the water-proofing agent is paraffin wax. According to one embodiment, at least one of the cap component and the cup component further comprise a gel formulation of a composition comprising at least one active ingredient, wherein the active ingredient comprises an insecticide, and wherein the insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof. According to one embodiment, the insect-growth regulator is pyriproxyfen. According to one embodiment, the insect-growth regulator is present at a concentration effective to kill at least 60%, at least 65%, at least 70%, at least 75%, at least 80%, at least 85%, at least 90%, at least 95%, at least 96%, at least 97%, at least 98%, at least 99%), or 100% of a larval population in a target aqueous body by release from a single contaminated gravid female insect. According to one embodiment, the mesh component is a cotton fabric. According to one embodiment, the cup component further comprises an insect attractant. According to one embodiment, the insect attractant comprises a substrate for bacterial growth and a microbial population, wherein the microbial population produces the insect attractant. According to one embodiment, the insect is selected from the group consisting of a mosquito, a grasshopper, a true bug, a fly, a flea, a bee, a wasp, an ant, a louse, a moth, and a beetle, a member of *Arthropoda*, and a combination thereof. According to one embodiment, the insect is selected from the group consisting of an insect seeking oviposition, an insect seeking mating, an insect seeking aggregation behavior, an insect engaged in feeding, an insect engaged in overwintering, an insect engaged in foraging, and a combination thereof. According to one embodiment, the cup component further comprises (iii) a water absorbing gel and (iv) a weighted base; and the mesh component is coated with a gel formulation of a composition comprising at least one active ingredient, wherein the at least one active ingredient comprises an insecticide. According to one embodiment, the insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof. According to one embodiment, the insect-growth regulator is pyriproxyfen. According to one embodiment, the cap component comprises a plurality of openings, wherein each of the openings is on a portal arm; the cup component further comprising (iii) a water absorbing gel and (iv) a weighted base; and the mesh component is coated with a gel formulation of a composition comprising at least one active ingredient, wherein the at least one active ingredient comprises an insecticide. According to one embodiment, the insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof. According to one embodiment, the insect-growth regulator is pyriproxyfen. According to one embodiment, the cap component comprises (i) a plurality of openings, comprising at least one horizontal entrance opening, a plurality of vertical window openings, wherein each of the vertical window openings is covered with a window shield, wherein the window shield is coated with a gel formulation of a composition comprising at least one active ingredient, wherein the at least one active ingredient comprises an insecticide; (ii) a unidirectional funnel; and (iii) a plurality of auto-filling holes. According to one embodiment, the insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof. According to one embodiment, the insect-growth regulator is pyriproxyfen.

According to another aspect, the described invention provides a method for managing insect populations, the method comprising the steps of: (1) preparing a gel formulation of a composition comprising at least one active ingredient, at least one carrier, at least one sticking agent, and at least one emulsifying agent; and (2) placing an amount of the gel formulation comprising at least one insect active ingredient on an applicator within a range of insect behavior site. According to one embodiment, the at least one of the active ingredient comprises an insecticide, wherein the insecticide is selected from the group consisting of an insect growth regulator, an organophosphate, carbamate, a chlorinated diphenyl alkane, a cyclodiene, a rotenoid, an organic fluoride compound, a nicotinoid, a hexachlorocyclohexane, and a combination thereof. According to one embodiment, the gel formulation of the composition further comprises at least one particulate ingredient, wherein the particulate ingredient is selected from the group consisting of a clay powder, a silica powder, a talc powder, and a combination thereof. According to one embodiment, the applicator is selected from the group consisting of: (I) an apparatus for autodissemination, the apparatus comprising: (1) a cap component, wherein the cap component comprises (i) a plurality of openings, and (ii) a plurality of auto-filling holes; (2) a cup component, wherein the cup component comprises (i) a water absorbing gel; (ii) a plurality of overflow protection holes, and (iii) a weighted base; and (3) a mesh component, wherein the mesh component is coated with the gel formulation; (II) an apparatus for autodissemination, the apparatus comprising: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component, wherein the mesh component is coated with the gel formulation; and (III) an apparatus for autodissemination, the apparatus comprising: (1) a cap component, wherein the cap component comprises (i) a transfer chamber; (ii) at least one horizontal entrance opening; (iii) a plurality of vertical window openings; (iv) a plurality of window shields, wherein each window shield is coated with the gel formulation on its inner surface and cover a vertical window opening and containing an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component.

According to another aspect, the described invention provides a method for autodisseminating an insect-growth regulator, the method comprising dispersing an apparatus comprising: (1) a cap component, wherein the cap component comprises (i) a plurality of openings, and (ii) a plurality of auto-filling holes; (2) a cup component, wherein the cup component comprises (i) a water containing reservoir; and (ii) a plurality of overflow protection holes; and (3) a mesh component.

According to another aspect, the described invention provides a system for autodisseminating an active ingredient for insect management, the system comprising (I) an autodissemination apparatus, the apparatus comprising: (1) a cap component, wherein the cap component comprises (i) a plurality of openings, and (ii) a plurality of auto-filling holes; (2) a cup component, wherein the cup component comprises (i) a water containing reservoir; and (ii) a plurality of overflow protection holes; and (3) a mesh component; and (II) a gel formulation of a composition comprising at least one active ingredient, wherein the at least one active ingredient comprises an insect growth regulator.

In yet another aspect of the invention, a biphasic autodissemination station (ADS) is provided which is effective to topically contaminate an insect, the station providing a unidirectional path for insects, thereby enhancing contamination. An exemplary station comprises (i) a cover plate, effective to both shelter formulations from weather and collect rain to refill the reservoir; (ii) a reservoir component, the reservoir component comprising a i) plurality of overflow protection holes and optionally comprising an attractant; (iii) a mesh component to prevent mosquitoes from entering said reservoir; (iv) a transfer chamber having a unidirectional cone inserted therein; (v) a vertical or horizontal coatable band disposed within said transfer chamber, said vertical or horizontal coatable band comprising an oil/gel formulation and being contiguous with an upper horizontal flat ring surface, said flat ring surface comprising a powder formulation, said powder formulation comprising an active ingredient, a slight ridge being present between said vertical coatable surface and said flat ring surface to prevent mixing of said oil and powder formulations, wherein said insect must first traverse said oil/gel formulation, followed by traversal of said powder formulation in order to exit said station; said station attracting insects, contaminating said insects with said oil and powder formulations, wherein the contamination is effective to disrupt the life cycle of said insect. In a preferred embodiment the station is assembled using biodegradable materials. In another embodiment the cover component and the reservoir component further comprise a water-proofing agent.

Preferably, the powder formulation comprises an insect population controlling active ingredient selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, an insect pathogen, and a combination thereof. In a particularly preferred embodiment, the insect-growth regulator is pyriproxyfen. In another aspect the oil/gel formulation comprises an insect population controlling active ingredient selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, an insect pathogen, and a combination thereof. In preferred embodiments, the active ingredient comprises 5-80% of said formulations. The biphasic ADS station of the invention provides several advantages, these include without limitation, unidirection passage resulting in enhanced active ingredient load onto said insect and increased active ingredient persistence on said insect which in turn enhances serial dissemination.

In one embodiment, an improved gel formulation is provided, comprising 40% pyriproxyfen as a.i, 36% methylated seed oil and 14% fumed silica as carrier, 4% of polysorbete-20 and 6% of Sodium Dodecyl Sulfate as emulsifier. Surprisingly, this gel formulation is stable under extreme weather conditions.

In an alternative embodiment, the apparatus for autodissemination comprises (1) a reservoir having a hollow center for insertion of a wide mouth unidirectional funnel, said mouth being wide enough to permit leaf passage, said reservoir having a having (2) a mesh cover; (3) a transfer plate and an optional cover, said transfer plate having insect growth regulator affixed thereto in a form suitable for transfer to any passing insect. In certain embodiments, the transfer plate contains a cover and a formulation ring filled with gel formulation, said formulation ring optionally being in contact with a wicking fabric to inhibit drying of said gel formulation, gap size between said plate and said cover varying according to insect body size and being adjustable via tightening the cover onto said transfer plate.

In another aspect, the reservoir in the apparatus is contacted with a wick attached to an infusion pouch comprising an attractant containing 15 gm oak leaves, 30 grm oak wood and 1 L water.

The present invention also comprises a method for autodisseminating an insect population controlling active ingredient for control of insect populations comprising dispersing one or more biphasic autodissemination stations as described above in an area where control of insect populations is desirable.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows an illustrative representation of an autodissminination apparatus for insect management. The illustrative apparatus includes: a cap component [1]; a pyriproxyfen-coated mesh component [2]; at least one entrance [3]; a trough [4]; a plurality of auto-filling holes [5]; a plurality of overflow protection holes [6]; a cup component [7]; a water reservoir [8]; a water absorbing gel [9]; and a weight-supported base component [10].

FIGS. 2A-2B shows a picture (FIG. 2A) and an illustrative representation (FIG. 2B) of an autodissminination apparatus for insect management. The illustrative apparatus includes: a transfer chamber [11]; a plurality of portal arms [12*a*], each containing an opening or portal for entry or exit [12*b*]; a bottom edge of the transfer chamber [13]; a gutter [14]; a mesh component [15]; a plurality of auto-filling holes [16]; a plurality of overflow protection holes [17]; a rim of the reservoir component [18]; a volume of water [19]; a reservoir component [20]; an optional bag containing an insect attractant [21]; and a reservoir bottom [22].

FIG. 3 shows an illustrative representation of an autodissemination apparatus for insect management. The illustrative apparatus includes: at least one horizontal entrance opening [23]; a plurality of vertical window openings [24]; a plurality of window shields [25], each window shield covers a vertical window opening, each window shield is coated on its inner surface with an insecticide, and each window shield contains an exit opening [26]; a unidirectional funnel [27]; a transfer chamber [28]; a gutter [29]; a mesh component [30]; a plurality of auto-filling holes [31]; a plurality of overflow protection holes [32]; a reservoir component [33]; and a volume of water [34].

FIGS. 4A-4B show a micrograph, obtained with a compound microscope (Olympus SZX16, Japan) and a digital camera (ProgRes CF Scan, Jenoptic, Germany), showing a transfer mesh (platform for insect growth regulator transfer to adult mosquitoes entering an autodessimination station) uncoated (FIG. 4A) and coated (FIG. 4B) with pyriproxyfen-impregnated silica particles.

FIGS. 5A-5B shows a micrograph, obtained with a compound microscope (Olympus SZX16, Japan) and a digital camera (ProgRes CF Scan, Jenoptic, Germany), showing abdomen (FIG. 5A) and foreleg tarsi (FIG. 5B) showing adherence of pyriproxyfen-impregnated particles (arrows) to *Aedes albopictus* female mosquitoes.

FIGS. 6A-6B show a micrograph, obtained with a compound microscope (Olympus SZX16, Japan) and a digital camera (ProgRes CF Scan, Jenoptic, Germany), showing the distal view of a virgin *Aedes albopictus* female (FIG. 6A) and the distal view of a an oviposition-seeking *Aedes albopictus* female (FIG. 6B) showing pyriproxyfen-impregnated particles (arrows) transferred by mating from contaminated males to females.

FIGS. 10A-10B shows before (FIG. 10A) and after (FIG. 10B) snapshots of a gel formulation being touched upon an aqueous surface demonstrating the effective release of the gel formulation to the aqueous phase and its subsequent dispersal.

Figure 11:
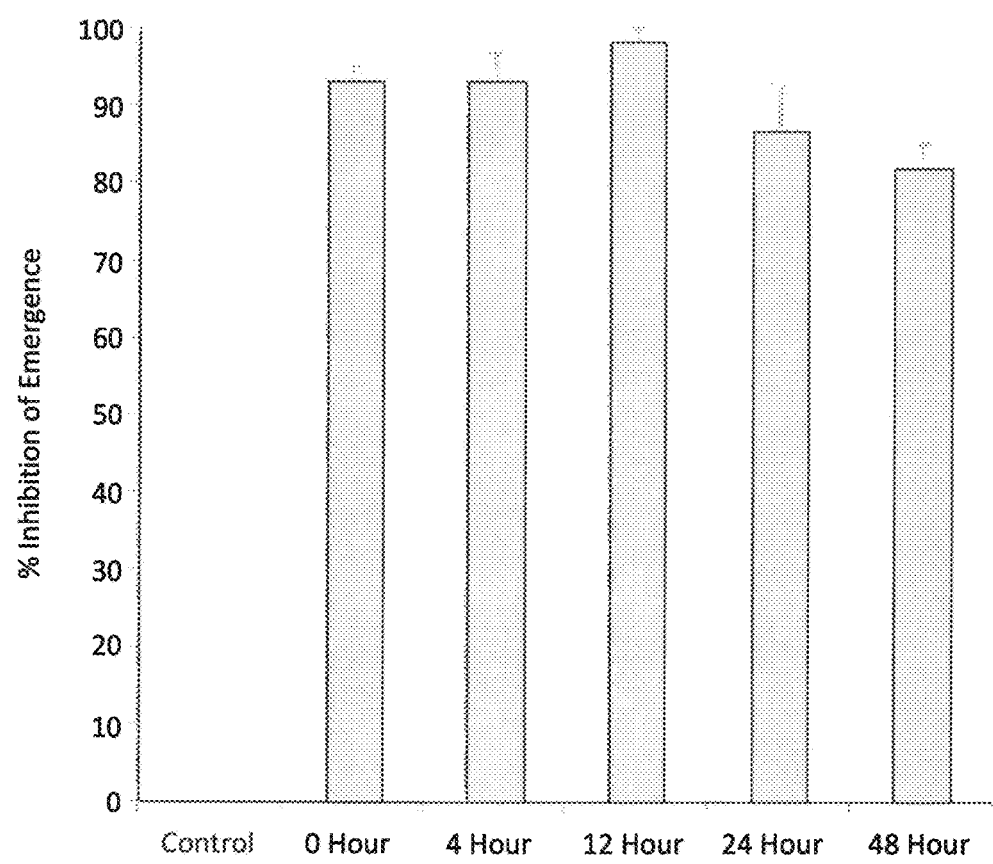

FIG. 11 demonstrates that a gel formulation is resistant to removal of active ingredient by grooming behavior.

Figure 12D:
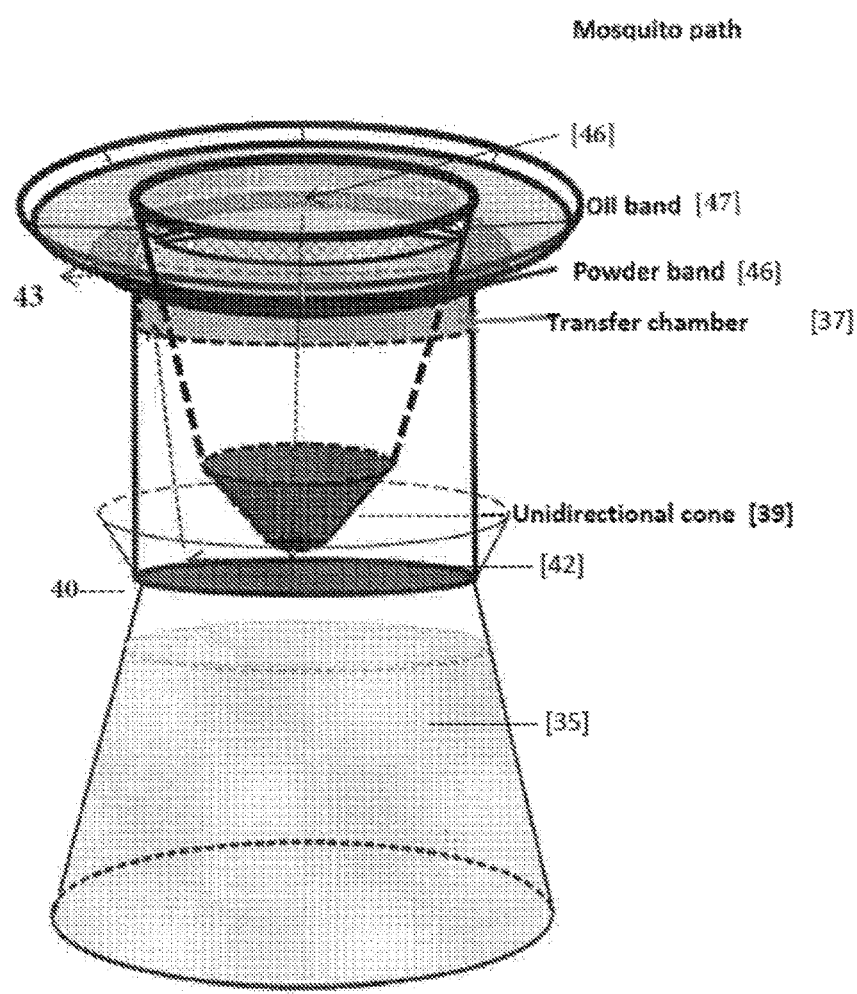

FIGS. 12A-12D: FIG. 12A. Image of the dual treatment ADS prototype that consists of reservoir and transfer chamber. FIG. 12B. Schematic drawing showing the interior of the transfer chamber and unidirectional core. FIG. 12C. Topical view of the modified chamber of second prototype showing both oil and powder bands are mounted on the same plate for easy manufacture and formulation coating. FIG. 12D. A larger view showing disposition of the oil and powder band formulations.

Figure 13A:
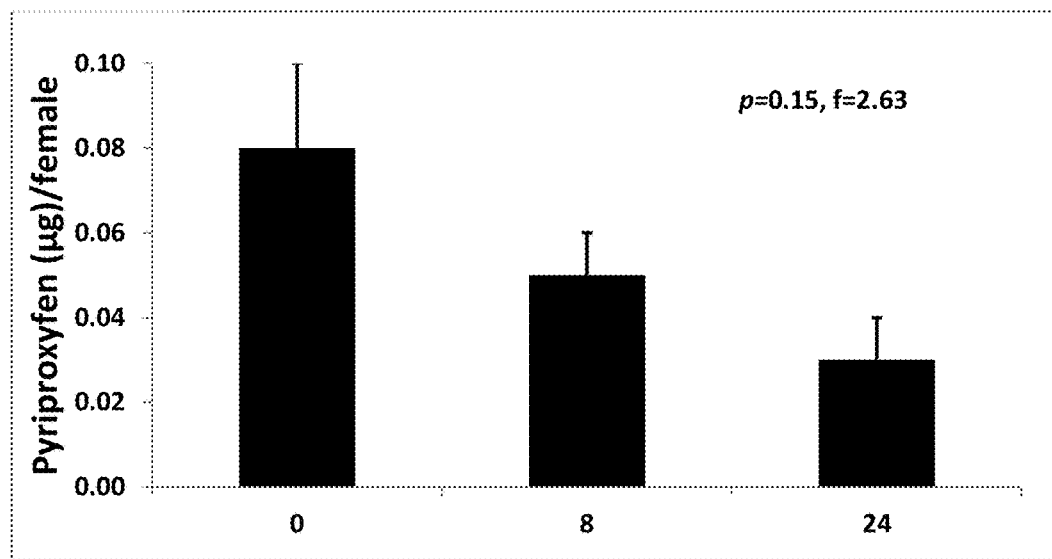
Figure 13B:
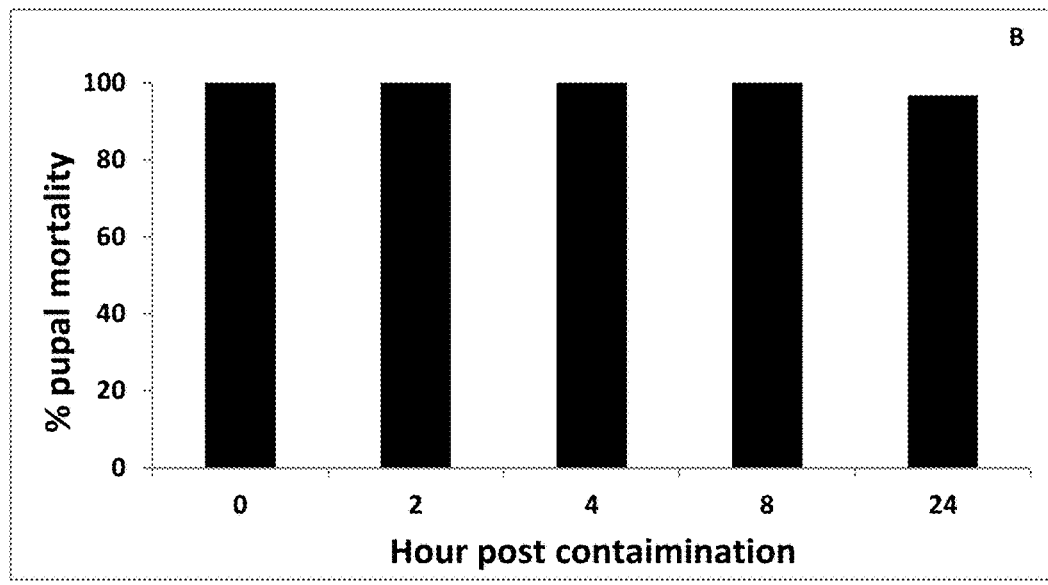

FIG. 13A-13B: Result of attachment and persistence assay in small cage (50×50×50 cm). FIG. 13A. Residue analysis of pyriproxyfen on each ADS contaminated gravid mosquito over time. FIG. 13B. Third instar larval bioassay results confirming the residue data. Even 24 h post contamination by the dual treatment system, the pyriproxyfen persisted on each mosquito still cause 96.7% pupal mortality of *Aedes albopictus*.

Figure 14:
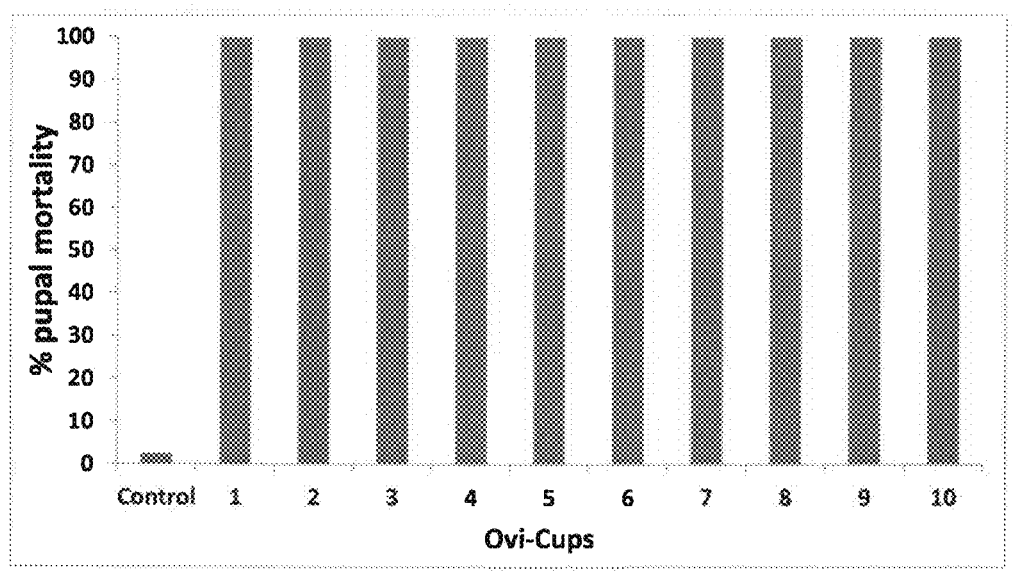

FIG. 14: Big room (31 m³) assay of the dual treatment ADS with 50 gravid females against 10 oviposition cups. In each cup tested, 100% emergence inhibition was achieved. FIG. 15: Mosquito footprints (arrows) visualized under UV light show evidence of transfer in the big room (31 m³) assay.

FIGS. 16A-16B: Greenhouse assay of the ADS efficacy against 6 containers in each bay (100 m³) with 100 gravid females for 5 days. FIG. 16A shows bay 1. FIG. 16B shows bay 2. The average pupal mortality for the 12 ovi-cups is 57.1+11.4%. The contamination rate is 91.6% among containers tested.

Figure 17:
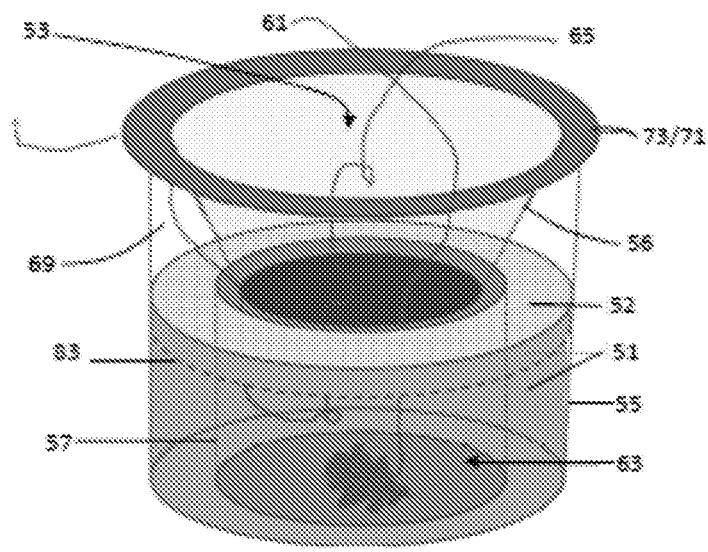

FIG. 17: Diagram of the leaf containing ADS design. The new ADS design includes a large unidirectional funnel (56) that allows any falling leaves to come through the exterior opening (53) at the top. The water in the reservoir (51) is housed in a circular tank (55) with a hollow cylindrical center (57). Leaves fall in from the top opening (53) and traverse the funnel (56) as shown in the blue line labeled Leaf path (61). The depth of the leaf chamber (63) should be sufficient to capture falling leaves throughout the mosquito season. Mosquito path (65) (red line) also includes entry through the top opening (53) lured by the attractant provide\d in the infusion pouch shown in FIG. 22. After failing to reach the water, the mosquito will go up and exit via an exit gap (78) in the transfer plate (71) formed between the formulation ring (79) and the transfer plate cover (73), where gel formulation (75) comprising an insect growth regulator (75) is embedded in the formulation ring (79) to contaminate the exiting mosquitoes before they leave the station. Also shown is mesh cover (52) over the opening of the reservoir (51) to prevent insects from entering the reservoir (51), where the mesh cover (52) encircles the hollow cylindrical center (57).

Figure 18:
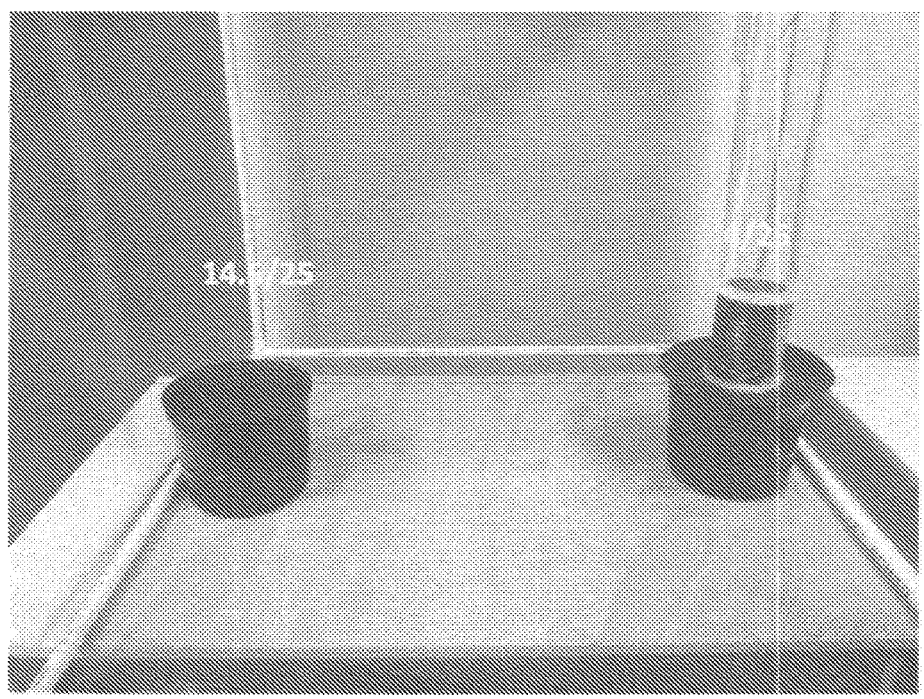

FIG. 18: Attraction test of the new design compared against the previous version.

Figure 19:
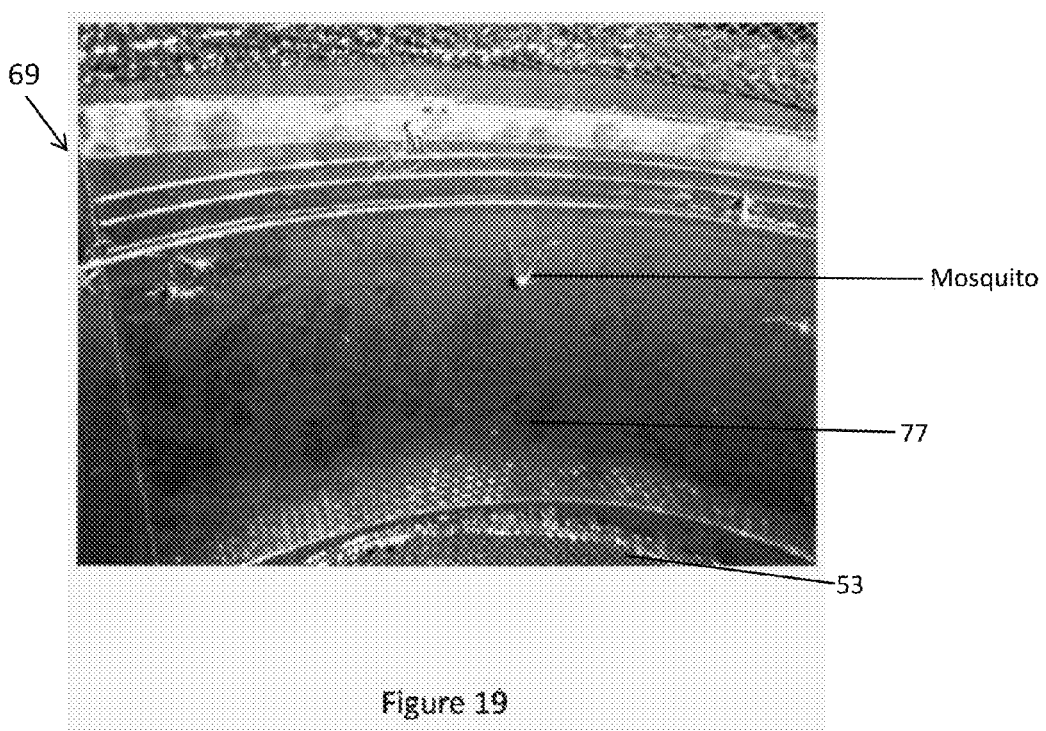

FIG. 19: Trapped mosquitoes which were attempting to exit the station from the top opening.

Figure 20:
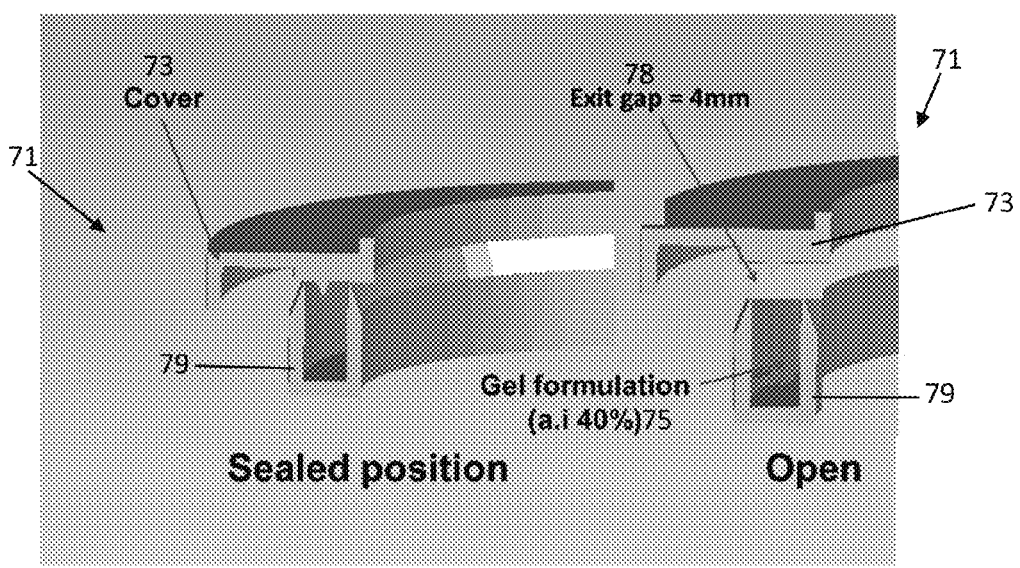

FIG. 20: A portion of the transfer plate design showing sealed and open position. The transfer plate (71) contains a cover (73) and a formulation ring (79) which is filled with gel formulation (75).

Figure 21:
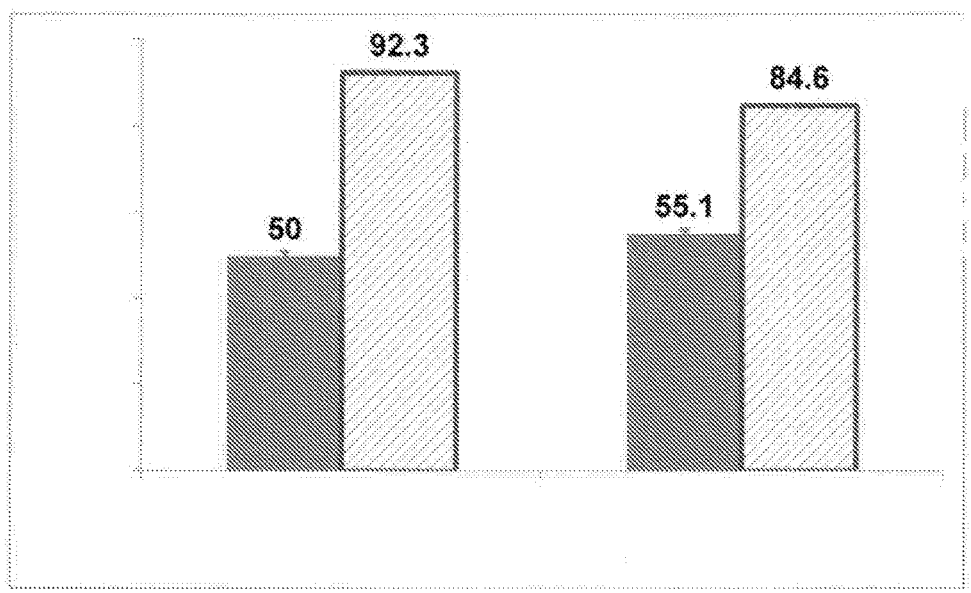

FIG. 21: Percentage contamination mosquito legs (solid bars) and mosquitoes (hatched bars).

Figure 22:

FIG. 22: Infusion pouch (85) containing attractant shown on a platform (88) against the inside wall of the circular tank (55) hanging above the water surface (83) in the reservoir (51), with a cotton wick (87) inserted into water to keep the active ingredients of the attractant moisturized.

Figure 23:
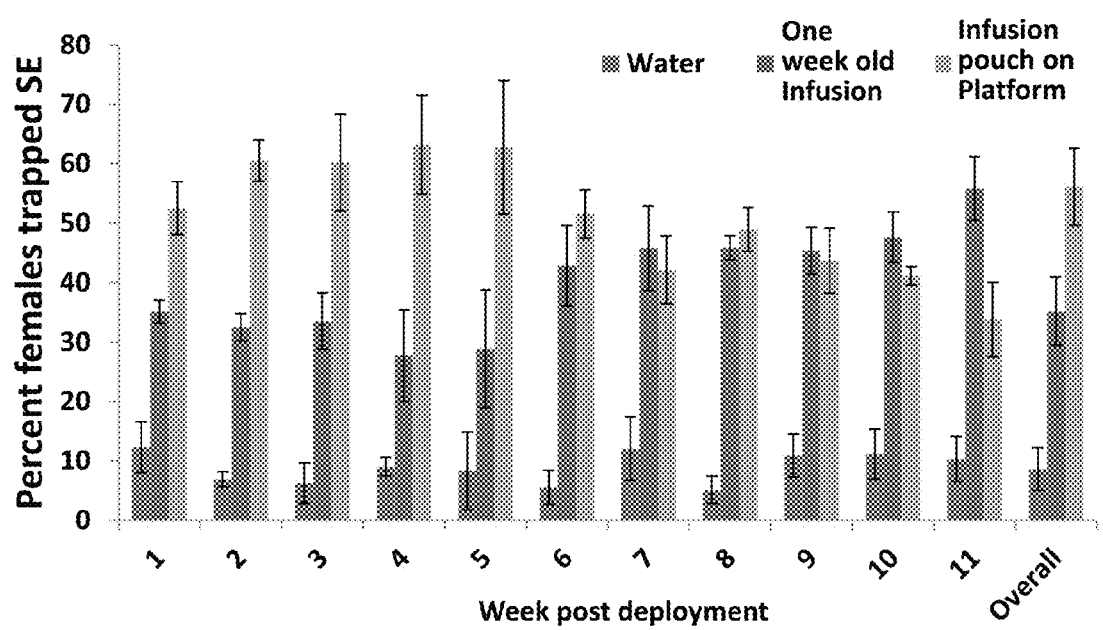

FIG. 23: Comparative weekly attractancy of infusion pouch on platform with plain water and oak leaf and wood infusions (one week old), against gravid *Aedes albopictus*.

Figure 24:
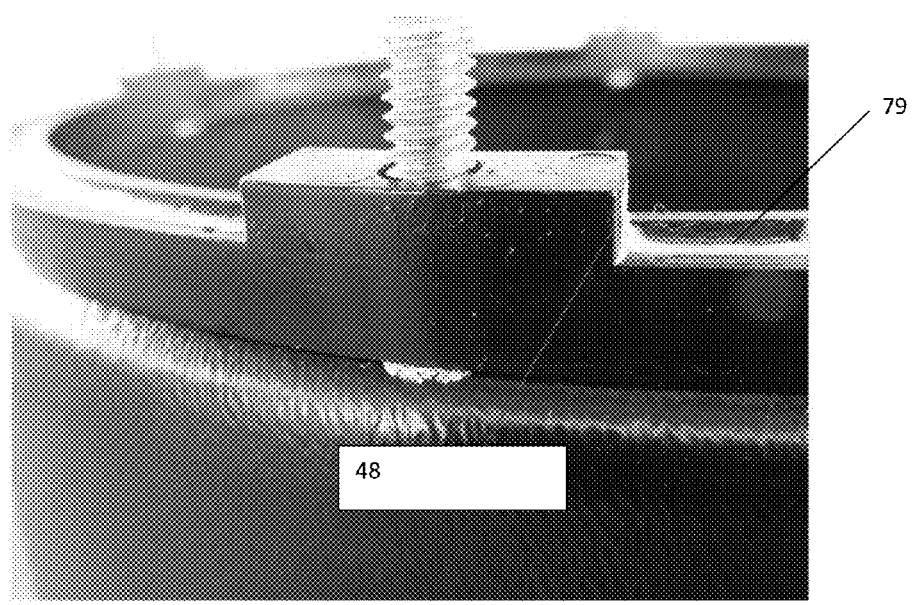

FIG. 24: The spacer blocks (48) forming a 5 mM gap for mosquito exit are shown.

Figure 25:
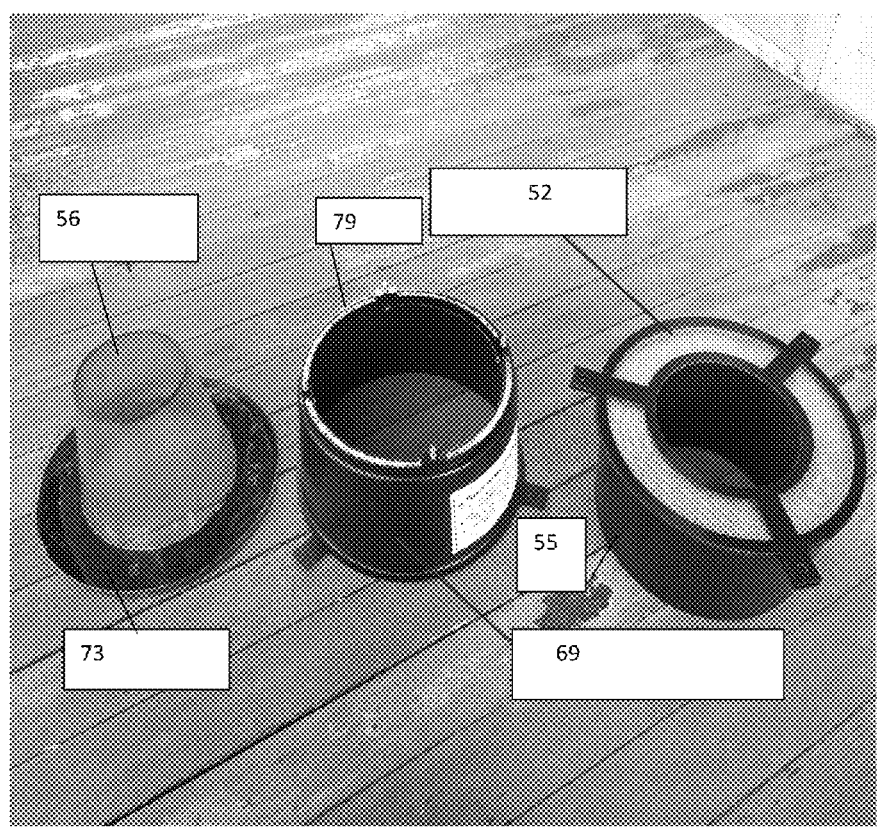

FIG. 25: A disassembled ADS showing the component parts. The unidirectional funnel (56), transfer plate cover (73), transfer chamber (69), formulation ring (79), mesh (52) and circular tank (55) are shown.

Figure 26:

FIG. 26: An assembled ADS showing the transfer plate cover (73), transfer chamber (69) and circular tank (55) and the exterior opening (53).

DETAILED DESCRIPTION

Glossary

The term "binder" as used herein refers to a material used to impart cohesive qualities that offers stability and maintains shape and integrity to a substance ensuring that the substance remains intact during or after manipulation.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration. The carrier can be inert, or it can have beneficial effects. The terms "excipient", "carrier", or "vehicle" are used interchangeably to refer to carrier materials suitable for formulation and administration of compositions described herein. Carriers and vehicles useful herein include any such materials know in the art which are nontoxic and do not interact with other components.

The term "contained" as used herein refers to the characteristic of being held within a confined area and not prone to being dispersed.

The term "diluent" as used herein refers to an agent that is used to increase the bulk of the active ingredient without affecting the biological effect of the active ingredient.

The term "emulsifiers" as used herein are agents that promote the formation and stabilization of an emulsion.

The term "emulsion" as used herein refers to a two-phase system prepared by combining two immiscible liquid carriers, one of which is dispersed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "foraging" as used herein refers to insect behavior for seeking food.

The term "glue-like" as used herein describes the sticky nature of the formulation that makes it difficult for the insect to remove or dislodge it.

The term "insect" as used herein means an arthropod in the class Insecta, characterized by six legs, up to four wings, and a chitinous exoskeleton.

The term "insect-growth regulator" ("IGR") as used herein means a synthetic chemical similar to insect juvenile hormone, which, in some insect species, possesses the same function as native insect juvenile hormone in inhibiting insect life cycle. For example, IGRs regulate insect growth by structurally mimicking insect juvenile hormone. Exemplary insect species that can be controlled by the use of IGRs include, but are not limited to, mosquitoes, grasshoppers, true bugs, flies, fleas, bees, wasps, ants, lice, moths, and beetles. Additional species include any member of *Arthropoda*. Exemplary IGRs include but are not limited to pyriproxyfen.

The term "overwintering" as used herein refers to the insect behavior of seeking shelter in sites (overwintering sites), such as under loose bark of trees, fallen leaves and other ground debris, to pass through cold winter conditions.

The term "particle" or "particulate" as used herein refers to an extremely small constituent, a minute portion, piece, fragment, or amount that may contain in whole or in part at least one active ingredient as described herein.

The term "peridomestic" as used herein refers to being of or pertaining to living in and around human habitations.

The term "site of application" as used herein refers to a position or location within the target aqueous body where the gel formulation of the composition is released from the insect body part.

The term "solution" generally is considered as a homogeneous mixture of two or more substances. It is frequently, though not necessarily, a liquid. In a solution, the molecules of the solute (or dissolved substance) are uniformly distributed among those of the solvent.

The term "solvent" as used herein refers to a substance capable of dissolving another substance (termed a "solute") to form a uniformly dispersed mixture (solution).

The term "stabilizer" as used herein refers to a substance that is used to preserve the physical, chemical, and other specifications of an active ingredient against physical, chemical or any other biochemical process which would reduce the biological effect of the active ingredient, e.g., preventing larvae from developing into adulthood.

The term "surfactant", as used herein, refers to a surface-active agent that acts to reduce surface tension, which is the elastic like force existing in the surface of a body, e.g., a liquid, at an interface between two liquids, or that between a liquid and a solid, tending to minimize the area of the surface, caused by asymmetries in the intermolecular forces between surface molecules. Surfactants usually are organic compounds that contain both hydrophobic groups and hydrophilic groups, i.e., are amphiphilic. Surfactants can be anionic, cationic, nonionic, and zwitterionic.

As used herein, "Technical pyriproxyfen" is a commercially available concentrated form of pyriproxyfen.

As used herein, the terms "topical" and "topically" are used interchangeably to refer to delivery of an insect growth regulator onto one or more surfaces of an insect's body part, including epithelial surfaces.

Autodisseminated Gel Formulation

According to one aspect, the described invention provides an autodisseminated gel formulation of a composition comprising at least one active ingredient for management of insect populations. According to one embodiment, the gel formulation of the composition is capable of transferring to an insect body part and sticking to such insect body part. According to another embodiment, the gel formulation of the composition is further capable of being released from the insect body part into a target aqueous body where the insect propagates, and is thereby capable of controlling insect larval populations by interrupting the insect life cycle. Such insects include, but are not limited to, mosquitoes, grasshoppers, true bugs, flies, fleas, bees, wasps, ants, lice, moths, and beetles, or any member of *Arthropoda*. According to one embodiment, the insect population comprises a peridomestic insect population. According to one embodiment, the insect comprises an oviposition-seeking insect. According to one embodiment, the insect comprises a mating insect. According to one embodiment, the insect comprises an insect seeking aggregation behavior. According to one embodiment, the insect comprises an insect engaged in feeding. According to one embodiment, the insect comprises an insect engaged in overwintering. According to one embodiment, the insect comprises an insect engaged in foraging.

Nonlimiting examples of an insect to which the gel formulation of the composition of the present invention is applicable include the following: *Hemiptera* insects, including, without limitation, planthoppers such as small brown planthopper (*Laodelphax striatellus*), brown planthopper (*Nilaparvata lugens*), white-backed rice planthopper (*Sogatella furcifera*) and the like, leafhoppers such as green rice leafhopper (*Nephotettix cincticeps*), Taiwan green rice leafhopper (*Nephotettix virescens*) and the like, aphides such as cotton aphid (*Aphis gossypii*), green peach aphid (*Myzus persicae*), apple aphid (*Aphis citricola*), turnip aphid (*Lipaphis pserudobrassicae*), pear grean aphid (*Nippolachnus phi*), black citrus aphid (*Toxoptera aurantil*), tropical citrus aphid (*Toxoptera ciidius*) and the like, stink bugs such as green stink bug (*Nezara antennata*), *Cletus punctiger*, bean bug (*Riptortus clavetus*), brownwinged green bug (*Plautia stali*) and the like, whiteflies such as greenhouse whitefly (*Trialeurodes vaporariorum*), sweet-potato whitefy (*Bemisia tabaci*), silverleaf whitefly (*Bemisia argentifolii*) and the like, scale insects such as California red scale (*Aonidiella aurantii*), San Jose scale (*Comstockaspis perniciosa*), citrus snow scale (*Unaspis citri*), white peach scale (*Pseudaulacaspis pentagona*), brown olive scale (*Saissetia oleae*), purple scale (*Lepidosaphes beckii*), red wax scale (*Ceroplastes rubens*), cottonycushion scale (*Icerya purchasi*) and the like, lace bugs, jumping plant louses and the like; Lepidopteran insects, including, without limitation, Pyralidae such as rice stem borer (*Chilo suppressalis*), rice leafroller (*Cnaphalocrocis medinalis*), European corn borer (*Ostrinia nubilalis*), cabbage webworm (*Hellulla undalis*), bluegrass webworm (*Parapediasia teterrella*), cotton leafroller (*Notarch derogata*), Indian meal moth (*Plodia interpuncterlla*) and the like, Noctuidae such as tabaco cutworm (*Spodoptera litura*), rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and the like, Pieridae such as small white (*Pieris rapae*) and the like, Tortricidae such as *Adoxophyes* spp., oriental fruit moth (*Grapholita molesta*), codling moth (*Cydia pomonella*) and the like, Carposinidae such as peach fruit moth (*Carposina niponensis*) and the like, Lyonetiidae such as *Lyonetia* spp. and the like, Lymantriidae such as *Lymantria* spp., *Euproctis* spp. and the like, Yponomeutidae such as diamondback moth (*Plutela xylostella*) and the like, Gelechiidae such as pink ball worm (*Pectinophora gossypiella*) and the like, Arctiidae such as fall webworm (*Hyphantria cunea*) and the like, Tineidae such as casemaking clothes moth (*Tinea translucens*), webbing clothes moth (*Tineola bisselliella*) and the like; *Diptera* insects, including, without limitation, *Culex* spp; such as common mosquito (*Culex pipiens* pallens), oriental latrine fly (*Culex tritaeniorhynchus*) and the like, *Aedes* spp. such as dengue mosquito (*Aedes aegypti*), tiger mosquito (*Aedes albopictus*) and the like, *Anopheles* spp. such as Chinese malaria mosquito (*Anopheles sinensis*) and the like, Chironomidae, Muscidae such as housefly (*Musca domestica*), false stablefly (*Muscina stabulans*) and the like, Calliphoridae, Sarcophagidae, little housefly (*Fannia canicularis*), Anthomyiidae such as seedcorn maggot (*Delia platura*), onion maggot (*Delia antiqua*) and the like, leaf miner flies such as legume leafminer (*Liriomyza trifolii*) and the like, fruit flies, Phoridae, *Drosophila*, moth flies, Simuliidae (blackfly), gadflies, and Culicoides and the like, including, without limitation, Coleopteron insect pests: Corn root worms such as Western corn room worm (*Diabrotica virgifera virgifera*), Southern corn root worm (*Diabroticaundecimpunctata howardi*) and the like, gold beetles such as cupreous chafer (*Anomala cuprea*), soybean beetle (*Anomala rufocuprea*) and the like, weevils such as maize weevil (*Sitophilus zeamais*), ricewater weevil (*Lissorhoptrus oryzophilus*), alfalfa weevil (*Hypera pastica*), adzuki bean weevil (*Callosobruchuys chienensis*) and the like, Tenebrionidae such as yellow mealworm (*Tenebrio molitor*), red flour beetles (*Tribolium castaneum*) and the like, Chrysomilidae such as cucurbit leaf beetle (*Aulacophora femoralis*), striped flea beetle (*Phyllotreta striolata*), Colorado beetle (*Leptinotarsa decemlineata*) and the like, Epilachna such as twenty-eight-spotted ladbirds (*Epilachna vigintioctopunctata*) and the like, Bostrychidae, robe beetle (*Paederus fuscipes*) and the like; Thysanopteran insects, including, without limitation, melon *thrips* (*Thrips palmi*), onion *thrips* (*Thrips tabaci*), flower *thrips* (*Thrips hawaiiensis*), yellow tea *thrips* (*Scirtothrips dorsalis*), flower *thrips* (*Frankliniella intonsa*), western flower *thrips* (*Frankliniella occidentalis*), *Ponticulothrips diospyrosi* and the like; Hymenopteran insects, including, without limitation, ants, hornets, bethylidae, sawflies such as cabbage sawfly (*Athalia japonica*) and the like.

According to one embodiment, the gel formulation of the composition is capable of transferring to an insect body part. According to one embodiment, the gel formulation of the composition is capable of attaching to the surface of an insect body part. According to one embodiment, the gel formulation of the composition is capable of penetrating under a scale of an insect. According to one embodiment, the gel formulation of the composition is glue-like. The term "glue-like" as used herein describes the sticky nature of the formulation that makes it difficult for the insect to remove or dislodge it. According to one embodiment, the gel formulation of the composition is capable of resisting removal. According to one embodiment, the gel formulation of the composition is capable of resisting removal by insect grooming behavior. According to one embodiment, the gel formulation of the composition is capable of being released from the insect body part into a target aqueous body. According to one embodiment, the target aqueous body comprises a contained aqueous body. According to one embodiment, the target aqueous body comprises a contained aqueous body where the insect propagates. According to one embodiment, the release of the gel formulation of the composition from the insect body part to the target aqueous body results in controlling insect larval populations by interrupting insect life cycle. According to one embodiment, the gel formulation of the composition protects the active ingredient from air induced degradation. According to one embodiment, the gel formulation of the composition is contained at the site of application.

According to one embodiment, the gel formulation of the composition comprises an oil based composition of the active ingredient. According to one embodiment, the active ingredient comprises an insecticide. According to one embodiment, the insecticide comprises an insect growth regulator. According to one embodiment, the insect growth regulator comprises pyriproxyfen. According to one embodiment, the insect growth regulator comprises a pyrethroid.

According to one embodiment, the gel formulation of the composition comprises an active ingredient at a concentration at least about 1% to at least about 50% by weight of the composition. According to one embodiment, the gel formulation of the composition comprises an active ingredient at a concentration of at least about 1% by weight of the composition According to one embodiment, the gel formulation of the composition comprises an active ingredient at a concentration of at least about 2.5% by weight of the composition. According to one embodiment, the gel formulation of the composition comprises an active ingredient at a concentration of at least about 5% by weight of the composition. According to one embodiment, the gel formulation of the composition comprises an active ingredient at a concentration of at least about 7.5% by weight of the composition. According to one embodiment, the gel formulation of the composition comprises an active ingredient at a concentration of at least about 10% by weight of the composition. According to one embodiment, the gel formulation of the composition comprises an active ingredient at a concentration of at least about 15% by weight of the composition. According to one embodiment, the gel formulation of the composition comprises an active ingredient at a concentration of at least about 20% by weight of the composition. According to one embodiment, the gel formulation of the composition comprises an active ingredient at a concentration of at least about 25% by weight of the composition. According to one embodiment, the gel formulation of the composition comprises an active ingredient at a concentration of at least about 30% by weight of the composition. According to one embodiment, the gel formulation of the composition comprises an active ingredient at a concentration of at least about 35% by weight of the composition. According to one embodiment, the gel formulation of the composition comprises an active ingredient at a concentration of at least about 40% by weight of the composition. According to one embodiment, the gel formulation of the composition comprises an active ingredient at a concentration of at least about 45% by weight of the composition. According to one embodiment, the gel formulation of the composition comprises an active ingredient at a concentration of at least about 50% by weight of the composition.

Exemplary insecticides that can be incorporated in gel formulations of the present invention are listed in U.S. Pat. No. 4,690,775, the entire contents of which are incorporated herein by reference. Such insecticides include but are not limited to organo-phosphates, such as parathion, malathion, diazinon, dichlorvos, Guthion®, Bidrin®, ronnel and tetraethyl pyrophosphate (TEPP), carbamates such as physostigmine, neostigmine, isolan, dimetann, dimetilan, pyrolan, pyramat, Sevin®, Zectran®, Mesurol® and carbaryl; DDT and related chlorinated diphenyl methanes, ethanes, propanes and butanes; cyclodienes such as chlordane, heptachlor, aldrin, dieldrin, Thiodan®, telodrin, camphene, Toxaphene®, rotenoids such as piperonyl butoxide, sesamin allethrolone; organic fluoride compounds, such as fluoroacetamide derivatives; nicotinoids such as nicotine, anabasine, diparcol, demethyl-cotinine, nicotyrine; hexachlorocyclohexanes such as lindane; chlorinated phenols and naphthols; and 4,6-dinitro-o-cresol and related compounds and like.

According to one embodiment, the gel formulation of the composition further comprises at least one carrier. Carriers can be natural or synthetic. Carriers may include, but are not limited to, hydrocarbons, fatty alcohols or fatty acids, glycerides, esters of fatty acids with C1-C36 alkanols, and a combination thereof. Exemplary hydrocarbons include, but are not limited to, paraffin, petroleum jelly (Vaseline®), etc. Exemplary fatty alcohols include, but are not limited to, decanol, dodecanol, tetradecanol, hexadecanol, or octadecanol. Exemplary fatty acids include, but are not limited to, C6-C24-alkanoic acids, such as hexanoic acid, octanoic acid, decanoic acid, dodecanoic acid, tetradecanoic acid, hexadecanoic acid or octadecanoic acid, and unsaturated fatty acids, e.g. oleic acid, linoleic acid, etc. Exemplary glycerides include, but are not limited to, olive oil, castor oil, corn oil, cottonseed oil, kerosene, mineral oil, peanut oil, sesame oil, soybean oil, hydrogenated oils, capric acid triglyceride, or glycerol mono-, di-, tri-esters with palmitic and/or stearic acid. Further exemplary carriers include, but are not limited to, beeswax, carbowax, carnauba wax, cetyl palmitate, lanolin, isopropyl myristate, isopropyl stearate, oleic acid decyl ester, ethyl oleate. According to one embodiment, the at least one carrier is a stabilizer. According to one embodiment, the at least one carrier comprises petroleum jelly. According to one embodiment, the at least one carrier comprises glycerin.

According to one embodiment, the at least one carrier is at a concentration at least about 1% to at least about 50% by weight of the composition. According to one embodiment, the at least one carrier is at a concentration of at least about 1% by weight of the composition. According to one embodiment, the at least one carrier is at a concentration of at least about 2.5% by weight of the composition. According to one embodiment, the at least one carrier is at a concentration of at least about 5% by weight of the composition. According to one embodiment, the at least one carrier is at a concentration of at least about 7.5% by weight of the composition. According to one embodiment, the at least one carrier is at least about 10% by weight of the composition. According to one embodiment, the at least one carrier is at least about 15% by weight of the composition. According to one embodiment, the at least one carrier is at a concentration of at least about 20% by weight of the composition. According to one embodiment, the at least one carrier is at a concentration of at least about 25% by weight of the composition. According to one embodiment, the at least one carrier is at a concentration of at least about 30% by weight of the composition. According to one embodiment, the at least one carrier is at a concentration of at least about 35% by weight of the composition. According to one embodiment, the at least one carrier is at a concentration of at least about 40% by weight of the composition. According to one embodiment, the at least one carrier is at a concentration of at least about 45% by weight of the composition. According to one embodiment, the at least one carrier is at a concentration of at least about 50% by weight of the composition.

According to one embodiment, the gel formulation of the composition further comprises at least one sticking agent. Exemplary sticking agents may include, but are not limited to, organic oils, inorganic oils, and a combination thereof. Exemplary organic oils include, but are not limited to, olive oil, castor oil, corn oil, cottonseed oil, peanut oil, sesame oil, soybean oil, hydrogenated oil, etc. Exemplary inorganic oils include, but are not limited to, mineral oil, kerosene oil, etc. According to one embodiment, the at least one sticking agent enhances transfer of the gel formulation of the composition to an insect body part. According to one embodiment, the at least one sticking agent comprises corn oil. According to one embodiment, the at least one sticking agent is effective in resisting an insect's attempt to remove the gel formulation of the composition transferred to an insect body part. According to one embodiment, the at least one sticking agent comprises a diluent. According to one embodiment, the at least one sticking agent comprises a stabilizer.

According to one embodiment, the at least one sticking agent is at a concentration at least about 1% to at least about 50% by weight of the composition. According to one embodiment, the at least one sticking agent is at a concentration of at least about 1% by weight of the composition. According to one embodiment, the at least one sticking agent is at a concentration of at least about 2.5% by weight of the composition. According to one embodiment, the at least one sticking agent is at a concentration of at least about 5% by weight of the composition. According to one embodiment, the at least one sticking agent is at a concentration of at least about 7.5% by weight of the composition. According to one embodiment, the at least one sticking agent is at least about 10% by weight of the composition. According to one embodiment, the at least one sticking agent is at least about 15% by weight of the composition. According to one embodiment, the at least one sticking agent is at a concentration of at least about 20% by weight of the composition. According to one embodiment, the at least one sticking agent is at a concentration of at least about 25% by weight of the composition. According to one embodiment, the at least one sticking agent is at a concentration of at least about 30% by weight of the composition. According to one embodiment, the at least one sticking agent is at a concentration of at least about 35% by weight of the composition. According to one embodiment, the at least one sticking agent is at a concentration of at least about 40% by weight of the composition. According to one embodiment, the at least one sticking agent is at a concentration of at least about 45% by weight of the composition. According to one embodiment, the at least one sticking agent is at a concentration of at least about 50% by weight of the composition.

According to one embodiment, the gel formulation of the composition further comprises at least one emulsifying agent. Exemplary emulsifying agents include, but are not limited to, non-ionic emulsifying agents, anionic emulsifying agents and cationic emulsifying agents. Exemplary non-ionic emulsifying agents include, but are not limited to, phenylethyl phenol polyoxyethylene ether, alkylphenyol ethoxylates, Tween-80®, Triton-X, sodium dodecyl sulfate, polyoxyethylated alkylphenols (e.g., octylphenol and nonylphenol), polyoxyethylated sorbitan monoesters, polyoxyethylated fatty or aryl-alkyl alcohols and fatty acids (the latter including esters of polyethylene glycol). Exemplary anionic emulsifying agents include, but are not limited to, calcium dodecyl benzenosulfonate, sodium alkyl, alkyl-aryl and aryl sulfonates, sulfates and phosphates, soaps (i.e., salts of carboxylic acids with at least 8 carbon atoms).

Exemplary cationic emulsifying agents include, but are not limited to, quaternary ammonium salts and salts of primary, secondary and tertiary amines containing at least one hydrocarbon moiety with 8 or more carbon atoms. Common emulsifying agents are described in, among other publications, in Rosen, Surfactants and Interfacial Phenomena, pp. 5-25, John Wiley & Sons (1978), the contents of which are hereby incorporated herein by reference. According to one embodiment, the at least one emulsifying agent comprises a surfactant. According to one embodiment, the at least one emulsifying agent comprises a commercially available emulsifier.

Exemplary emulsifying agents further include but not limited to Sparkleen® detergent, Omega® emulsifier blend, and a combination thereof. According to one embodiment, the emulsifying agent is at a concentration at least about 1% to about 50% by weight of the composition. According to one embodiment, the emulsifying agent is at a concentration of at least about 1% by weight of the composition. According to one embodiment, the emulsifying agent is at a concentration of at least about 2.5% by weight of the composition. According to one embodiment, the emulsifying agent is at a concentration of at least about 5% by weight of the composition. According to one embodiment, the emulsifying agent is at a concentration of at least about 7.5% by weight of the composition. According to one embodiment, the emulsifying agent is at least about 10% by weight of the composition. According to one embodiment, the emulsifying agent is at least about 15% by weight of the composition. According to one embodiment, the emulsifying agent is at a concentration of at least about 20% by weight of the composition. According to one embodiment, the emulsifying agent is at a concentration of at least about 25% by weight of the composition. According to one embodiment, the emulsifying agent is at a concentration of at least about 30% by weight of the composition. According to one embodiment, the emulsifying agent is at a concentration of at least about 35% by weight of the composition. According to one embodiment, the emulsifying agent is at a concentration of at least about 40% by weight of the composition. According to one embodiment, the emulsifying agent is at a concentration of at least about 45% by weight of the composition. According to one embodiment, the emulsifying agent is at a concentration of at least about 50% by weight of the composition.

According to one embodiment, the surfactant is at a concentration at least about 1% to about 50% by weight of the composition. According to one embodiment, the surfactant is at a concentration of at least about 1% by weight of the composition. According to one embodiment, the surfactant is at a concentration of at least about 2.5% by weight of the composition. According to one embodiment, the surfactant is at a concentration of at least about 5% by weight of the composition. According to one embodiment, the surfactant is at a concentration of at least about 7.5% by weight of the composition. According to one embodiment, the surfactant is at least about 10% by weight of the composition. According to one embodiment, the surfactant is at least about 15% by weight of the composition. According to one embodiment, the surfactant is at a concentration of at least about 20% by weight of the composition. According to one embodiment, the surfactant is at a concentration of at least about 25% by weight of the composition. According to one embodiment, the surfactant is at a concentration of at least about 30% by weight of the composition. According to one embodiment, the surfactant is at a concentration of at least about 35% by weight of the composition. According to one embodiment, the surfactant is at a concentration of at least about 40% by weight of the composition. According to one embodiment, the surfactant is at a concentration of at least about 45% by weight of the composition. According to one embodiment, the surfactant is at a concentration of at least about 50% by weight of the composition.

According to one embodiment, the at least one emulsifying agent is effective in releasing the gel formulation of the composition into a target aqueous body upon contact with such and causing an immediate dispersal of the gel formulation of the composition in the target aqueous body. According to one embodiment, the at least one surfactant is effective in releasing the gel formulation of the composition into a target aqueous body and causing an immediate dispersal of the gel formulation of the composition in the target aqueous body.

According to one embodiment, the gel formulation of the composition further comprises at least one particulate ingredient. Exemplary particulate ingredients include, but are not limited to, clay powder, silica powder, talc powder, and a combination thereof.

According to one embodiment, the at least one particulate ingredient is at a concentration at least about 1% to about 50% by weight of the composition. According to one embodiment, the at least one particulate ingredient is at a concentration of at least about 1% by weight of the composition. According to one embodiment, the at least one particulate ingredient is at a concentration of at least about 2.5% by weight of the composition. According to one embodiment, the at least one particulate ingredient is at a concentration of at least about 5% by weight of the composition. According to one embodiment, the at least one particulate ingredient is at a concentration of at least about 7.5% by weight of the composition. According to one embodiment, the at least one particulate ingredient is at least about 10% by weight of the composition. According to one embodiment, the at least one particulate ingredient is at least about 15% by weight of the composition. According to one embodiment, the at least one particulate ingredient is at a concentration of at least about 20% by weight of the composition. According to one embodiment, the at least one particulate ingredient is at a concentration of at least about 25% by weight of the composition. According to one embodiment, the at least one particulate ingredient is at a concentration of at least about 30% by weight of the composition. According to one embodiment, the at least one particulate ingredient is at a concentration of at least about 35% by weight of the composition. According to one embodiment, the at least one particulate ingredient is at a concentration of at least about 40% by weight of the composition. According to one embodiment, the at least one particulate ingredient is at a concentration of at least about 45% by weight of the composition. According to one embodiment, the at least one particulate ingredient is at a concentration of at least about 50% by weight of the composition.

According to one embodiment, the gel formulation of the composition is prepared by initially dissolving the at least one active ingredient in a solvent. Exemplary organic solvents include, but are not limited to, acetone, dimethylsulfoxide (DMSO), dimethyl formamide (DMF), allantoin, urazole, N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. According to one embodiment, the solvent is evaporated off. According to one embodiment, the solvent comprises an organic solvent. According to one embodiment, the solvent comprises an aqueous solvent.

According to one embodiment, the gel formulation of the composition has a viscosity of at least about 50 centipoise, to at least about 70 centipoise upon preparation. According to one embodiment, the gel formulation of the composition has a viscosity of at least about 50 centipoise to at least about 250,000 centipoise after a period of time. According to one embodiment, the period of time is between at least about one month to at least about six months.

According to one embodiment, the gel formulation of the composition has a viscosity of at least about 50 centipoise upon preparation. According to one embodiment, the gel formulation of the composition has a viscosity of at least about 55 centipoise upon preparation. According to one embodiment, the gel formulation of the composition has a viscosity of at least about 60 centipoise upon preparation. According to one embodiment, the gel formulation of the composition has a viscosity of at least about 65 centipoise upon preparation. According to one embodiment, the gel formulation of the composition has a viscosity of at least about 70 centipoise upon preparation.

According to one embodiment, the gel formulation of the composition has a viscosity of at least about 50 centipoise after a period of time. According to one embodiment, the gel formulation of the composition has a viscosity of at least about 60 centipoise after a period of time. According to one embodiment, the gel formulation of the composition has a viscosity of at least about 70 centipoise after a period of time. According to one embodiment, the gel formulation of the composition has a viscosity of at least about 80 centipoise after a period of time. According to one embodiment, the gel formulation of the composition has a viscosity of at least about 90 centipoise after a period of time. According to one embodiment, the gel formulation of the composition has a viscosity of at least about 100 centipoise after a period of time. According to one embodiment, the gel formulation of the composition has a viscosity of at least about 250 centipoise after a period of time. According to one embodiment, the gel formulation of the composition has a viscosity of at least about 500 centipoise after a period of time. According to one embodiment, the gel formulation of the composition has a viscosity of at least about 1,000 centipoise after a period of time. According to one embodiment, the gel formulation of the composition has a viscosity of at least about 10,000 centipoise after a period of time. According to one embodiment, the gel formulation of the composition has a viscosity of at least about 20,000 centipoise after a period of time. According to one embodiment, the gel formulation of the composition has a viscosity of at least about 30,000 centipoise after a period of time. According to one embodiment, the gel formulation of the composition has a viscosity of at least about 40,000 centipoise after a period of time. According to one embodiment, the gel formulation of the composition has a viscosity of at least about 50,000 centipoise after a period of time. According to one embodiment, the gel formulation of the composition has a viscosity of at least about 60,000 centipoise after a period of time. According to one embodiment, the gel formulation of the composition has a viscosity of at least about 70,000 centipoise after a period of time. According to one embodiment, the gel formulation of the composition has a viscosity of at least about 80,000 centipoise after a period of time. According to one embodiment, the gel formulation of the composition has a viscosity of at least about 90,000 centipoise after a period of time. According to one embodiment, the gel formulation of the composition has a viscosity of at least about 100,000 centipoise after a period of time. According to one embodiment, the gel formulation of the composition has a viscosity of at least about 125,000 centipoise after a period of time. According to one embodiment, the gel formulation of the composition has a viscosity of at least about 150,000 centipoise after a period of time. According to one embodiment, the gel formulation of the composition has a viscosity of at least about 175,000 centipoise after a period of time. According to one embodiment, the gel formulation of the composition has a viscosity of at least about 200,000 centipoise after a period of time. According to one embodiment, the gel formulation of the composition has a viscosity of at least about 225,000 centipoise after a period of time. According to one embodiment, the gel formulation of the composition has a viscosity of at least about 250,000 centipoise after a period of time.

According to one embodiment, the period of time is at least about one month. According to one embodiment, the period of time is at least about two months. According to one embodiment, the period of time is at least about three months. According to one embodiment, the period of time is at least about four months. According to one embodiment, the period of time is at least about five months. According to one embodiment, the period of time is at least about six months.

According to one embodiment, the described invention provides a gel formulation of the composition that topically contaminates an oviposition-seeking insect. As used herein, the terms "topical" and "topically" are used interchangeably to refer to delivery of an insect growth regulator onto one or more surfaces of an insect's body part, including epithelial surfaces. According to one embodiment, the described invention provides a gel formulation of the composition that topically contaminates a mating insect. According to one embodiment, the described invention provides a gel formulation of the composition that topically contaminates an insect engaged in aggregation behavior. According to one embodiment, the insect comprises an insect engaged in feeding. According to one embodiment, the insect comprises an insect engaged in overwintering. According to one embodiment, the insect comprises an insect engaged in foraging.

The mode of application of the gel formulation of the composition will depend on the type of the insect. According to one embodiment, the gel formulation of the composition is applied on an applicator that attracts the insect. According to one embodiment, the applicator is a mesh. According to one embodiment, the mesh is placed within a container.

According to one embodiment, the applicator is placed within an autodissemination apparatus. According to one embodiment, the applicator is placed within an insect trap. According to one embodiment, the insect trap is a container. According to one embodiment, the applicator is a sheet. According to one embodiment, the applicator is a cup. According to one embodiment, the applicator is a film.

According to one embodiment, the autodissemination apparatus comprises: (1) a cap component, wherein the cap component comprises (i) a plurality of openings, and (ii) a plurality of auto-filling holes; (2) a cup component, wherein the cup component comprises (i) a water absorbing gel; (ii) a plurality of overflow protection holes, and (iii) a weighted base; (3) a mesh component. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the autodissemination apparatus comprises: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component. According to one embodiment, the cap component comprises at least three portal arms. According to some such embodiments, the mesh component is coated with the gel formulation of the composition comprising at least one ingredient. According to one embodiment, the mesh component is the primary platform for transfer of the gel formulation of the composition comprising at least one ingredient to an insect. According to one embodiment, the reservoir component further comprises a bag containing an insect attractant. According to one embodiment, the reservoir component optionally comprises a water absorbing gel.

According to one embodiment, the autodissemination apparatus comprises: (1) a cap component, wherein the cap component comprises (i) a transfer chamber; (ii) at least one horizontal entrance opening; (iii) a plurality of vertical window openings; (iv) a plurality of window shields, wherein each window shield is coated on its inner surface with the gel formulation, covers a vertical window opening and contains an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component. According to some such embodiments, the horizontal entrance opening is located on the top of the cap component. According to some such embodiments, the horizontal entrance opening has a circumference smaller than the circumference of the base of the cup component. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings. According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

Exemplary autodissemination apparati that can be used for applying the gel formulations of the present invention include, but are not limited to, autodissemination devices, insect traps, insect feeding stations, insect contamination chambers, insect bait stations, etc, such as disclosed in U.S. Pat. No. 5,452,540, U.S. Pat. No. 5,359,807, U.S. Pat. No. 4,671,010, U.S. Pat. No. 5,042,194, U.S. Pat. No. 4,485,582, U.S. Pat. No. 5,057,315, U.S. Pat. No. 5,057,316, U.S. Pat. No. 5,189,831, U.S. Pat. No. Des. 324,406, and U.S. Pat. No. 5,238,681, the entire contents of which are incorporated herein by reference. A skilled artisan would appreciate that such exemplary autodissemination apparatus can be modified for the application of the gel formulation of the composition of the present invention.

According to one embodiment, the described invention provides a gel formulation of the composition comprising at least one active ingredient that is released from an insect body part into a target aqueous body where the insect propagates. According to one embodiment, the release is immediate. According to one embodiment, the release is followed by immediate dispersal of the gel formulation of the composition in the target aqueous body where the insect propagates. According to one embodiment, the release results in controlling the insect larval population by interrupting the insect life cycle. According to one embodiment, the at least one active ingredient comprises an insecticide. According to one embodiment, the target aqueous body comprises a water holding container. According to one embodiment, the target aqueous body comprises a larval habitat.

According to one embodiment, the at least one active ingredient is present at a concentration that is effective in causing a biological effect, e.g., preventing larvae from developing into adulthood. According to another embodiment, the at least one active ingredient is present at a concentration effective to cause killing of at least 60%, at least 65%, at least 70%, at least 75%, at least 80%, at least 85%, at least 90%, at least 95%, at least 96%, at least 97%, at least 98% o, at least 99% or 100% of the larval population in the target aqueous body by release from a single contaminated gravid female insect. According to another embodiment, the at least one active ingredient is present at a concentration effective to cause killing of at least 60% of the larval population in the target aqueous body by release from a single contaminated gravid female insect. According to another embodiment, the at least one active ingredient is present at a concentration effective to cause killing of at least 65% of the larval population in the target aqueous body by release from a single contaminated gravid female insect. According to another embodiment, the at least one active ingredient is present at a concentration effective to cause killing of at least 70% of the larval population in the target aqueous body by release from a single contaminated gravid female insect. According to another embodiment, the at least one active ingredient is present at a concentration effective to cause killing of at least 75% of the larval population in the target aqueous body by release from a single contaminated gravid female insect. According to another embodiment, the at least one active ingredient is present at a concentration effective to cause killing of at least 80% of the larval population in the target aqueous body by release from a single contaminated gravid female insect. According to another embodiment, the at least one active ingredient is present at a concentration effective to cause killing of at least 85% of the larval population in the target aqueous body by release from a single contaminated gravid female insect. According to another embodiment, the at least one active ingredient is present at a concentration effective to cause killing of at least 90% of the larval population in the target aqueous body by release from a single contaminated gravid female insect. According to another embodiment, the at least one active ingredient is present at a concentration effective to cause killing of at least 95% of the larval population in the target aqueous body by release from a single contaminated gravid female insect. According to another embodiment, the at least one active ingredient is present at a concentration effective to cause killing of at least 96% of the larval population in the target aqueous body by release from a single contaminated gravid female insect. According to another embodiment, the at least one active ingredient is present at a concentration effective to cause killing of at least 97% of the larval population in the target aqueous body by release from a single contaminated gravid female insect. According to another embodiment, the at least one active ingredient is present at a concentration effective to cause killing of at least 98% of the larval population in the target aqueous body by release from a single contaminated gravid female insect. According to another embodiment, the at least one active ingredient is present at a concentration effective to cause killing of at least 99% of the larval population in the target aqueous body by release from a single contaminated gravid female insect.

According to one embodiment, the target aqueous body holds from about 10 ml to about 2 gallons of water. According to one embodiment, the target aqueous body holds about 10 ml of water. According to one embodiment, the target aqueous body holds about 50 ml of water. According to one embodiment, the target aqueous body holds about 100 ml of water. According to one embodiment, the target aqueous body holds about 250 ml of water. According to one embodiment, the target aqueous body holds about 500 ml of water. According to one embodiment, the target aqueous body holds about 750 ml of water. According to one embodiment, the target aqueous body holds about 1 liter of water. According to one embodiment, the target aqueous body holds about 2 liters of water. According to one embodiment, the target aqueous body holds about 3 liters of water. According to one embodiment, the target aqueous body holds about 3.5 liters of water. According to one embodiment, the target aqueous body holds about 0.5 gallon of water. According to one embodiment, the target aqueous body holds about 1 gallon of water. According to one embodiment, the target aqueous body holds about 1.5 gallons of water. According to one embodiment, the target aqueous body holds about 2 gallons of water.

A skilled artisan would appreciate that a single autodissemination apparatus of the present invention can contaminate a plurality of gravid female insects visiting the apparatus. Similarly, a plurality of the autodissemination apparati dispersed in a given location can contaminate multiples of the plurality of gravid female insects visiting the apparati. It follows that a plurality of contaminated gravid female insects would cause killing of the larval population in larger target aqueous bodies. All of the above embodiments are included within the scope of the claimed invention.

Autodissemination Apparatus

According to another aspect, the described invention provides an autodissemination apparatus to topically contaminate an insect, the autodissemination apparatus comprising at least three main components: (1) a bottom cup component, (2) an upper cap component, and (3) a mesh component.

Such insects include, but are not limited to, mosquitoes, grasshoppers, true bugs, flies, fleas, bees, wasps, ants, lice, moths, and beetles, or any member of *Arthropoda*. According to one embodiment, the insect population comprises a peridomestic insect population. According to one embodiment, the insect comprises an oviposition-seeking insect. According to one embodiment, the insect comprises a mating insect. According to one embodiment, the insect comprises an insect seeking aggregation behavior. According to one embodiment, the insect comprises an insect engaged in feeding. According to one embodiment, the insect comprises an insect engaged in overwintering. According to one embodiment, the insect comprises an insect engaged in foraging.

Nonlimiting examples of an insect to which the apparatus of the present invention is applicable include the following: Hemiptera insects, including, without limitation, planthoppers such as small brown planthopper (*Laodelphax striatellus*), brown planthopper (*Nilaparvata lugens*), white-backed rice planthopper (*Sogatella furcifera*) and the like, leafhoppers such as green rice leafhopper (*Nephotettix cincticeps*), Taiwan green rice leafhopper (*Nephotettix virescens*) and the like, aphides such as cotton aphid (*Aphis gossypii*), green peach aphid (*Myzus persicae*), apple aphid (*Aphis citricola*), turnip aphid (*Lipaphis pserudobrassicae*), pear grean aphid (*Nippolachnus phi*), black citrus aphid (*Toxoptera aurantil*), tropical citrus aphid (*Toxoptera ciidius*) and the like, stink bugs such as green stink bug (*Nezara antennata*), *Cletus punctiger*, bean bug (*Riptortus clavetus*), brownwinged green bug (*Plautia stali*) and the like, whiteflies such as greenhouse whitefly (*Trialeurodes vaporariorum*), sweetpotato whitefy (*Bemisia tabaci*), silverleaf whitefly (*Bemisia argentifolii*) and the like, scale insects such as California red scale (*Aonidiella aurantii*), San Jose scale (*Comstockaspis perniciosa*), citrus snow scale (*Unaspis citri*), white peach scale (*Pseudaulacaspis pentagona*), brown olive scale (*Saissetia oleae*), purple scale (*Lepidosaphes beckii*), red wax scale (*Ceroplastes rubens*), cottonycushion scale (*Icerya purchasi*) and the like, lace bugs, jumping plant louses and the like; Lepidopteran insects, including, without limitation, Pyralidae such as rice stem borer (*Chilo suppressalis*), rice leafroller (*Cnaphalocrocis medinalis*), European corn borer (*Ostrinia nubilalis*), cabbage webworm (*Hellulla undalis*), bluegrass webworm (*Parapediasia teterrella*), cotton leafroller (*Notarch derogata*), Indian meal moth (*Plodia interpuncterlla*) and the like, Noctuidae such as tabaco cutworm (*Spodoptera litura*), rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and the like, Pieridae such as small white (*Pieris rapae*) and the like, Tortricidae such as *Adoxophyes* spp., oriental fruit moth (*Grapholita molesta*), codling moth (*Cydia pomonella*) and the like, Carposinidae such as peach fruit moth (*Carposina niponensis*) and the like, Lyonetiidae such as *Lyonetia* spp. and the like, Lymantriidae such as *Lymantria* spp., *Euproctis* spp. and the like, Yponomeutidae such as diamondback moth (*Plutela xylostella*) and the like, Gelechiidae such as pink ball worm (*Pectinophora gossypiella*) and the like, Arctiidae such as fall webworm (*Hyphantria cunea*) and the like, Tineidae such as casemaking clothes moth (*Tinea translucens*), webbing clothes moth (*Tineola bisselliella*) and the like; *Diptera* insects, including, without limitation, *Culex* spp; such as common mosquito (*Culex pipiens pallens*), oriental latrine fly (*Culex tritaeniorhynchus*) and the like, *Aedes* spp. such as dengue mosquito (*Aedes aegypti*), tiger mosquito (*Aedes albopictus*) and the like, *Anopheles* spp. such as Chinese malaria mosquito (*Anopheles sinensis*) and the like, Chironomidae, Muscidae such as housefly (*Musca domestica*), false stablefly (*Muscina stabulans*) and the like, Calliphoridae, Sarcophagidae, little housefly (*Fannia canicularis*), Anthomyiidae such as seedcorn maggot (*Delia platura*), onion maggot (*Delia antiqua*) and the like, leaf miner flies such as legume leafminer (*Liriomyza trifolii*) and the like, fruit flies, Phoridae, *Drosophila*, moth flies, Simuliidae (blackfly), gadflies, and Culicoides and the like, including, without limitation, Coleopteron insect pests: Corn root worms such as Western corn room worm (*Diabrotica virgifera virgifera*), Southern corn root worm (*Diabrotica undecimpunctata howardi*) and the like, gold beetles such as cupreous chafer (*Anomala cuprea*), soybean beetle (*Anomala rufocuprea*) and the like, weevils such as maize weevil (*Sitophilus zeamais*), ricewater weevil (*Lissorhoptrus oryzophilus*), alfalfa weevil (*Hypera pastica*), adzuki bean weevil (*Callosobruchuys chienensis*) and the like, Tenebrionidae such as yellow mealworm (*Tenebrio molitor*), red flour beetles (*Tribolium castaneum*) and the like, Chrysomilidae such as cucurbit leaf beetle (*Aulacophora femoralis*), striped flea beetle (*Phyllotreta striolata*), Colorado beetle (*Leptinotarsa decemlineata*) and the like, *Epilachna* such as twenty-eight-spotted ladbirds (*Epilachna vigintioctopunctata*) and the like, Bostrychidae, robe beetle (*Paederus fuscipes*) and the like; Thysanopteran insects, including, without limitation, melon *thrips* (*Thrips palmi*), onion *thrips* (*Thrips tabaci*), flower *thrips* (*Thrips hawaiiensis*), yellow tea *thrips* (*Scirtothrips dorsalis*), flower *thrips* (*Frankliniella intonsa*), western flower *thrips* (*Frankliniella occidentalis*), *Ponticulothrips diospyrosi* and the like; Hymenopteran insects, including, without limitation, ants, hornets, bethylidae, sawflies such as cabbage sawfly (*Athalia japonica*) and the like.

The described apparatus (1) once deployed into the field, requires no further effort over an insect season. The unit's water reservoir can initially be filled with oak infusion water if desired, but thereafter it will be auto-filled with rainwater. The water absorbent gel will slow evaporative loss and thereby assist the unit in bridging periods of low rainfall. The unit is designed to attract gravid females but to prevent oviposition in the station, so there are no oviposition papers to replace as they fill with eggs. The toxicant will not have to be refreshed since it shows outstanding persistence under normal conditions and will be protected from water, sunlight and microbial action within the unit; (2) Low cost: It is vital for the station to be inexpensive so sufficient units can be deployed to compete with natural oviposition sites; (3) Biodegradable: The station is intended for a single season of use. All components are designed to thereafter disintegrate into the soil, eliminating the necessity of post-season cleanup or for the unit to become a source for mosquito production once its toxicant is depleted; (4) High attraction: the station is as attractive as possible for gravid females. The unit can resemble a treehole in texture and color (dark brown to black), is provisioned with a substrate for bacterial growth, and has a water reservoir; (4) Extended attraction: The effective life of the unit depends on maintaining moisture for the greatest possible duration. Thus, the water reservoir is designed to be renewed via rainwater collection, while also allowing overflow. The noncoated inner cap surface will encourage high humidity (and resting behavior) as well as better insect-growth regulator (for example, but not limited to, pyriproxyfen) loading onto this surface; (6) High toxicant loading: The curved shapes of the mesh and inner cup surface provide increased surface area for insect-growth regulator (for example, but not limited to, pyriproxifen) loading. Further, the mesh component (for example, but not limited to, a cotton fabric mesh) will be pre-washed to induce 'fraying', that is unraveling of fibers, significantly increasing the surface area available for toxicant loading. Transfer to females is augmented with a sticker adjuvant; (7) Extended search time: Intercepting gravid females, such as, for example, but not limited to, gravid mosquitoes, grasshoppers, true bugs, flies, fleas, bees, wasps, ants, lice, moths, and beetles, or any member of *Arthropoda*, on the mesh will exploit their search behavior (i.e., crawling over the mesh attempting to locate an opening to the water below), increasing insect-growth regulator (for example, but not limited to, pyriproxifen) transfer. That is, extending search time will increase toxicant transfer to the mosquito; (8) Exclusion from oviposition: Unable to reach the water reservoir, attracted females will retain eggs that otherwise would have been deposited in the autodissemination station. Thus, they will need to visit additional larval habitats generating more transfer events; (9) Extended toxicant activity: The unit buffers the insecticide from premature environmental extremes including UV light exposure and rain, preserving its activity all season, thereby increasing its already excellent persistence; and (10) Safe: As an insect-growth regulator, pyriproxifen is virtually nontoxic to birds and mammals. Nevertheless, containing the chemical within the sealed unit bars livestock, pets, and wildlife from access. More significantly, the 'bait' approach inherent to autodissemination is precisely targeted and therefore environmentally-friendly than the broadcast spray of adulticides normally used by animal producers.

I. Cup Component

According to one embodiment, the cup component comprises a water reservoir to attract gravid females. According to one embodiment, the cup base is rounded and weighted with embedded sand or other dense material to assist the unit in maintaining a stable, upright position.

According to another embodiment, the cup component is constructed by molding an optionally biodegradable material with a binder. According to some embodiments, the cup component is constructed by molding an optionally biodegradable material with a binder, wherein the optionally biodegradable material is wet shredded cardboard. According to some embodiments, the biodegradable material is a pasteboard. According to some embodiments, the cup component is constructed by molding an optionally biodegradable material with a binder, wherein the optionally biodegradable materials is a cellulose-based material. Binders include, but are not limited to, a corn starch, peat moss, an egg carton, rice hulls, a newspaper, straw, a natural polymer(s), or other materials or combinations thereof. According to some embodiments, the binder is a water-soluble binder. According to some embodiments, the optionally biodegradable material comprises wet shredded cardboard. According to some embodiments, the optionally biodegradable material comprises a pasteboard. According to some embodiments, the optionally biodegradable material comprises a cellulose-based material.

According to some embodiments, the cup also holds an organic substrate (for example, but not limited to, dried shredded oak leaves, yeast, etc.) for bacteria that produce volatile cues that gravid female container species use in selecting oviposition sites. (See, for example, Ponnusamy et al, Microb Ecol. 2008 November; 56(4):593-603, 2008, the contents of which are incorporated by reference herein in their entirety). For example, a few granules of a saponified starch-graft polyacrylonitrile copolymer are placed in the cup. Upon contact with water, this material swells into a gel, absorbing hundreds of times its own weight in moisture. Thus, the gel can assist in conserving water and thereby extend the duration of insect attraction to the station.

According to another embodiment, the cup component further comprises a plurality of overflow protection holes. According to one embodiment, the overflow protection holes are located at points above the water reservoir which allow for overflow water to escape from the apparatus, if required. The plurality of overflow protection holes in the cup component keeps the reservoir level from reaching the mesh component and adhering toxicant.

According to some embodiments, the cup component is coated with a water proofing agent, such as, for example, but not limited to, paraffin wax, to water proof and extend the life of the apparatus.

According to some embodiments, the cup component further comprises a base component, providing a weight-supported base of the cup component that assist with positional stability of the apparatus.

According to one embodiment, the cup component comprises a reservoir component. According to one embodiment, the reservoir component comprises a volume of water. According to one embodiment, the volume of water is between at least about 1 ml to at least about 1 liter. According to one embodiment, the volume of water is at least about 1 ml. According to one embodiment, the volume of water is at least about 5 ml. According to one embodiment, the volume of water is at least about 10 ml. According to one embodiment, the volume of water is at least about 25 ml. According to one embodiment, the volume of water is at least about 50 ml. According to one embodiment, the volume of water is at least about 100 ml. According to one embodiment, the volume of water is at least about 250 ml. According to one embodiment, the volume of water is at least about 500 ml. According to one embodiment, the volume of water is at least about 600 ml. According to one embodiment, the volume of water is at least about 700 ml. According to one embodiment, the volume of water is at least about 800 ml. According to one embodiment, the volume of water is at least about 900 ml. According to one embodiment, the volume of water is at least about 1 liter.

A skilled artisan would appreciate that the water could be replaced with aqueous solutions of sweetening agents that would attract gravid female insects to the autodissemination apparatus. Exemplary sweetening agents include but are not limited to sucrose, glucose, fructose and the like.

II. Cap Component

According to one embodiment, the cap component comprises a transfer chamber. According to one embodiment, the cap component comprises a base that is designed to friction-fit within the upper-most portion of the cup component where the two components are secured with adhesive. According to one embodiment, the cap component base is slightly smaller in diameter than the cup component and slips several millimeters into the cup component to create a shallow gutter or a trough between the cup component and the cap component. According to one embodiment, the gutter captures rainwater running off the cap component and directs it into the cup component reservoir via small auto-fill holes, keeping the unit functional (i.e., attractive to mosquitoes) for a greater duration.

According to one embodiment, the cap component further contains a plurality of openings. According to some such embodiments, the opening is an entrance opening, which allows entry of an insect into the cap component. According to some such embodiments, the opening is an exit opening, which allows exit of an insect from the cap component. According to some embodiments, the opening is an entry or an exit opening, which allows entry or exit of an insect into or from the cap component at points above the mesh component. According to some embodiments, the opening comprises a portal located on an arm. According to some such embodiment, the portal arm is an entry or exit arm allowing entry or exit of an insect into or from the cap component. According to one embodiment, the cap component comprises at least one portal arm. According to one embodiment, the cap component comprises at least three portal arms.

According to another embodiment, the opening is a horizontal opening. According to some such embodiments, the horizontal opening is an entrance opening. According to some such embodiments, the horizontal entrance opening is located on the top of the cap component. According to some such embodiments, the horizontal entrance opening has a circumference smaller than the circumference of the base of the cup component. According to some embodiments, the opening is a vertical window opening. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings.

According to one embodiment, the cap component further comprises a unidirectional mesh funnel. According to some such embodiments, the unidirectional mesh funnel is made from cotton fabric mesh material. According to one embodiment, the unidirectional mesh funnel prevents an insect seeking water to reach the water reservoir contained within the cup component.

According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

According to one embodiment, the cap component further contains a plurality of auto-filling holes that are at points below the mesh component. According to one embodiment, the cap component is mated to a cup component. According to one embodiment, the cap component has a slightly smaller diameter than the cup component. According to some such embodiments, when the cap component that has a slightly smaller diameter than the cup component and the cup component are mated, a trough is formed between the cap component and the cup component. According to one embodiment, the trough allows for collection of rainwater that then can enter the cup component through the plurality of auto-filling holes in the cap component.

According to one embodiment of the autodissemination apparatus, the water that enters the cup component associates with a water absorbing gel, such as, for example, a saponified starch-graft polyacrylonitrile copolymer. Upon contact with water, this material swells into a water absorbed gel, absorbing hundreds of times its own weight in moisture. Thus, the water absorbed gel can assist in conserving water and thereby extend the duration of mosquito attraction to the station.

According to some embodiments, the cap component is constructed by molding an optionally biodegradable material with a binder, wherein the optionally biodegradable material is wet shredded cardboard. According to some embodiments, the biodegradable material is a pasteboard. According to some embodiments, the optionally biodegradable material comprises wet shredded cardboard. According to some embodiments, the optionally biodegradable material comprises a pasteboard. According to some embodiments, the optionally biodegradable material comprises a cellulose-based material. According to some embodiments, the cap component is constructed by molding an optionally biodegradable material with a binder, wherein the optionally biodegradable materials is a cellulose-based material. Exemplary binders include, but are not limited to, a corn starch, peat moss, an egg carton, rice hulls, a newspaper, straw, a natural polymer(s), or other materials or combinations thereof. According to some embodiments, the binder is a water-soluble binder.

According to some embodiments, the cap component is coated with a waterproofing agent, such as, for example, but not limited to, paraffin wax, to water proof and extend the life of the apparatus. According to some embodiments, the upper four-fifths (⅘ths) of the cap components' inner surface is not wax coated to aid in maintaining a high humidity that helps reduce the rate of moisture loss from the reservoir. According to some embodiments, the cap component comprises an attractive surface to resting mosquitoes. According to some such embodiments, this surface serves as a secondary platform for toxicant transfer. According to some such embodiments, the attractive surface to resting mosquitoes is coated with an insect-growth regulator. Such an insect-growth regulator includes, but is not limited to, pyriproxyfen.

According to one embodiment, an autodissemination apparatus comprises a cap component which encloses a mesh component.

III. Mesh Component

The third component of the apparatus is a mesh component. According to one embodiment, the mesh component is a cotton fabric mesh. According to another embodiment, the mesh component is fashioned into a cone and secured within the cap component. According to one embodiment, the mesh component is coated with the gel formulation of the composition comprising at least one active ingredient. According to one embodiment, the mesh component is the primary platform for the transfer of the gel formulation of the composition comprising at least one active ingredient to an insect.

According to another embodiment, the mesh component serves as a barrier that prevents insects, such as, for example, but not limited to, mosquitoes, grasshoppers, true bugs, flies, fleas, bees, wasps, ants, lice, moths, and beetles, or any member of *Arthropoda*, from entering the cup to oviposit. According to some embodiments, the overflow and auto-fill holes of the mesh component are sized to be too small to permit passage to the cup component reservoir. According to some embodiments, the mesh component serves as a barrier that induces searching behavior by female insects, such as, but not limited, to mosquitoes, grasshoppers, true bugs, flies, fleas, bees, wasps, ants, lice, moths, and beetles, or any member of *Arthropoda*, attempting to locate the water, thereby maximizing visit time, female insect contact with the mesh component, and toxicant transfer.

The goal is to induce the insect to become loaded with sufficient active ingredient to effectively transfer the toxicant to alternative oviposition sites. Without being limited by theory, the frustration caused to the female insect, such as, for example, mosquitoes, by their inability to oviposit in the apparatus leads the female mosquitoes to visit additional proximal larval habitats (water-holding containers). Furthermore, because oviposition is inhibited, the apparatus does not reach a threshold of egg deposition that otherwise deters attraction.

According to another embodiment, the mesh component is cone shaped. According to some such embodiments, the cone shape of the mesh provides additional surface area for the insect-growth regulator loading and insect searching, as well as reducing prospects of insects exiting without contacting the mesh component. Such insect-growth regulators include, for example, but not limited to, pyriproxyfen. According to another embodiment, the insect-growth regulator is present in an amount effective to cause a biological effect, e.g., preventing larval development into adulthood.

According to one embodiment, the described invention provides an autodissemination apparatus to topically inoculate an insect, the apparatus comprising: (1) a cap component, wherein the cap component comprises (i) a plurality of openings, and (ii) a plurality of auto-filling holes; (2) a cup component, wherein the cup component comprises (i) a water absorbing gel; (ii) a plurality of overflow protection holes, and (iii) a weighted base; (3) a mesh component. According to one embodiment, the autodissemination apparatus further comprises (4) a gel formulation of a composition for management of insect populations, the gel formulation of the composition comprising at least one active ingredient for management of insect populations. According to one embodiment, the described invention provides an autodissemination apparatus of FIG. 1, the apparatus comprising: a cap component [1]; a pyriproxyfen-coated mesh component [2]; at least one entrance [3]; a trough [4]; a plurality of auto-filling holes [5]; a plurality of overflow protection holes [6]; a cup component [7]; a water reservoir [8]; a water absorbing gel [9]; and a weight-supported base component [10]. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component. According to one embodiment, the autodissemination apparatus further comprises (4) a gel formulation of a composition for management of insect populations, the gel formulation of the composition comprising at least one active ingredient for management of insect populations. According to another embodiment, the described invention provides an autodissemination apparatus of FIG. 2, the apparatus comprising: a transfer chamber [11]; a plurality of portal arms [12a], each containing an opening or portal for entry or exit [12b]; a gutter [14]; a mesh component [15]; a plurality of auto-filling holes [16]; a plurality of overflow protection holes [17]; a volume of water [19]; a reservoir component [20]; and an optional bag containing an insect attractant [21]. According to one embodiment, the cap component comprises at least three portal arms. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) at least one horizontal entrance opening; (iii) a plurality of vertical window openings; (iv) a plurality of window shields, wherein each window shield is coated on its inner surface with the gel formulation, covers a vertical window opening and contains an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component. According to one embodiment, the autodissemination apparatus further comprises (4) a gel formulation of a composition for management of insect populations, the gel formulation of the composition comprising at least one active ingredient for management of insect populations. According to one embodiment, the described invention provides an autodissemination apparatus of FIG. 3, the apparatus comprising at least one horizontal entrance opening [23]; a plurality of vertical window openings [24]; a plurality of window shields [25], each window shield covers a vertical window opening, each window shield is coated on its inner surface with an insecticide, and each window shield contains an exit opening [26]; a unidirectional funnel [27]; a transfer chamber [28]; a gutter [29]; a mesh component [30]; a plurality of auto-filling holes [31]; a plurality of overflow protection holes [32]; a reservoir component [33]; and a volume of water [34]. According to some such embodiments, the horizontal entrance opening is located on the top of the cap component. According to some such embodiments, the horizontal entrance opening has a circumference smaller than the circumference of the base of the cup component. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings. According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

A skilled artisan would appreciate that the components comprising the autodissemination apparatus described herein can be scaled to a desired dimension. It follows that autodissemination apparati scaled to different dimensions are included within the scope of the invention.

A skilled artisan would appreciate that a single autodissemination apparatus of the present invention can contaminate a plurality of gravid female insects visiting the apparatus. Similarly, a plurality of the autodissemination apparati dispersed in a given location can contaminate multiples of the plurality of gravid female insects visiting the apparati. It follows that a plurality of contaminated gravid female insects would cause killing of the larval population in larger target aqueous bodies. All of the above embodiments are included within the scope of the claimed invention.

IV. Gel Formulation of the Composition

According to one embodiment, the autodissemination apparatus further comprises (4) a gel formulation of a composition for management of insect populations, the gel formulation of the composition comprising at least one active ingredient for management of insect populations.

According to one embodiment, the gel formulation of the composition that can be used with the autodissemination apparatus of the present invention comprises at least one active ingredient for management of insect populations. According to one embodiment, the gel formulation of the composition is capable of transferring to an insect body part, of sticking to such insect body part, and of being released from the insect body part into a target aqueous body where the insect propagates. According to some such embodiments, the gel formulation of the composition is capable of controlling insect larval populations by interrupting the insect life cycle. Such insects include, but are not limited to, mosquitoes, grasshoppers, true bugs, flies, fleas, bees, wasps, ants, lice, moths, and beetles, or any member of *Arthropoda.*

According to one embodiment, the gel formulation of the composition is capable of transferring to an insect body part. According to one embodiment, the gel formulation of the composition is capable of attaching to the surface of an insect body part. According to one embodiment, the gel formulation of the composition is capable of penetrating under a scale of an insect. According to one embodiment, the gel formulation of the composition is glue-like. The term "glue-like" as used herein describes the sticky nature of the formulation that makes it difficult for the insect to remove or dislodge it. According to one embodiment, the gel formulation of the composition is capable of resisting removal. According to one embodiment, the gel formulation of the composition is capable of resisting removal by insect grooming behavior. According to one embodiment, the gel formulation of the composition is capable of being released from the insect body part into a target aqueous body. According to one embodiment, the target aqueous body comprises a contained aqueous body. According to one embodiment, the target aqueous body comprises a contained aqueous body where the insect propagates. According to one embodiment, the release of the gel formulation of the composition from the insect body part to the target aqueous body results in controlling insect larval populations by interrupting insect life cycle. According to one embodiment, the gel formulation of the composition protects the active ingredient from air induced degradation. According to one embodiment, the gel formulation of the composition is contained at the site of application. The term "contained" as used herein refers to the characteristic of being held within a confined area and not prone to being airborne.

According to one embodiment, the gel formulation of the composition comprises an oil based composition of the active ingredient. According to one embodiment, the active ingredient comprises an insecticide. According to one embodiment, the insecticide comprises an insect growth regulator. According to one embodiment, the insect growth regulator comprises pyriproxyfen. According to one embodiment, the insect growth regulator comprises a pyrethroid.

According to one embodiment, the gel formulation of the composition comprises an active ingredient at a concentration at least about 1% to at least about 50% by weight of the composition. According to one embodiment, the gel formulation of the composition comprises an active ingredient at a concentration of at least about 1% by weight of the composition. According to one embodiment, the gel formulation of the composition comprises an active ingredient at a concentration of at least about 2.5% by weight of the composition. According to one embodiment, the gel formulation of the composition comprises an active ingredient at a concentration of at least about 5% by weight of the composition. According to one embodiment, the gel formulation of the composition comprises an active ingredient at a concentration of at least about 7.5% by weight of the composition. According to one embodiment, the gel formulation of the composition comprises an active ingredient at a concentration of at least about 10% by weight of the composition. According to one embodiment, the gel formulation of the composition comprises an active ingredient at a concentration of at least about 15% by weight of the composition. According to one embodiment, the gel formulation of the composition comprises an active ingredient at a concentration of at least about 20% by weight of the composition. According to one embodiment, the gel formulation of the composition comprises an active ingredient at a concentration of at least about 25% by weight of the composition. According to one embodiment, the gel formulation of the composition comprises an active ingredient at a concentration of at least about 30% by weight of the composition. According to one embodiment, the gel formulation of the composition comprises an active ingredient at a concentration of at least about 35% by weight of the composition. According to one embodiment, the gel formulation of the composition comprises an active ingredient at a concentration of at least about 40% by weight of the composition. According to one embodiment, the gel formulation of the composition comprises an active ingredient at a concentration of at least about 45% by weight of the composition. According to one embodiment, the gel formulation of the composition comprises an active ingredient at a concentration of at least about 50% by weight of the composition.

Exemplary insecticides that can be incorporated in gel formulations of the present invention are listed in U.S. Pat. No. 4,690,775, the entire contents of which are incorporated herein by reference. Such insecticides include but are not limited to organo-phosphates, such as parathion, malathion, diazinon, dichlorvos, Guthion®, Bidrin®, ronnel and tetraethyl pyrophosphate (TEPP), carbamates such as physostigmine, neostigmine, isolan, dimetann, dimetilan, pyrolan, pyramat, Sevin®, Zectran®, Mesurol® and carbaryl; DDT and related chlorinated diphenyl methanes, ethanes, propanes and butanes; cyclodienes such as chlordane, heptachlor, aldrin, dieldrin, Thiodan®, telodrin, camphene, Toxaphene®, rotenoids such as piperonyl butoxide, sesamin allethrolone; organic fluoride compounds, such as fluoroacetamide derivatives; nicotinoids such as nicotine, anabasine, diparcol, demethyl-cotinine, nicotyrine; hexachlorocyclohexanes such as lindane; chlorinated phenols and naphthols; and 4,6-dinitro-o-cresol and related compounds and like.

According to one embodiment, the gel formulation of the composition further comprises at least one carrier. Carriers can be natural or synthetic. Carriers may include, but are not limited to, hydrocarbons, fatty alcohols or fatty acids, glycerides, esters of fatty acids with C1-C36 alkanols, and a combination thereof. Exemplary hydrocarbons include, but are not limited to, paraffin, petroleum jelly (Vaseline®), etc. Exemplary fatty alcohols include, but are not limited to, decanol, dodecanol, tetradecanol, hexadecanol, or octadecanol. Exemplary fatty acids include, but are not limited to, C6-C24-alkanoic acids, such as hexanoic acid, octanoic acid, decanoic acid, dodecanoic acid, tetradecanoic acid, hexadecanoic acid or octadecanoic acid, and unsaturated fatty acids, e.g. oleic acid, linoleic acid, etc. Exemplary glycerides include, but are not limited to, olive oil, castor oil, corn oil, cottonseed oil, kerosene, mineral oil, peanut oil, sesame oil, soybean oil, hydrogenated oils, capric acid triglyceride, or glycerol mono-, di-, tri-esters with palmitic and/or stearic acid. Further exemplary carriers include, but are not limited to, beeswax, carbowax, carnauba wax, cetyl palmitate, lanolin, isopropyl myristate, isopropyl stearate, oleic acid decyl ester, ethyl oleate. According to one embodiment, the at least one carrier is a stabilizer. The term "stabilizer" as used herein refers to a chemical that is effective in absorbing water. According to one embodiment, the at least one carrier comprises petroleum jelly. According to one embodiment, the at least one carrier comprises glycerin.

According to one embodiment, the at least one carrier is at a concentration at least about 1% to at least about 50% by weight of the composition. According to one embodiment, the at least one carrier is at a concentration of at least about 1% by weight of the composition. According to one embodiment, the at least one carrier is at a concentration of at least about 2.5% by weight of the composition. According to one embodiment, the at least one carrier is at a concentration of at least about 5% by weight of the composition. According to one embodiment, the at least one carrier is at a concentration of at least about 7.5% by weight of the composition. According to one embodiment, the at least one carrier is at least about 10% by weight of the composition. According to one embodiment, the at least one carrier is at least about 15% by weight of the composition. According to one embodiment, the at least one carrier is at a concentration of at least about 20% by weight of the composition. According to one embodiment, the at least one carrier is at a concentration of at least about 25% by weight of the composition. According to one embodiment, the at least one carrier is at a concentration of at least about 30% by weight of the composition. According to one embodiment, the at least one carrier is at a concentration of at least about 35% by weight of the composition. According to one embodiment, the at least one carrier is at a concentration of at least about 40% by weight of the composition. According to one embodiment, the at least one carrier is at a concentration of at least about 45% by weight of the composition. According to one embodiment, the at least one carrier is at a concentration of at least about 50% by weight of the composition.

According to one embodiment, the gel formulation of the composition further comprises at least one sticking agent. Exemplary sticking agents may include, but are not limited to, organic oils, inorganic oils, and a combination thereof. Exemplary organic oils include, but are not limited to, olive oil, castor oil, corn oil, cottonseed oil, peanut oil, sesame oil, soybean oil, hydrogenated oil, etc. Exemplary inorganic oil include, but are not limited to, mineral oil, kerosene oil, etc. According to one embodiment, the at least one sticking agent enhances transfer of the gel formulation of the composition to an insect body part. According to one embodiment, the at least one sticking agent comprises corn oil. According to one embodiment, the at least one sticking agent is effective in resisting an insect's attempt to remove the gel formulation of the composition transferred to an insect body part. According to one embodiment, the at least one sticking agent comprises a diluent. The term "diluent" as used herein refers to an agent that reduced the concentration of other components of a composition without causing effect on an active ingredient of the composition. According to one embodiment, the at least one sticking agent comprises a stabilizer.

According to one embodiment, the at least one sticking agent is at a concentration at least about 1% to at least about 50% by weight of the composition. According to one embodiment, the at least one sticking agent is at a concentration of at least about 1% by weight of the composition. According to one embodiment, the at least one sticking agent is at a concentration of at least about 2.5% by weight of the composition. According to one embodiment, the at least one sticking agent is at a concentration of at least about 5% by weight of the composition. According to one embodiment, the at least one sticking agent is at a concentration of at least about 7.5% by weight of the composition. According to one embodiment, the at least one sticking agent is at least about 10% by weight of the composition. According to one embodiment, the at least one sticking agent is at least about 15% by weight of the composition. According to one embodiment, the at least one sticking agent is at a concentration of at least about 20% by weight of the composition. According to one embodiment, the at least one sticking agent is at a concentration of at least about 25% by weight of the composition. According to one embodiment, the at least one sticking agent is at a concentration of at least about 30% by weight of the composition. According to one embodiment, the at least one sticking agent is at a concentration of at least about 35% by weight of the composition. According to one embodiment, the at least one sticking agent is at a concentration of at least about 40% by weight of the composition. According to one embodiment, the at least one sticking agent is at a concentration of at least about 45% by weight of the composition. According to one embodiment, the at least one sticking agent is at a concentration of at least about 50% by weight of the composition.

According to one embodiment, the gel formulation of the composition further comprises at least one emulsifying agent. Exemplary emulsifying agents include, but are not limited to, non-ionic emulsifying agents, anionic emulsifying agents and cationic emulsifying agents. Exemplary non-ionic emulsifying agents include, but are not limited to, phenylethyl phenol polyoxyethylene ether, alkylphenyol ethoxylates, Tween-80®, Triton-X, sodium dodecyl sulfate, polyoxyethylated alkylphenols (e.g., octylphenol and nonylphenol), polyoxyethylated sorbitan monoesters, polyoxyethylated fatty or aryl-alkyl alcohols and fatty acids (the latter including esters of polyethylene glycol). Exemplary anionic emulsifying agents include, but are not limited to, calcium dodecyl benzenosulfonate, sodium alkyl, alkyl-aryl and aryl sulfonates, sulfates and phosphates, soaps (i.e., salts of carboxylic acids with at least 8 carbon atoms).

Exemplary cationic emulsifying agents include, but are not limited to, quaternary ammonium salts and salts of primary, secondary and tertiary amines containing at least one hydrocarbon moiety with 8 or more carbon atoms. Common emulsifying agents are described in, among other publications, in Rosen, Surfactants and Interfacial Phenomena, pp. 5-25, John Wiley & Sons (1978), the contents of which are hereby incorporated herein by reference. According to one embodiment, the at least one emulsifying agent comprises a surfactant. According to one embodiment, the at least one emulsifying agent comprises a commercially available emulsifier.

Exemplary emulsifying agents further include but not limited to Sparkleen® detergent, Omega® emulsifier blend, and a combination thereof. According to one embodiment, the emulsifying agent is at a concentration at least about 1% to about 50% by weight of the composition. According to one embodiment, the emulsifying agent is at a concentration of at least about 1% by weight of the composition. According to one embodiment, the emulsifying agent is at a concentration of at least about 2.5% by weight of the composition. According to one embodiment, the emulsifying agent is at a concentration of at least about 5% by weight of the composition. According to one embodiment, the emulsifying agent is at a concentration of at least about 7.5% by weight of the composition. According to one embodiment, the emulsifying agent is at least about 10% by weight of the composition. According to one embodiment, the emulsifying agent is at least about 15% by weight of the composition. According to one embodiment, the emulsifying agent is at a concentration of at least about 20% by weight of the composition. According to one embodiment, the emulsifying agent is at a concentration of at least about 25% by weight of the composition. According to one embodiment, the emulsifying agent is at a concentration of at least about 30% by weight of the composition. According to one embodiment, the emulsifying agent is at a concentration of at least about 35% by weight of the composition. According to one embodiment, the emulsifying agent is at a concentration of at least about 40% by weight of the composition. According to one embodiment, the emulsifying agent is at a concentration of at least about 45% by weight of the composition. According to one embodiment, the emulsifying agent is at a concentration of at least about 50% by weight of the composition.

According to one embodiment, the surfactant is at a concentration at least about 1% to about 50 by weight of the composition. According to one embodiment, the surfactant is at a concentration of at least about 1% by weight of the composition. According to one embodiment, the surfactant is at a concentration of at least about 2.5% by weight of the composition. According to one embodiment, the surfactant is at a concentration of at least about 5% by weight of the composition. According to one embodiment, the surfactant is at a concentration of at least about 7.5% by weight of the composition. According to one embodiment, the surfactant is at least about 10% by weight of the composition. According to one embodiment, the surfactant is at least about 15% by weight of the composition. According to one embodiment, the surfactant is at a concentration of at least about 20% by weight of the composition. According to one embodiment, the surfactant is at a concentration of at least about 25% by weight of the composition. According to one embodiment, the surfactant is at a concentration of at least about 30% by weight of the composition. According to one embodiment, the surfactant is at a concentration of at least about 35% by weight of the composition. According to one embodiment, the surfactant is at a concentration of at least about 40% by weight of the composition. According to one embodiment, the surfactant is at a concentration of at least about 45% by weight of the composition. According to one embodiment, the surfactant is at a concentration of at least about 50% by weight of the composition.

According to one embodiment, the at least one emulsifying agent is effective in releasing the gel formulation of the composition into a target aqueous body upon contact with such and causing an immediate dispersal of the gel formulation of the composition in the target aqueous body. According to one embodiment, the at least one surfactant is effective in releasing the gel formulation of the composition into a target aqueous body and causing an immediate dispersal of the gel formulation of the composition in the target aqueous body.

According to one embodiment, the gel formulation of the composition further comprises at least one particulate ingredient. Exemplary particulate ingredients include, but are not limited to, clay powder, silica powder, talc powder, and a combination thereof.

According to one embodiment, the at least one particulate ingredient is at a concentration at least about 1% to about 50% by weight of the composition. According to one embodiment, the at least one particulate ingredient is at a concentration of at least about 1% by weight of the composition. According to one embodiment, the at least one particulate ingredient is at a concentration of at least about 2.5% by weight of the composition. According to one embodiment, the at least one particulate ingredient is at a concentration of at least about 5% by weight of the composition. According to one embodiment, the at least one particulate ingredient is at a concentration of at least about 7.5% by weight of the composition. According to one embodiment, the at least one particulate ingredient is at least about 10% by weight of the composition. According to one embodiment, the at least one particulate ingredient is at least about 15% by weight of the composition. According to one embodiment, the at least one particulate ingredient is at a concentration of at least about 20% by weight of the composition. According to one embodiment, the at least one particulate ingredient is at a concentration of at least about 25% by weight of the composition. According to one embodiment, the at least one particulate ingredient is at a concentration of at least about 30% by weight of the composition. According to one embodiment, the at least one particulate ingredient is at a concentration of at least about 35% by weight of the composition. According to one embodiment, the at least one particulate ingredient is at a concentration of at least about 40% by weight of the composition. According to one embodiment, the at least one particulate ingredient is at a concentration of at least about 45% by weight of the composition. According to one embodiment, the at least one particulate ingredient is at a concentration of at least about 50% by weight of the composition.

According to one embodiment, the gel formulation of the composition is prepared by initially dissolving the at least one active ingredient in a solvent. Exemplary organic solvents include, but are not limited to, acetone, dimethylsulfoxide (DMSO), dimethyl formamide (DMF), allantoin, urazole, N,N-dimethylacetamide (DMA), decylmethylsulfoxide (CioMSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. According to one embodiment, the solvent is evaporated off. According to one embodiment, the solvent comprises an organic solvent. According to one embodiment, the solvent comprises an aqueous solvent.

According to one embodiment, the gel formulation of the composition has a viscosity of at least about 50 centipoise to at least about 70 centipoise upon preparation. According to one embodiment, the gel formulation of the composition has a viscosity of at least about 50 centipoise to at least about 250,000 centipoise after a period of time. According to one embodiment, the period of time is between at least about one month to at least about six months.

According to one embodiment, the gel formulation of the composition has a viscosity of at least about 50 centipoise upon preparation. According to one embodiment, the gel formulation of the composition has a viscosity of at least about 55 centipoise upon preparation. According to one embodiment, the gel formulation of the composition has a viscosity of at least about 60 centipoise upon preparation. According to one embodiment, the gel formulation of the composition has a viscosity of at least about 65 centipoise upon preparation. According to one embodiment, the gel formulation of the composition has a viscosity of at least about 70 centipoise upon preparation.

According to one embodiment, the gel formulation of the composition has a viscosity of at least about 50 centipoise after a period of time. According to one embodiment, the gel formulation of the composition has a viscosity of at least about 60 centipoise after a period of time. According to one embodiment, the gel formulation of the composition has a viscosity of at least about 70 centipoise after a period of time. According to one embodiment, the gel formulation of the composition has a viscosity of at least about 80 centipoise after a period of time. According to one embodiment, the gel formulation of the composition has a viscosity of at least about 90 centipoise after a period of time. According to one embodiment, the gel formulation of the composition has a viscosity of at least about 100 centipoise after a period of time. According to one embodiment, the gel formulation of the composition has a viscosity of at least about 250 centipoise after a period of time. According to one embodiment, the gel formulation of the composition has a viscosity of at least about 500 centipoise after a period of time. According to one embodiment, the gel formulation of the composition has a viscosity of at least about 1,000 centipoise after a period of time. According to one embodiment, the gel formulation of the composition has a viscosity of at least about 10,000 centipoise after a period of time. According to one embodiment, the gel formulation of the composition has a viscosity of at least about 20,000 centipoise after a period of time. According to one embodiment, the gel formulation of the composition has a viscosity of at least about 30,000 centipoise after a period of time. According to one embodiment, the gel formulation of the composition has a viscosity of at least about 40,000 centipoise after a period of time. According to one embodiment, the gel formulation of the composition has a viscosity of at least about 50,000 centipoise after a period of time. According to one embodiment, the gel formulation of the composition has a viscosity of at least about 60,000 centipoise after a period of time. According to one embodiment, the gel formulation of the composition has a viscosity of at least about 70,000 centipoise after a period of time. According to one embodiment, the gel formulation of the composition has a viscosity of at least about 80,000 centipoise after a period of time. According to one embodiment, the gel formulation of the composition has a viscosity of at least about 90,000 centipoise after a period of time. According to one embodiment, the gel formulation of the composition has a viscosity of at least about 100,000 centipoise after a period of time. According to one embodiment, the gel formulation of the composition has a viscosity of at least about 125,000 centipoise after a period of time. According to one embodiment, the gel formulation of the composition has a viscosity of at least about 150,000 centipoise after a period of time. According to one embodiment, the gel formulation of the composition has a viscosity of at least about 175,000 centipoise after a period of time. According to one embodiment, the gel formulation of the composition has a viscosity of at least about 200,000 centipoise after a period of time. According to one embodiment, the gel formulation of the composition has a viscosity of at least about 225,000 centipoise after a period of time. According to one embodiment, the gel formulation of the composition has a viscosity of at least about 250,000 centipoise after a period of time.

According to one embodiment, the period of time is at least about one month. According to one embodiment, the period of time is at least about two months. According to one embodiment, the period of time is at least about three months. According to one embodiment, the period of time is at least about four months. According to one embodiment, the period of time is at least about five months. According to one embodiment, the period of time is at least about six months.

According to one embodiment, the described invention provides a gel formulation of the composition comprising at least one active ingredient that is released from an insect body part into a target aqueous body where the insect propagates. According to one embodiment, the release is immediate. According to one embodiment, the release is followed by immediate dispersal of the gel formulation of the composition in the target aqueous body where the insect propagates. According to one embodiment, the release results in controlling the insect larval population by interrupting the insect life cycle. According to one embodiment, the at least one active ingredient comprises an insecticide. According to one embodiment, the target aqueous body comprises a water holding container. According to one embodiment, the target aqueous body comprises a larval habitat.

According to one embodiment, the at least one active ingredient is present at a concentration that is effective in causing a biological effect, e.g., preventing larvae from developing into adulthood. According to another embodiment, the at least one active ingredient is present at a concentration effective to cause killing of at least 60%, at least 65%, at least 70%, at least 75%, at least 80%, at least 85%, at least 90%, at least 95%, at least 96%, at least 97%, at least 98% o, at least 99% or 100% of the larval population in the target aqueous body by release from a single contaminated gravid female insect. According to another embodiment, the at least one active ingredient is present at a concentration effective to cause killing of at least 60% of the larval population in the target aqueous body by release from a single contaminated gravid female insect. According to another embodiment, the at least one active ingredient is present at a concentration effective to cause killing of at least 65% of the larval population in the target aqueous body by release from a single contaminated gravid female insect. According to another embodiment, the at least one active ingredient is present at a concentration effective to cause killing of at least 70% of the larval population in the target aqueous body by release from a single contaminated gravid female insect. According to another embodiment, the at least one active ingredient is present at a concentration effective to cause killing of at least 75% of the larval population in the target aqueous body by release from a single contaminated gravid female insect. According to another embodiment, the at least one active ingredient is present at a concentration effective to cause killing of at least 80% of the larval population in the target aqueous body by release from a single contaminated gravid female insect. According to another embodiment, the at least one active ingredient is present at a concentration effective to cause killing of at least 85% of the larval population in the target aqueous body by release from a single contaminated gravid female insect. According to another embodiment, the at least one active ingredient is present at a concentration effective to cause killing of at least 90% of the larval population in the target aqueous body by release from a single contaminated gravid female insect. According to another embodiment, the at least one active ingredient is present at a concentration effective to cause killing of at least 95% of the larval population in the target aqueous body by release from a single contaminated gravid female insect. According to another embodiment, the at least one active ingredient is present at a concentration effective to cause killing of at least 96% of the larval population in the target aqueous body by release from a single contaminated gravid female insect. According to another embodiment, the at least one active ingredient is present at a concentration effective to cause killing of at least 97% of the larval population in the target aqueous body by release from a single contaminated gravid female insect. According to another embodiment, the at least one active ingredient is present at a concentration effective to cause killing of at least 98% of the larval population in the target aqueous body by release from a single contaminated gravid female insect. According to another embodiment, the at least one active ingredient is present at a concentration effective to cause killing of at least 99% of the larval population in the target aqueous body by release from a single contaminated gravid female insect.

According to one embodiment, the target aqueous body holds from about 10 ml to about 2 gallons of water. According to one embodiment, the target aqueous body holds about 10 ml of water. According to one embodiment, the target aqueous body holds about 50 ml of water. According to one embodiment, the target aqueous body holds about 100 ml of water. According to one embodiment, the target aqueous body holds about 250 ml of water. According to one embodiment, the target aqueous body holds about 500 ml of water. According to one embodiment, the target aqueous body holds about 750 ml of water. According to one embodiment, the target aqueous body holds about 1 liter of water. According to one embodiment, the target aqueous body holds about 2 liters of water. According to one embodiment, the target aqueous body holds about 3 liters of water. According to one embodiment, the target aqueous body holds about 3.5 liters of water. According to one embodiment, the target aqueous body holds about 0.5 gallon of water. According to one embodiment, the target aqueous body holds about 1 gallon of water. According to one embodiment, the target aqueous body holds about 1.5 gallons of water. According to one embodiment, the target aqueous body holds about 2 gallons of water.

V. Insect Attractant

According to one embodiment, the apparatus further comprises (5) an insect attractant. Exemplary insect attractants that can be used in one embodiment of the apparatus of the present invention include, but are not limited to, chemical attractants, such as pheromones, and physical attractants, such as visual lures, for example as disclosed in Weinzierl, R. et al, "Insects Attractants and Traps", Publication no.

ENY-277, Alternatives in Insect Management by the Office of Agricultural Entomology, University of Illinois at Urbana-Champaign), one of a series of the Entomology and Nematology Department, Florida Cooperative Extension Service, Institute of Food and Agricultural Sciences, University of Florida. First published: June 1995. Revised: June 2005, the entire contents of which are incorporated herein by reference.

According to one embodiment, the cup component further comprises an insect attractant. According to one such embodiment, the insect attractant is a substrate for bacterial growth. Exemplary substrates include but are not limited to organic food substrates such as dried shredded leaves, such as oak leaves, yeast, rodent pellets, etc. According to one such embodiment, the cup component further comprises a microbial population. According to one such embodiment, the microbial population produces an insect attractant. According to one such embodiment, the insect attractant is a chemical attractant.

According to one embodiment, the reservoir component further comprises a bag containing the insect attractant. According to one embodiment, the bag is constructed from tubular cotton gauze. According to one embodiment, the bag is fixed to the bottom of the reservoir component with paraffin.

Method for Managing Insect Populations

According to another aspect, the described invention provides a method for managing insect populations, the method comprising the steps of: (1) preparing a gel formulation of a composition comprising at least one active ingredient, wherein the gel formulation of the composition is capable of readily transferring to an insect body part, of sticking to such insect body part, and of being readily released from such insect body part into a target aqueous body where the insect propagates; and (2) placing an amount of the gel formulation of the composition comprising at least one insect active ingredient on an applicator within a range of insect behavior site.

According to one embodiment, preparing step (1) comprises steps of: (a) admixing an amount of at least one active ingredient with an amount of a sticking agent; (b) further admixing an amount of at least one carrier; (c) further admixing an amount of at least one emulsifying agent/surfactant. According to one embodiment, preparing step (1) further comprises an optional step of admixing a particulate ingredient. According to one embodiment, the at least one active ingredient may be provided by dissolving in a solvent. Exemplary solvents include but are not limited to acetone, dimethylsulfoxide (DMSO), dimethyl formamide (DMF), allantoin, urazole, N,N-dimethyl acetamide (DMA), decyl-methylsulfoxide (CioMSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. According to one embodiment, the solvent is evaporated off. According to one embodiment, the solvent comprises an organic solvent. According to one embodiment, the solvent comprises an aqueous solvent.

According to one embodiment, the insect is selected from the group consisting of a mosquito, a grasshopper, a true bug, a fly, a flea, a bee, a wasp, an ant, a louse, a moth, and a beetle, or a member of *Arthropoda*. According to one embodiment, the insect population comprises a peridomestic insect population. According to one embodiment, the insect comprises an oviposition-seeking insect. According to one embodiment, the insect comprises a mating insects. According to one embodiment, the insect comprises an insect seeking aggregation behavior. According to one embodiment, the insect comprises an insect engaged in feeding. According to one embodiment, the insect comprises an insect engaged in overwintering. According to one embodiment, the insect comprises an insect engaged in foraging.

According to one embodiment, the insect behavior site comprises an oviposition site. According to one embodiment, the insect behavior site comprises an insect mating site. According to one embodiment, the insect behavior site comprises an insect aggregation site. According to one embodiment, the insect behavior site comprises an insect feeding site. According to one embodiment, the insect behavior site comprises an insect overwintering site. According to one embodiment, the insect behavior site comprises an insect foraging site. According to one embodiment, the insect behavior site comprises a larval site.

Nonlimiting examples of an insect to which the gel formulation of the composition of the present invention is applicable include the following: Hemiptera insects, including, without limitation, planthoppers such as small brown planthopper (*Laodelphax striatellus*), brown planthopper (*Nilaparvata lugens*), white-backed rice planthopper (*Sogatella furcifera*) and the like, leafhoppers such as green rice leafhopper (*Nephotettix cincticeps*), Taiwan green rice leafhopper (*Nephotettix virescens*) and the like, aphides such as cotton aphid (*Aphis gossypii*), green peach aphid (*Myzus persicae*), apple aphid (*Aphis citricola*), turnip aphid (*Lipaphis pserudobrassicae*), pear grean aphid (*Nippolachnus phi*), black citrus aphid (*Toxoptera aurantil*), tropical citrus aphid (*Toxoptera ciidius*) and the like, stink bugs such as green stink bug (*Nezara antennata*), *Cletus punctiger*, bean bug (*Riptortus clavetus*), brownwinged green bug (*Plautia stali*) and the like, whiteflies such as greenhouse whitefly (*Trialeurodes vaporariorum*), sweet-potato whitefy (*Bemisia tabaci*), silverleaf whitefly (*Bemisia argentifolii*) and the like, scale insects such as California red scale (*Aonidiella aurantii*), San Jose scale (*Comstockaspis perniciosa*), citrus snow scale (*Unaspis citri*), white peach scale (*Pseudaulacaspis pentagona*), brown olive scale (*Saissetia oleae*), purple scale (*Lepidosaphes beckii*), red wax scale (*Ceroplastes rubens*), cottonycushion scale (*Icerya purchasi*) and the like, lace bugs, jumping plant louses and the like; Lepidopteran insects, including, without limitation, Pyralidae such as rice stem borer (*Chilo suppressalis*), rice leafroller (*Cnaphalocrocis medinalis*), European corn borer (*Ostrinia nubilalis*), cabbage webworm (*Hellulla undalis*), bluegrass webworm (*Parapediasia teterrella*), cotton leafroller (*Notarch derogata*), Indian meal moth (*Plodia interpuncterlla*) and the like, Noctuidae such as tabaco cutworm (*Spodoptera litura*), rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and the like, Pieridae such as small white (*Pieris rapae*) and the like, Tortricidae such as *Adoxophyes* spp., oriental fruit moth (*Grapholita molesta*), codling moth (*Cydia pomonella*) and the like, Carposinidae such as peach fruit moth (*Carposina niponensis*) and the like, Lyonetiidae such as *Lyonetia* spp. and the like, Lymantriidae such as *Lymantria* spp., *Euproctis* spp. and the like, Yponomeutidae such as diamondback moth (*Plutela xylostella*) and the like, Gelechiidae such as pink ball worm (*Pectinophora gossypiella*) and the like, Arctiidae such as fall webworm (*Hyphantria cunea*) and the like, Tineidae such as casemaking clothes moth (*Tinea translucens*), webbing clothes moth (*Tineola*

*bisselliella*) and the like; *Diptera* insects, including, without limitation, *Culex* spp; such as common mosquito (*Culex pipiens pallens*), oriental latrine fly (*Culex tritaeniorhynchus*) and the like, *Aedes* spp. such as dengue mosquito (*Aedes aegypti*), tiger mosquito (*Aedes albopictus*) and the like, *Anopheles* spp. such as Chinese malaria mosquito (*Anopheles sinensis*) and the like, Chironomidae, Muscidae such as housefly (*Musca domestica*), false stablefly (*Muscina stabulans*) and the like, Calliphoridae, Sarcophagidae, little housefly (*Fannia canicularis*), Anthomyiidae such as seedcorn maggot (*Delia platura*), onion maggot (*Delia antiqua*) and the like, leaf miner flies such as legume leafminer (*Liriomyza trifolii*) and the like, fruit flies, Phoridae, *Drosophila*, moth flies, Simuliidae (blackfly), gadflies, and Culicoides and the like, including, without limitation, Coleopteron insect pests: Corn root worms such as Western corn room worm (*Diabrotica virgifera virgifera*), Southern corn root worm (*Diabrotica undecimpunctata howardi*) and the like, gold beetles such as cupreous chafer (*Anomala cuprea*), soybean beetle (*Anomala rufocuprea*) and the like, weevils such as maize weevil (*Sitophilus zeamais*), ricewater weevil (*Lissorhoptrus oryzophilus*), alfalfa weevil (*Hypera pastica*), adzuki bean weevil (*Callosobruchuys chienensis*) and the like, Tenebrionidae such as yellow mealworm (*Tenebrio molitor*), red flour beetles (*Tribolium castaneum*) and the like, Chrysomilidae such as cucurbit leaf beetle (*Aulacophora femoralis*), striped flea beetle (*Phyllotreta striolata*), Colorado beetle (*Leptinotarsa decemlineata*) and the like, Epilachna such as twenty-eight-spotted ladbirds (*Epilachna vigintioctopunctata*) and the like, Bostrychidae, robe beetle (*Paederus fuscipes*) and the like; Thysanopteran insects, including, without limitation, melon *thrips* (*Thrips palmi*), onion *thrips* (*Thrips tabaci*), flower *thrips* (*Thrips hawaiiensis*), yellow tea *thrips* (*Scirtothrips dorsalis*), flower *thrips* (*Frankliniella intonsa*), western flower *thrips* (*Frankliniella occidentalis*), *Ponticulothrips diospyrosi* and the like; Hymenopteran insects, including, without limitation, ants, hornets, bethylidae, sawflies such as cabbage sawfly (*Athalia japonica*) and the like.

According to one embodiment, the gel formulation of the composition is capable of transferring to an insect body part. According to one embodiment, the gel formulation of the composition is capable of attaching to the surface of an insect body part. According to one embodiment, the gel formulation of the composition is capable of penetrating under a scale of an insect. According to one embodiment, the gel formulation of the composition is glue-like. The term "glue-like" as used herein describes the sticky nature of the formulation that makes it difficult for the insect to remove or dislodge it. According to one embodiment, the gel formulation of the composition is capable of resisting removal. According to one embodiment, the gel formulation of the composition is capable of resisting removal by insect grooming behavior. According to one embodiment, the gel formulation of the composition is capable of being released from the insect body part into a target aqueous body. According to one embodiment, the target aqueous body comprises a contained aqueous body. According to one embodiment, the target aqueous body comprises a contained aqueous body where the insect propagates. According to one embodiment, the release of the gel formulation of the composition from the insect body part to the target aqueous body results in controlling insect larval populations by interrupting insect life cycle. According to one embodiment, the gel formulation of the composition protects the active ingredient from air induced degradation. According to one embodiment, the gel formulation of the composition is contained at the site of application. The term "contained" as used herein refers to the characteristic of being held within a confined area and not prone to being airborne.

According to one embodiment, the gel formulation of the composition comprises an oil based composition of the active ingredient. According to one embodiment, the active ingredient comprises an insecticide. According to one embodiment, the insecticide comprises an insect growth regulator. According to one embodiment, the insect growth regulator comprises pyriproxyfen. According to one embodiment, the insect growth regulator comprises a pyrethroid.

According to one embodiment, the gel formulation of the composition comprises an active ingredient at a concentration at least about 1% to at least about 50% by weight of the composition. According to one embodiment, the gel formulation of the composition comprises an active ingredient at a concentration of at least about 1% by weight of the composition. According to one embodiment, the gel formulation of the composition comprises an active ingredient at a concentration of at least about 2.5% by weight of the composition. According to one embodiment, the gel formulation of the composition comprises an active ingredient at a concentration of at least about 5% by weight of the composition. According to one embodiment, the gel formulation of the composition comprises an active ingredient at a concentration of at least about 7.5% by weight of the composition. According to one embodiment, the gel formulation of the composition comprises an active ingredient at a concentration of at least about 10% by weight of the composition. According to one embodiment, the gel formulation of the composition comprises an active ingredient at a concentration of at least about 15% by weight of the composition. According to one embodiment, the gel formulation of the composition comprises an active ingredient at a concentration of at least about 20% by weight of the composition. According to one embodiment, the gel formulation of the composition comprises an active ingredient at a concentration of at least about 25% by weight of the composition. According to one embodiment, the gel formulation of the composition comprises an active ingredient at a concentration of at least about 30% by weight of the composition. According to one embodiment, the gel formulation of the composition comprises an active ingredient at a concentration of at least about 35% by weight of the composition. According to one embodiment, the gel formulation of the composition comprises an active ingredient at a concentration of at least about 40% by weight of the composition. According to one embodiment, the gel formulation of the composition comprises an active ingredient at a concentration of at least about 45% by weight of the composition. According to one embodiment, the gel formulation of the composition comprises an active ingredient at a concentration of at least about 50% by weight of the composition.

Exemplary insecticides that can be incorporated in gel formulations of the present invention are listed in U.S. Pat. No. 4,690,775, the entire contents of which are incorporated herein by reference. Such insecticides include but are not limited to organo-phosphates, such as parathion, malathion, diazinon, dichlorvos, Guthion®, Bidrin®, ronnel and tetraethyl pyrophosphate (TEPP), carbamates such as physostigmine, neostigmine, isolan, dimetann, dimetilan, pyrolan, pyramat, Sevin®, Zectran®, Mesurol® and carbaryl; DDT and related chlorinated diphenyl methanes, ethanes, propanes and butanes; cyclodienes such as chlordane, heptachlor, aldrin, dieldrin, Thiodan®, telodrin, camphene, Toxaphene®, rotenoids such as piperonyl butoxide, sesamin allethrolone; organic fluoride compounds, such as fluoroacetamide derivatives; nicotinoids such as nicotine, anabasine, diparcol, demethyl-cotinine, nicotyrine; hexachlorocyclohexanes such as lindane; chlorinated phenols and naphthols; and 4,6-dinitro-o-cresol and related compounds and like.

According to one embodiment, the gel formulation of the composition further comprises at least one carrier. Carriers can be natural or synthetic. Carriers may include, but are not limited to, hydrocarbons, fatty alcohols or fatty acids, glycerides, esters of fatty acids with C1-C36 alkanols, and a combination thereof. Exemplary hydrocarbons include, but are not limited to, paraffin, petroleum jelly (Vaseline®), etc. Exemplary fatty alcohols include, but are not limited to, decanol, dodecanol, tetradecanol, hexadecanol, or octadecanol. Exemplary fatty acids include, but are not limited to, C6-C24-alkanoic acids, such as hexanoic acid, octanoic acid, decanoic acid, dodecanoic acid, tetradecanoic acid, hexadecanoic acid or octadecanoic acid, and unsaturated fatty acids, e.g. oleic acid, linoleic acid, etc. Exemplary glycerides include, but are not limited to, olive oil, castor oil, corn oil, cottonseed oil, kerosene, mineral oil, peanut oil, sesame oil, soybean oil, hydrogenated oils, capric acid triglyceride, or glycerol mono-, di-, tri-esters with palmitic and/or stearic acid. Further exemplary carriers include, but are not limited to, beeswax, carbowax, carnauba wax, cetyl palmitate, lanolin, isopropyl myristate, isopropyl stearate, oleic acid decyl ester, ethyl oleate. According to one embodiment, the at least one carrier is a stabilizer. The term "stabilizer" as used herein refers to a chemical that is effective in absorbing water. According to one embodiment, the at least one carrier comprises petroleum jelly. According to one embodiment, the at least one carrier comprises glycerin.

According to one embodiment, the at least one carrier is at a concentration at least about 1% to at least about 50% by weight of the composition. According to one embodiment, the at least one carrier is at a concentration of at least about 1% by weight of the composition. According to one embodiment, the at least one carrier is at a concentration of at least about 2.5% by weight of the composition. According to one embodiment, the at least one carrier is at a concentration of at least about 5% by weight of the composition. According to one embodiment, the at least one carrier is at a concentration of at least about 7.5% by weight of the composition. According to one embodiment, the at least one carrier is at least about 10% by weight of the composition. According to one embodiment, the at least one carrier is at least about 15% by weight of the composition. According to one embodiment, the at least one carrier is at a concentration of at least about 20% by weight of the composition. According to one embodiment, the at least one carrier is at a concentration of at least about 25% by weight of the composition. According to one embodiment, the at least one carrier is at a concentration of at least about 30% by weight of the composition. According to one embodiment, the at least one carrier is at a concentration of at least about 35% by weight of the composition. According to one embodiment, the at least one carrier is at a concentration of at least about 40% by weight of the composition. According to one embodiment, the at least one carrier is at a concentration of at least about 45% by weight of the composition. According to one embodiment, the at least one carrier is at a concentration of at least about 50% by weight of the composition.

According to one embodiment, the gel formulation of the composition further comprises at least one sticking agent. Exemplary sticking agents may include, but are not limited to, organic oils, inorganic oils, and a combination thereof. Exemplary organic oils include, but are not limited to, olive oil, castor oil, corn oil, cottonseed oil, peanut oil, sesame oil, soybean oil, hydrogenated oil, etc. Exemplary inorganic oil include, but are not limited to, mineral oil, kerosene oil, etc. According to one embodiment, the at least one sticking agent enhances transfer of the gel formulation of the composition to an insect body part. According to one embodiment, the at least one sticking agent comprises corn oil. According to one embodiment, the at least one sticking agent is effective in resisting an insect's attempt to remove the gel formulation of the composition transferred to an insect body part. According to one embodiment, the at least one sticking agent comprises a diluent. The term "diluent" as used herein refers to an agent that reduced the concentration of other components of a composition without causing effect on an active ingredient of the composition. According to one embodiment, the at least one sticking agent comprises a stabilizer.

According to one embodiment, the at least one sticking agent is at a concentration at least about 1% to at least about 50% by weight of the composition. According to one embodiment, the at least one sticking agent is at a concentration of at least about 1% by weight of the composition. According to one embodiment, the at least one sticking agent is at a concentration of at least about 2.5% by weight of the composition. According to one embodiment, the at least one sticking agent is at a concentration of at least about 5% by weight of the composition. According to one embodiment, the at least one sticking agent is at a concentration of at least about 7.5% by weight of the composition. According to one embodiment, the at least one sticking agent is at least about 10% by weight of the composition. According to one embodiment, the at least one sticking agent is at least about 15% by weight of the composition. According to one embodiment, the at least one sticking agent is at a concentration of at least about 20% by weight of the composition. According to one embodiment, the at least one sticking agent is at a concentration of at least about 25% by weight of the composition. According to one embodiment, the at least one sticking agent is at a concentration of at least about 30% by weight of the composition. According to one embodiment, the at least one sticking agent is at a concentration of at least about 35% by weight of the composition. According to one embodiment, the at least one sticking agent is at a concentration of at least about 40% by weight of the composition. According to one embodiment, the at least one sticking agent is at a concentration of at least about 45% by weight of the composition. According to one embodiment, the at least one sticking agent is at a concentration of at least about 50% by weight of the composition.

According to one embodiment, the gel formulation of the composition further comprises at least one emulsifying agent. Exemplary emulsifying agents include, but are not limited to, non-ionic emulsifying agents, anionic emulsifying agents and cationic emulsifying agents. Exemplary non-ionic emulsifying agents include, but are not limited to, phenylethyl phenol polyoxyethylene ether, alkylphenol ethoxylates, Tween-80®, Triton-X, sodium dodecyl sulfate, polyoxyethylated alkylphenols (e.g., octylphenol and nonylphenol), polyoxyethylated sorbitan monoesters, polyoxyethylated fatty or aryl-alkyl alcohols and fatty acids (the latter including esters of polyethylene glycol). Exemplary anionic emulsifying agents include, but are not limited to, calcium dodecyl benzenosulfonate, sodium alkyl, alkyl-aryl and aryl sulfonates, sulfates and phosphates, soaps (i.e., salts of carboxylic acids with at least 8 carbon atoms).

Exemplary cationic emulsifying agents include, but are not limited to, quaternary ammonium salts and salts of primary, secondary and tertiary amines containing at least one hydrocarbon moiety with 8 or more carbon atoms. Common emulsifying agents are described in, among other publications, in Rosen, Surfactants and Interfacial Phenomena, pp. 5-25, John Wiley & Sons (1978), the contents of which are hereby incorporated herein by reference. According to one embodiment, the at least one emulsifying agent comprises a surfactant. According to one embodiment, the at least one emulsifying agent comprises a commercially available emulsifier.

Exemplary emulsifying agents further include but not limited to Sparkleen® detergent, Omega® emulsifier blend, and a combination thereof. According to one embodiment, the emulsifying agent is at a concentration at least about 1% to about 50% by weight of the composition. According to one embodiment, the emulsifying agent is at a concentration of at least about 1% by weight of the composition. According to one embodiment, the emulsifying agent is at a concentration of at least about 2.5% by weight of the composition. According to one embodiment, the emulsifying agent is at a concentration of at least about 5% by weight of the composition. According to one embodiment, the emulsifying agent is at a concentration of at least about 7.5% by weight of the composition. According to one embodiment, the emulsifying agent is at least about 10% by weight of the composition. According to one embodiment, the emulsifying agent is at least about 15% by weight of the composition. According to one embodiment, the emulsifying agent is at a concentration of at least about 20% by weight of the composition. According to one embodiment, the emulsifying agent is at a concentration of at least about 25% by weight of the composition. According to one embodiment, the emulsifying agent is at a concentration of at least about 30% by weight of the composition. According to one embodiment, the emulsifying agent is at a concentration of at least about 35% by weight of the composition. According to one embodiment, the emulsifying agent is at a concentration of at least about 40% by weight of the composition. According to one embodiment, the emulsifying agent is at a concentration of at least about 45% by weight of the composition. According to one embodiment, the emulsifying agent is at a concentration of at least about 50% by weight of the composition.

According to one embodiment, the surfactant is at a concentration at least about 1% to about 50 by weight of the composition. According to one embodiment, the surfactant is at a concentration of at least about 1% by weight of the composition. According to one embodiment, the surfactant is at a concentration of at least about 2.5% by weight of the composition. According to one embodiment, the surfactant is at a concentration of at least about 5% by weight of the composition. According to one embodiment, the surfactant is at a concentration of at least about 7.5% by weight of the composition. According to one embodiment, the surfactant is at least about 10% by weight of the composition. According to one embodiment, the surfactant is at least about 15% by weight of the composition. According to one embodiment, the surfactant is at a concentration of at least about 20% by weight of the composition. According to one embodiment, the surfactant is at a concentration of at least about 25% by weight of the composition. According to one embodiment, the surfactant is at a concentration of at least about 30% by weight of the composition. According to one embodiment, the surfactant is at a concentration of at least about 35% by weight of the composition. According to one embodiment, the surfactant is at a concentration of at least about 40% by weight of the composition. According to one embodiment, the surfactant is at a concentration of at least about 45% by weight of the composition. According to one embodiment, the surfactant is at a concentration of at least about 50% by weight of the composition.

According to one embodiment, the at least one emulsifying agent is effective in releasing the gel formulation of the composition into a target aqueous body upon contact with such and causing an immediate dispersal of the gel formulation of the composition in the target aqueous body. According to one embodiment, the at least one surfactant is effective in releasing the gel formulation of the composition into a target aqueous body and causing an immediate dispersal of the gel formulation of the composition in the target aqueous body.

According to one embodiment, the gel formulation of the composition further comprises at least one particulate ingredient. Exemplary particulate ingredients include, but are not limited to, clay powder, silica powder, talc powder, and a combination thereof.

According to one embodiment, the at least one particulate ingredient is at a concentration at least about 1% to about 50% by weight of the composition. According to one embodiment, the at least one particulate ingredient is at a concentration of at least about 1% by weight of the composition. According to one embodiment, the at least one particulate ingredient is at a concentration of at least about 2.5% by weight of the composition. According to one embodiment, the at least one particulate ingredient is at a concentration of at least about 5% by weight of the composition. According to one embodiment, the at least one particulate ingredient is at a concentration of at least about 7.5% by weight of the composition. According to one embodiment, the at least one particulate ingredient is at least about 10% by weight of the composition. According to one embodiment, the at least one particulate ingredient is at least about 15% by weight of the composition. According to one embodiment, the at least one particulate ingredient is at a concentration of at least about 20% by weight of the composition. According to one embodiment, the at least one particulate ingredient is at a concentration of at least about 25% by weight of the composition. According to one embodiment, the at least one particulate ingredient is at a concentration of at least about 30% by weight of the composition. According to one embodiment, the at least one particulate ingredient is at a concentration of at least about 35% by weight of the composition. According to one embodiment, the at least one particulate ingredient is at a concentration of at least about 40% by weight of the composition. According to one embodiment, the at least one particulate ingredient is at a concentration of at least about 45% by weight of the composition. According to one embodiment, the at least one particulate ingredient is at a concentration of at least about 50% by weight of the composition.

According to one embodiment, the gel formulation of the composition is prepared by initially dissolving the at least one active ingredient in a solvent. Exemplary organic solvents include, but are not limited to, acetone, dimethylsulfoxide (DMSO), dimethyl formamide (DMF), allantoin, urazole, N,N-dimethylacetamide (DMA), decylmethylsulfoxide (CioMSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. According to one embodiment, the solvent is evaporated off. According to one embodiment, the solvent comprises an organic solvent. According to one embodiment, the solvent comprises an aqueous solvent.

According to one embodiment, the gel formulation of the composition has a viscosity of at least about 50 centipoise to at least about 70 centipoise upon preparation. According to one embodiment, the gel formulation of the composition has a viscosity of at least about 50 centipoise to at least about 250,000 centipoise after a period of time. According to one embodiment, the period of time is between at least about one month to at least about six months.

According to one embodiment, the gel formulation of the composition has a viscosity of at least about 50 centipoise upon preparation. According to one embodiment, the gel formulation of the composition has a viscosity of at least about 55 centipoise upon preparation. According to one embodiment, the gel formulation of the composition has a viscosity of at least about 60 centipoise upon preparation. According to one embodiment, the gel formulation of the composition has a viscosity of at least about 65 centipoise upon preparation. According to one embodiment, the gel formulation of the composition has a viscosity of at least about 70 centipoise upon preparation.

According to one embodiment, the gel formulation of the composition has a viscosity of at least about 50 centipoise after a period of time. According to one embodiment, the gel formulation of the composition has a viscosity of at least about 60 centipoise after a period of time. According to one embodiment, the gel formulation of the composition has a viscosity of at least about 70 centipoise after a period of time. According to one embodiment, the gel formulation of the composition has a viscosity of at least about 80 centipoise after a period of time. According to one embodiment, the gel formulation of the composition has a viscosity of at least about 90 centipoise after a period of time. According to one embodiment, the gel formulation of the composition has a viscosity of at least about 100 centipoise after a period of time. According to one embodiment, the gel formulation of the composition has a viscosity of at least about 250 centipoise after a period of time. According to one embodiment, the gel formulation of the composition has a viscosity of at least about 500 centipoise after a period of time. According to one embodiment, the gel formulation of the composition has a viscosity of at least about 1,000 centipoise after a period of time. According to one embodiment, the gel formulation of the composition has a viscosity of at least about 10,000 centipoise after a period of time. According to one embodiment, the gel formulation of the composition has a viscosity of at least about 20,000 centipoise after a period of time. According to one embodiment, the gel formulation of the composition has a viscosity of at least about 30,000 centipoise after a period of time. According to one embodiment, the gel formulation of the composition has a viscosity of at least about 40,000 centipoise after a period of time. According to one embodiment, the gel formulation of the composition has a viscosity of at least about 50,000 centipoise after a period of time. According to one embodiment, the gel formulation of the composition has a viscosity of at least about 60,000 centipoise after a period of time. According to one embodiment, the gel formulation of the composition has a viscosity of at least about 70,000 centipoise after a period of time. According to one embodiment, the gel formulation of the composition has a viscosity of at least about 80,000 centipoise after a period of time. According to one embodiment, the gel formulation of the composition has a viscosity of at least about 90,000 centipoise after a period of time. According to one embodiment, the gel formulation of the composition has a viscosity of at least about 100,000 centipoise after a period of time. According to one embodiment, the gel formulation of the composition has a viscosity of at least about 125,000 centipoise after a period of time. According to one embodiment, the gel formulation of the composition has a viscosity of at least about 150,000 centipoise after a period of time. According to one embodiment, the gel formulation of the composition has a viscosity of at least about 175,000 centipoise after a period of time. According to one embodiment, the gel formulation of the composition has a viscosity of at least about 200,000 centipoise after a period of time. According to one embodiment, the gel formulation of the composition has a viscosity of at least about 225,000 centipoise after a period of time. According to one embodiment, the gel formulation of the composition has a viscosity of at least about 250,000 centipoise after a period of time.

According to one embodiment, the period of time is at least about one month. According to one embodiment, the period of time is at least about two months. According to one embodiment, the period of time is at least about three months. According to one embodiment, the period of time is at least about four months. According to one embodiment, the period of time is at least about five months. According to one embodiment, the period of time is at least about six months.

According to one embodiment, the described invention provides a gel formulation of the composition that topically contaminates an oviposition-seeking insect. As used herein, the terms "topical" and "topically" are used interchangeably to refer to delivery of an insect growth regulator onto one or more surfaces of an insect's body part, including epithelial surfaces. According to one embodiment, the described invention provides a gel formulation of the composition that topically contaminates a mating insect. According to one embodiment, the described invention provides a gel formulation of the composition that topically contaminates an insect engaged in aggregation behavior. According to one embodiment, the insect comprises an insect engaged in feeding. According to one embodiment, the insect comprises an insect engaged in overwintering. According to one embodiment, the insect comprises an insect engaged in foraging.

The mode of application of the gel formulation of the composition will depend on the type of the insect. According to one embodiment, the gel formulation of the composition is applied on an applicator that attracts the insect. According to one embodiment, the applicator is a mesh. According to one embodiment, the mesh is placed within a container. According to one embodiment, the applicator is placed within an autodissemination apparatus. According to one embodiment, the applicator is placed within an insect trap. According to one embodiment, the insect trap is a container. According to one embodiment, the applicator is a sheet. According to one embodiment, the applicator is a cup. According to one embodiment, the applicator is a film.

According to one embodiment, the autodissemination apparatus comprises: (1) a cap component, wherein the cap component comprises (i) a plurality of openings, and (ii) a plurality of auto-filling holes; (2) a cup component, wherein the cup component comprises (i) a water absorbing gel; (ii) a plurality of overflow protection holes, and (iii) a weighted base; (3) a mesh component. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the autodissemination apparatus comprises: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component. According to one embodiment, the cap component comprises at least three portal arms. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the autodissemination apparatus comprises: (1) a cap component, wherein the cap component comprises (i) a transfer chamber; (ii) at least one horizontal entrance opening; (iii) a plurality of vertical window openings; (iv) a plurality of window shields, wherein each window shield is coated on its inner surface with the gel formulation, covers a vertical window opening and contains an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component. According to some such embodiments, the horizontal entrance opening is located on the top of the cap component. According to some such embodiments, the horizontal entrance opening has a circumference smaller than the circumference of the base of the cup component. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings. According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

Exemplary autodissemination apparati that can be used for applying the gel formulations of the present invention include, but are not limited to, autodissemination devices, insect traps, insect feeding stations, insect contamination chambers, insect bait stations, etc, such as disclosed in U.S. Pat. No. 5,452,540, U.S. Pat. No. 5,359,807, U.S. Pat. No. 4,671,010, U.S. Pat. No. 5,042,194, U.S. Pat. No. 4,485,582, U.S. Pat. No. 5,057,315, U.S. Pat. No. 5,057,316, U.S. Pat. No. 5,189,831, U.S. Pat. No. Des. 324,406, and U.S. Pat. No. 5,238,681, the entire contents of which are incorporated herein by reference. A skilled artisan would appreciate that such exemplary autodissemination apparatus can be modified for the application of the gel formulation of the composition of the present invention.

According to one embodiment, the described invention provides a gel formulation of the composition comprising at least one active ingredient that is released from an insect body part into a target aqueous body where the insect propagates. According to one embodiment, the release is immediate. According to one embodiment, the release is followed by immediate dispersal of the gel formulation of the composition in the target aqueous body where the insect propagates. According to one embodiment, the release results in controlling the insect larval population by interrupting the insect life cycle. According to one embodiment, the at least one active ingredient comprises an insecticide. According to one embodiment, the target aqueous body comprises a water holding container. According to one embodiment, the target aqueous body comprises a larval habitat.

According to one embodiment, the at least one active ingredient is present at a concentration that is effective in causing a biological effect, e.g., preventing larvae from developing into adulthood. According to another embodiment, the at least one active ingredient is present at a concentration effective to cause killing of at least 60%, at least 65%, at least 70%, at least 75%, at least 80%, at least 85%, at least 90%, at least 95%, at least 96%, at least 97%, at least 98% o, at least 99% or 100% of the larval population in the target aqueous body by release from a single contaminated gravid female insect. According to another embodiment, the at least one active ingredient is present at a concentration effective to cause killing of at least 60% of the larval population in the target aqueous body by release from a single contaminated gravid female insect. According to another embodiment, the at least one active ingredient is present at a concentration effective to cause killing of at least 65% of the larval population in the target aqueous body by release from a single contaminated gravid female insect. According to another embodiment, the at least one active ingredient is present at a concentration effective to cause killing of at least 70% of the larval population in the target aqueous body by release from a single contaminated gravid female insect. According to another embodiment, the at least one active ingredient is present at a concentration effective to cause killing of at least 75% of the larval population in the target aqueous body by release from a single contaminated gravid female insect. According to another embodiment, the at least one active ingredient is present at a concentration effective to cause killing of at least 80% of the larval population in the target aqueous body by release from a single contaminated gravid female insect. According to another embodiment, the at least one active ingredient is present at a concentration effective to cause killing of at least 85% of the larval population in the target aqueous body by release from a single contaminated gravid female insect. According to another embodiment, the at least one active ingredient is present at a concentration effective to cause killing of at least 90% of the larval population in the target aqueous body by release from a single contaminated gravid female insect. According to another embodiment, the at least one active ingredient is present at a concentration effective to cause killing of at least 95% of the larval population in the target aqueous body by release from a single contaminated gravid female insect. According to another embodiment, the at least one active ingredient is present at a concentration effective to cause killing of at least 96% of the larval population in the target aqueous body by release from a single contaminated gravid female insect. According to another embodiment, the at least one active ingredient is present at a concentration effective to cause killing of at least 97% of the larval population in the target aqueous body by release from a single contaminated gravid female insect. According to another embodiment, the at least one active ingredient is present at a concentration effective to cause killing of at least 98% of the larval population in the target aqueous body by release from a single contaminated gravid female insect. According to another embodiment, the at least one active ingredient is present at a concentration effective to cause killing of at least 99% of the larval population in the target aqueous body by release from a single contaminated gravid female insect.

According to one embodiment, the target aqueous body holds from about 10 ml to about 2 gallons of water. According to one embodiment, the target aqueous body holds about 10 ml of water. According to one embodiment, the target aqueous body holds about 50 ml of water. According to one embodiment, the target aqueous body holds about 100 ml of water. According to one embodiment, the target aqueous body holds about 250 ml of water. According to one embodiment, the target aqueous body holds about 500 ml of water. According to one embodiment, the target aqueous body holds about 750 ml of water. According to one embodiment, the target aqueous body holds about 1 liter of water. According to one embodiment, the target aqueous body holds about 2 liters of water. According to one embodiment, the target aqueous body holds about 3 liters of water. According to one embodiment, the target aqueous body holds about 3.5 liters of water. According to one embodiment, the target aqueous body holds about 0.5 gallon of water. According to one embodiment, the target aqueous body holds about 1 gallon of water. According to one embodiment, the target aqueous body holds about 1.5 gallons of water. According to one embodiment, the target aqueous body holds about 2 gallons of water.

A skilled artisan would appreciate that a single autodissemination apparatus of the present invention can contaminate a plurality of gravid female insects visiting the apparatus. Similarly, a plurality of the autodissemination apparati dispersed in a given location can contaminate multiples of the plurality of gravid female insects visiting the apparati. It follows that a plurality of contaminated gravid female insects would cause killing of the larval population in larger target aqueous bodies. All of the above embodiments are included within the scope of the claimed invention.

According to one embodiment, the apparatus further comprises an insect attractant. Exemplary insect attractants that can be used in one embodiment of the apparatus of the present invention include but are not limited to chemical attractants, such as pheromones, and physical attractants, such as visual lures, for example as disclosed in Weinzierl, R. et al, "Insects Attractants and Traps", Publication no. ENY-277, Alternatives in Insect Management by the Office of Agricultural Entomology, University of Illinois at Urbana-Champaign), one of a series of the Entomology and Nematology Department, Florida Cooperative Extension Service, Institute of Food and Agricultural Sciences, University of Florida. First published: June 1995. Revised: June 2005, the entire contents of which are incorporated herein by reference.

According to one embodiment, the cup component further comprises an insect attractant. According to one such embodiment, the insect attractant is a substrate for bacterial growth. According to one such embodiment, the cup component further comprises a microbial population. According to one such embodiment, the microbial population produces an insect attractant. According to one such embodiment, the insect attractant is a chemical attractant.

Method for Autodisseminating an Active Ingredient

According to another aspect, the described invention provides a method for autodisseminating an active ingredient, the method comprising dispersing for autodissemination of a composition comprising an active ingredient for insect management using an autodissemination apparatus, the apparatus comprising at least three main components: (1) a bottom cup component; (2) an upper cap component, and (3) a mesh component.

According to one embodiment, the apparatus comprises: (1) a cap component, wherein the cap component comprises (i) a plurality of entrances, and (ii) a plurality of auto-filling holes; (2) a cup component, wherein the cup component comprises (i) a water absorbing gel; (ii) a plurality of overflow protection holes, and (iii) a weighted base; (3) a mesh component. According to one embodiment, the autodissemination apparatus further comprises (4) a gel formulation of a composition for management of insect populations, the gel formulation of the composition comprising at least one active ingredient for management of insect populations. According to one embodiment, the mesh component comprises at least one active ingredient. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component. According to one embodiment, the cap component comprises at least three portal arms. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) at least one horizontal entrance opening; (iii) a plurality of vertical window openings; (iv) a plurality of window shields, each coated on its inner surface with pyriproxyfen, each covering a vertical window opening and containing an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component. According to one embodiment, the autodissemination apparatus further comprises (4) the gel formulation of the composition for management of insect populations, the gel formulation of the composition comprising at least one active ingredient for management of insect populations. According to some such embodiments, the horizontal entrance opening is located on the top of the cap component. According to some such embodiments, the horizontal entrance opening has a circumference smaller than the circumference of the base of the cup component. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings. According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

According to one embodiment, the at least one active ingredient comprises an insecticide. According to one embodiment, the insecticide comprises an insect growth regulator. According to one embodiment, the insect growth regulator comprises pyriproxyfen. According to one embodiment, the insect growth regulator comprises a pyrethroid.

According to one embodiment, the at least one active ingredient is present at a concentration of at least about 1% to at least about 50% by weight of the composition. According to one embodiment, the gel formulation of the composition comprises an active ingredient at a concentration of at least about 1% by weight of the composition. According to one embodiment, the gel formulation of the composition comprises an active ingredient at a concentration of at least about 2.5% by weight of the composition. According to one embodiment, the gel formulation of the composition comprises an active ingredient at a concentration of at least about 5% by weight of the composition. According to one embodiment, the gel formulation of the composition comprises an active ingredient at a concentration of at least about 7.5% by weight of the composition. According to one embodiment, the gel formulation of the composition comprises an active ingredient at a concentration of at least about 10% by weight of the composition. According to one embodiment, the gel formulation of the composition comprises an active ingredient at a concentration of at least about 15% by weight of the composition. According to one embodiment, the gel formulation of the composition comprises an active ingredient at a concentration of at least about 20% by weight of the composition. According to one embodiment, the gel formulation of the composition comprises an active ingredient at a concentration of at least about 25% by weight of the composition. According to one embodiment, the gel formulation of the composition comprises an active ingredient at a concentration of at least about 30% by weight of the composition. According to one embodiment, the gel formulation of the composition comprises an active ingredient at a concentration of at least about 35% by weight of the composition. According to one embodiment, the gel formulation of the composition comprises an active ingredient at a concentration of at least about 40% by weight of the composition. According to one embodiment, the gel formulation of the composition comprises an active ingredient at a concentration of at least about 45% by weight of the composition. According to one embodiment, the gel formulation of the composition comprises an active ingredient at a concentration of at least about 50% by weight of the composition.

According to one embodiment, the at least one of the cap component and the cup component comprise a molded optionally biodegradable material and a binder.

According to one embodiment, the described invention provides a gel formulation of the composition comprising at least one active ingredient that is released from an insect body part into a target aqueous body where the insect propagates. According to one embodiment, the release is immediate. According to one embodiment, the release is followed by immediate dispersal of the gel formulation of the composition in the target aqueous body where the insect propagates. According to one embodiment, the release results in controlling the insect larval population by interrupting the insect life cycle. According to one embodiment, the at least one active ingredient comprises an insecticide. According to one embodiment, the target aqueous body comprises a water holding container. According to one embodiment, the target aqueous body comprises a larval habitat.

According to one embodiment, the at least one active ingredient is present at a concentration that is effective in causing a biological effect, e.g., preventing larvae from developing into adulthood. According to another embodiment, the at least one active ingredient is present at a concentration effective to cause killing of at least 60%, at least 65%, at least 70%, at least 75%, at least 80%, at least 85%, at least 90%, at least 95%, at least 96%, at least 97%, at least 98% o, at least 99% or 100% of the larval population in the target aqueous body by release from a single contaminated gravid female insect. According to another embodiment, the at least one active ingredient is present at a concentration effective to cause killing of at least 60% of the larval population in the target aqueous body by release from a single contaminated gravid female insect. According to another embodiment, the at least one active ingredient is present at a concentration effective to cause killing of at least 65% of the larval population in the target aqueous body by release from a single contaminated gravid female insect. According to another embodiment, the at least one active ingredient is present at a concentration effective to cause killing of at least 70% of the larval population in the target aqueous body by release from a single contaminated gravid female insect. According to another embodiment, the at least one active ingredient is present at a concentration effective to cause killing of at least 75% of the larval population in the target aqueous body by release from a single contaminated gravid female insect. According to another embodiment, the at least one active ingredient is present at a concentration effective to cause killing of at least 80% of the larval population in the target aqueous body by release from a single contaminated gravid female insect. According to another embodiment, the at least one active ingredient is present at a concentration effective to cause killing of at least 85% of the larval population in the target aqueous body by release from a single contaminated gravid female insect. According to another embodiment, the at least one active ingredient is present at a concentration effective to cause killing of at least 90% of the larval population in the target aqueous body by release from a single contaminated gravid female insect. According to another embodiment, the at least one active ingredient is present at a concentration effective to cause killing of at least 95% of the larval population in the target aqueous body by release from a single contaminated gravid female insect. According to another embodiment, the at least one active ingredient is present at a concentration effective to cause killing of at least 96% of the larval population in the target aqueous body by release from a single contaminated gravid female insect. According to another embodiment, the at least one active ingredient is present at a concentration effective to cause killing of at least 97% of the larval population in the target aqueous body by release from a single contaminated gravid female insect. According to another embodiment, the at least one active ingredient is present at a concentration effective to cause killing of at least 98% of the larval population in the target aqueous body by release from a single contaminated gravid female insect. According to another embodiment, the at least one active ingredient is present at a concentration effective to cause killing of at least 99% of the larval population in the target aqueous body by release from a single contaminated gravid female insect.

According to one embodiment, the target aqueous body holds from about 10 ml to about 2 gallons of water. According to one embodiment, the target aqueous body holds about 10 ml of water. According to one embodiment, the target aqueous body holds about 50 ml of water. According to one embodiment, the target aqueous body holds about 100 ml of water. According to one embodiment, the target aqueous body holds about 250 ml of water. According to one embodiment, the target aqueous body holds about 500 ml of water. According to one embodiment, the target aqueous body holds about 750 ml of water. According to one embodiment, the target aqueous body holds about 1 liter of water. According to one embodiment, the target aqueous body holds about 2 liters of water. According to one embodiment, the target aqueous body holds about 3 liters of water. According to one embodiment, the target aqueous body holds about 3.5 liters of water. According to one embodiment, the target aqueous body holds about 0.5 gallon of water. According to one embodiment, the target aqueous body holds about 1 gallon of water. According to one embodiment, the target aqueous body holds about 1.5 gallons of water. According to one embodiment, the target aqueous body holds about 2 gallons of water.

A skilled artisan would appreciate that a single autodissemination apparatus of the present invention can contaminate a plurality of gravid female insects visiting the apparatus. Similarly, a plurality of the autodissemination apparati dispersed in a given location can contaminate multiples of the plurality of gravid female insects visiting the apparati. It follows that a plurality of contaminated gravid female insects would cause killing of the larval population in larger target aqueous bodies. All of the above embodiments are included within the scope of the claimed invention.

Exemplary insecticides that can be incorporated in gel formulations of the present invention are listed in U.S. Pat. No. 4,690,775, the entire contents of which are incorporated herein by reference. Such insecticides include but are not limited to organo-phosphates, such as parathion, malathion, diazinon, dichlorvos, Guthion®, Bidrin®, ronnel and tetraethyl pyrophosphate (TEPP), carbamates such as physostigmine, neostigmine, isolan, dimetann, dimetilan, pyrolan, pyramat, Sevin®, Zectran®, Mesurol® and carbaryl; DDT and related chlorinated diphenyl methanes, ethanes, propanes and butanes; cyclodienes such as chlordane, heptachlor, aldrin, dieldrin, Thiodan®, telodrin, camphene, Toxaphene®, rotenoids such as piperonyl butoxide, sesamin allethrolone; organic fluoride compounds, such as fluoroacetamide derivatives; nicotinoids such as nicotine, anabasine, diparcol, demethyl-cotinine, nicotyrine; hexachlorocyclohexanes such as lindane; chlorinated phenols and naphthols; and 4,6-dinitro-o-cresol and related compounds and like.

According to one embodiment, the apparatus further comprises an insect attractant. Exemplary insect attractants that can be used in one embodiment of the apparatus of the present invention include but are not limited to chemical attractants, such as pheromones, and physical attractants, such as visual lures, for example as disclosed in Weinzierl, R. et al, "Insects Attractants and Traps", Publication no. ENY-277, Alternatives in Insect Management by the Office of Agricultural Entomology, University of Illinois at Urbana-Champaign), one of a series of the Entomology and Nematology Department, Florida Cooperative Extension Service, Institute of Food and Agricultural Sciences, University of Florida. First published: June 1995. Revised: June 2005, the entire contents of which are incorporated herein by reference.

According to one embodiment, the cup component further comprises an insect attractant. According to one such embodiment, the insect attractant is a substrate for bacterial growth. According to one such embodiment, the cup component further comprises a microbial population. According to one such embodiment, the microbial population produces an insect attractant. According to one such embodiment, the insect attractant is a chemical attractant.

Autodissemination System

According to another aspect, the described invention provides a system for autodisseminating an active ingredient for insect management, the system comprising (I) an autodissemination apparatus, the apparatus comprising at least three main components: (1) a bottom cup component; (2) an upper cap component, and (3) a mesh component; and (II) a gel formulation of a composition comprising at least one active ingredient.

Exemplary insect populations that can be managed using the system of the present invention include but are not limited to mosquitoes, grasshoppers, true bugs, flies, fleas, bees, wasps, ants, lice, moths, and beetles, or any member of *Arthropoda*. Nonlimiting examples of an insect to which the autodissemination system of the present invention is applicable include the following: Hemiptera insects, including, without limitation, planthoppers such as small brown planthopper (*Laodelphax striatellus*), brown planthopper (*Nilaparvata lugens*), white-backed rice planthopper (*Sogatella furcifera*) and the like, leafhoppers such as green rice leafhopper (*Nephotettix cincticeps*), Taiwan green rice leafhopper (*Nephotettix virescens*) and the like, aphides such as cotton aphid (*Aphis gossypii*), green peach aphid (*Myzus persicae*), apple aphid (*Aphis citricola*), turnip aphid (*Lipaphis pserudobrassicae*), pear grean aphid (*Nippolachnus phi*), black citrus aphid (*Toxoptera aurantil*), tropical citrus aphid (*Toxoptera ciidius*) and the like, stink bugs such as green stink bug (*Nezara antennata*), *Cletus punctiger*, bean bug (*Riptortus clavetus*), brownwinged green bug (*Plautia stali*) and the like, whiteflies such as greenhouse whitefly (*Trialeurodes vaporariorum*), sweet-potato whitefy (*Bemisia tabaci*), silverleaf whitefly (*Bemisia argentifolii*) and the like, scale insects such as California red scale (*Aonidiella aurantii*), San Jose scale (*Comstockaspis perniciosa*), citrus snow scale (*Unaspis citri*), white peach scale (*Pseudaulacaspis pentagona*), brown olive scale (*Saissetia oleae*), purple scale (*Lepidosaphes beckii*), red wax scale (*Ceroplastes rubens*), cottonycushion scale (*Icerya purchasi*) and the like, lace bugs, jumping plant louses and the like; Lepidopteran insects, including, without limitation, Pyralidae such as rice stem borer (*Chilo suppressalis*), rice leafroller (*Cnaphalocrocis medinalis*), European corn borer (*Ostrinia nubilalis*), cabbage webworm (*Hellulla undalis*), bluegrass webworm (*Parapediasia teterrella*), cotton leafroller (*Notarch derogata*), Indian meal moth (*Plodia interpuncterlla*) and the like, Noctuidae such as tabaco cutworm (*Spodoptera litura*), rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and the like, Pieridae such as small white (*Pieris rapae*) and the like, Tortricidae such as *Adoxophyes* spp., oriental fruit moth (*Grapholita molesta*), codling moth (*Cydia pomonella*) and the like, Carposinidae such as peach fruit moth (*Carposina niponensis*) and the like, Lyonetiidae such as *Lyonetia* spp. and the like, Lymantriidae such as *Lymantria* spp., *Euproctis* spp. and the like, Yponomeutidae such as diamondback moth (*Plutela xylostella*) and the like, Gelechiidae such as pink ball worm (*Pectinophora gossypiella*) and the like, Arctiidae such as fall webworm (*Hyphantria cunea*) and the like, Tineidae such as casemaking clothes moth (*Tinea translucens*), webbing clothes moth (*Tineola bisselliella*) and the like; Diptera insects, including, without limitation, *Culex* spp; such as common mosquito (*Culex pipiens pallens*), oriental latrine fly (*Culex tritaeniorhynchus*) and the like, *Aedes* spp. such as dengue mosquito (*Aedes aegypti*), tiger mosquito (*Aedes albopictus*) and the like, *Anopheles* spp. such as Chinese malaria mosquito (*Anopheles sinensis*) and the like, Chironomidae, Muscidae such as housefly (*Musca domestica*), false stablefly (*Muscina stabulans*) and the like, Calliphoridae, Sarcophagidae, little housefly (*Fannia canicularis*), Anthomyiidae such as seedcorn maggot (*Delia platura*), onion maggot (*Delia antiqua*) and the like, leaf miner flies such as legume leafminer (*Liriomyza trifolii*) and the like, fruit flies, Phoridae, *Drosophila*, moth flies, Simuliidae (blackfly), gadflies, and Culicoides and the like, including, without limitation, Coleopteron insect pests: Corn root worms such as Western corn room worm (*Diabrotica virgifera virgifera*), Southern corn root worm (*Diabrotica undecimpunctata howardi*) and the like, gold beetles such as cupreous chafer (*Anomala cuprea*), soybean beetle (*Anomala rufocuprea*) and the like, weevils such as maize weevil (*Sitophilus zeamais*), ricewater weevil (*Lissorhoptrus oryzophilus*), alfalfa weevil (*Hypera pastica*), adzuki bean weevil (*Callosobruchuys chienensis*) and the like, Tenebrionidae such as yellow mealworm (*Tenebrio molitor*), red flour beetles (*Tribolium castaneum*) and the like, Chrysomilidae such as cucurbit leaf beetle (*Aulacophora femoralis*), striped flea beetle (*Phyllotreta striolata*), Colorado beetle (*Leptinotarsa decemlineata*) and the like, *Epilachna* such as twenty-eight-spotted ladbirds (*Epilachna vigintioctopunctata*) and the like, Bostrychidae, robe beetle (*Paederus fuscipes*) and the like; Thysanopteran insects, including, without limitation, melon *thrips* (*Thrips palmi*), onion thrips (*Thrips tabaci*), flower *thrips* (*Thrips hawaiiensis*), yellow tea *thrips* (*Scirtothrips dorsalis*), flower *thrips* (*Frankliniella intonsa*), western flower *thrips* (*Frankliniella occidentalis*), *Ponticulothrips diospyrosi* and the like; Hymenopteran insects, including, without limitation, ants, hornets, bethylidae, sawflies such as cabbage sawfly (*Athalia japonica*) and the like.

According to one embodiment, the gel formulation of the composition is capable of transferring to an insect body part and sticking to such insect body part and wherein the gel formulation of the composition is further capable of being released from the insect body part into a target aqueous body where the insect propagates, and thereby controlling insect larval populations by interrupting the insect life cycle. Such insects include, but are not limited to, mosquitoes, grasshoppers, true bugs, flies, fleas, bees, wasps, ants, lice, moths, and beetles, or any member of *Arthropoda*. According to one embodiment, the insect population comprises a peridomestic insect population. According to one embodiment, the insect comprises an oviposition-seeking insect. According to one embodiment, the insect comprises a mating insect. According to one embodiment, the insect comprises an insect seeking aggregation behavior. According to one embodiment, the insect comprises an insect engaged in feeding. According to one embodiment, the insect comprises an insect engaged in overwintering. According to one embodiment, the insect comprises an insect engaged in foraging.

According to one embodiment, the gel formulation of the composition comprises an oil based composition of the active ingredient. According to one embodiment, the active ingredient comprises an insecticide. According to one embodiment, the insecticide comprises an insect growth regulator. According to one embodiment, the insect growth regulator comprises pyriproxyfen. According to one embodiment, the insect growth regulator comprises a pyrethroid.

According to one embodiment, the gel formulation of the composition comprises an active ingredient at a concentration at least about 1% to at least about 50% by weight of the composition. According to one embodiment, the gel formulation of the composition comprises an active ingredient at a concentration of at least about 1% by weight of the composition. According to one embodiment, the gel formulation of the composition comprises an active ingredient at a concentration of at least about 2.5% by weight of the composition. According to one embodiment, the gel formulation of the composition comprises an active ingredient at a concentration of at least about 5% by weight of the composition. According to one embodiment, the gel formulation of the composition comprises an active ingredient at a concentration of at least about 7.5% by weight of the composition. According to one embodiment, the gel formulation of the composition comprises an active ingredient at a concentration of at least about 10% by weight of the composition. According to one embodiment, the gel formulation of the composition comprises an active ingredient at a concentration of at least about 15% by weight of the composition. According to one embodiment, the gel formulation of the composition comprises an active ingredient at a concentration of at least about 20% by weight of the composition. According to one embodiment, the gel formulation of the composition comprises an active ingredient at a concentration of at least about 25% by weight of the composition. According to one embodiment, the gel formulation of the composition comprises an active ingredient at a concentration of at least about 30% by weight of the composition. According to one embodiment, the gel formulation of the composition comprises an active ingredient at a concentration of at least about 35% by weight of the composition. According to one embodiment, the gel formulation of the composition comprises an active ingredient at a concentration of at least about 40% by weight of the composition. According to one embodiment, the gel formulation of the composition comprises an active ingredient at a concentration of at least about 45% by weight of the composition. According to one embodiment, the gel formulation of the composition comprises an active ingredient at a concentration of at least about 50% by weight of the composition.

Exemplary insecticides that can be incorporated in gel formulations of the present invention are listed in U.S. Pat. No. 4,690,775, the entire contents of which are incorporated herein by reference. Such insecticides include but are not limited to organo-phosphates, such as parathion, malathion, diazinon, dichlorvos, Guthion®, Bidrin®, ronnel and tetraethyl pyrophosphate (TEPP), carbamates such as physostigmine, neostigmine, isolan, dimetann, dimetilan, pyrolan, pyramat, Sevin®, Zectran®, Mesurol® and carbaryl; DDT and related chlorinated diphenyl methanes, ethanes, propanes and butanes; cyclodienes such as chlordane, heptachlor, aldrin, dieldrin, Thiodan®, telodrin, camphene, Toxaphene®, rotenoids such as piperonyl butoxide, sesamin allethrolone; organic fluoride compounds, such as fluoroacetamide derivatives; nicotinoids such as nicotine, anabasine, diparcol, demethyl-cotinine, nicotyrine; hexachlorocyclohexanes such as lindane; chlorinated phenols and naphthols; and 4,6-dinitro-o-cresol and related compounds and like.

According to one embodiment, the gel formulation of the composition comprising at least one active ingredient is released from an insect body part into a target aqueous body where the insect propagates. According to one embodiment, the release is immediate. According to one embodiment, the release is followed by immediate dispersal of the gel formulation of the composition in the target aqueous body where the insect propagates. According to one embodiment, the release results in controlling the insect larval population by interrupting the insect life cycle. According to one embodiment, the at least one active ingredient comprises an insecticide. According to one embodiment, the target aqueous body comprises a water holding container. According to one embodiment, the target aqueous body comprises a larval habitat.

According to one embodiment, the at least one active ingredient is present at a concentration that is effective in causing a biological effect, e.g., preventing larvae from developing into adulthood. According to another embodiment, the at least one active ingredient is present at a concentration effective to cause killing of at least 60%, at least 65%, at least 70%, at least 75%, at least 80%, at least 85%, at least 90%, at least 95%, at least 96%, at least 97%, at least 98% o, at least 99% or 100% of the larval population in the target aqueous body by release from a single contaminated gravid female insect. According to another embodiment, the at least one active ingredient is present at a concentration effective to cause killing of at least 60% of the larval population in the target aqueous body by release from a single contaminated gravid female insect. According to another embodiment, the at least one active ingredient is present at a concentration effective to cause killing of at least 65% of the larval population in the target aqueous body by release from a single contaminated gravid female insect. According to another embodiment, the at least one active ingredient is present at a concentration effective to cause killing of at least 70% of the larval population in the target aqueous body by release from a single contaminated gravid female insect. According to another embodiment, the at least one active ingredient is present at a concentration effective to cause killing of at least 75% of the larval population in the target aqueous body by release from a single contaminated gravid female insect. According to another embodiment, the at least one active ingredient is present at a concentration effective to cause killing of at least 80% of the larval population in the target aqueous body by release from a single contaminated gravid female insect. According to another embodiment, the at least one active ingredient is present at a concentration effective to cause killing of at least 85% of the larval population in the target aqueous body by release from a single contaminated gravid female insect. According to another embodiment, the at least one active ingredient is present at a concentration effective to cause killing of at least 90% of the larval population in the target aqueous body by release from a single contaminated gravid female insect. According to another embodiment, the at least one active ingredient is present at a concentration effective to cause killing of at least 95% of the larval population in the target aqueous body by release from a single contaminated gravid female insect. According to another embodiment, the at least one active ingredient is present at a concentration effective to cause killing of at least 96% of the larval population in the target aqueous body by release from a single contaminated gravid female insect. According to another embodiment, the at least one active ingredient is present at a concentration effective to cause killing of at least 97% of the larval population in the target aqueous body by release from a single contaminated gravid female insect. According to another embodiment, the at least one active ingredient is present at a concentration effective to cause killing of at least 98% of the larval population in the target aqueous body by release from a single contaminated gravid female insect. According to another embodiment, the at least one active ingredient is present at a concentration effective to cause killing of at least 99% of the larval population in the target aqueous body by release from a single contaminated gravid female insect.

According to one embodiment, the target aqueous body holds from about 10 ml to about 2 gallons of water. According to one embodiment, the target aqueous body holds about 10 ml of water. According to one embodiment, the target aqueous body holds about 50 ml of water. According to one embodiment, the target aqueous body holds about 100 ml of water. According to one embodiment, the target aqueous body holds about 250 ml of water. According to one embodiment, the target aqueous body holds about 500 ml of water. According to one embodiment, the target aqueous body holds about 750 ml of water. According to one embodiment, the target aqueous body holds about 1 liter of water. According to one embodiment, the target aqueous body holds about 2 liters of water. According to one embodiment, the target aqueous body holds about 3 liters of water. According to one embodiment, the target aqueous body holds about 3.5 liters of water. According to one embodiment, the target aqueous body holds about 0.5 gallon of water. According to one embodiment, the target aqueous body holds about 1 gallon of water. According to one embodiment, the target aqueous body holds about 1.5 gallons of water. According to one embodiment, the target aqueous body holds about 2 gallons of water.

A skilled artisan would appreciate that a single autodissemination apparatus of the present invention can contaminate a plurality of gravid female insects visiting the apparatus. Similarly, a plurality of the autodissemination apparati dispersed in a given location can contaminate multiples of the plurality of gravid female insects visiting the apparati. It follows that a plurality of contaminated gravid female insects would cause killing of the larval population in larger target aqueous bodies. All of the above embodiments are included within the scope of the claimed invention.

According to one embodiment, the apparatus comprises: (1) a cap component, wherein the cap component comprises (i) a plurality of entrances, and (ii) a plurality of auto-filling holes; (2) a cup component, wherein the cup component comprises (i) a water absorbing gel; (ii) a plurality of overflow protection holes, and (iii) a weighted base; (3) a mesh component. According to one embodiment, the mesh component comprises at least one active ingredient. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) a plurality of portal arms, each containing an opening or portal for entry or exit, and (iii) a plurality of auto-filling holes; (2) a cup component, wherein the cup component comprises (i) a reservoir component containing water; and (ii) a plurality of overflow protection holes; and (3) a mesh component. According to one embodiment, the cap component comprises at least three portal arms. According to some such embodiments, the mesh component is coated with the gel formulation of the composition comprising at least one ingredient. According to one embodiment, the mesh component is the primary platform for transfer of the gel formulation of the composition comprising at least one ingredient to an insect.

According to one embodiment, the apparatus comprises: (1) a cap component, wherein the cap component comprises (i) a transfer chamber; (ii) at least one horizontal entrance opening; (iii) a plurality of vertical window openings; (iv) a plurality of window shields, each coated on its inner surface with pyriproxyfen, each covering a vertical window opening and containing an exit opening; (v) a unidirectional funnel and (vi) a plurality of auto-filling holes; (2) a cup component, wherein the cup component comprises (i) a reservoir component containing water; and (ii) a plurality of overflow protection holes; and (3) a mesh component. According to one embodiment, the autodissemination apparatus further comprises (4) a gel formulation of a composition for management of insect populations, the gel formulation of the composition comprising at least one active ingredient for management of insect populations. According to some such embodiments, the horizontal entrance opening is located on the top of the cap component. According to some such embodiments, the horizontal entrance opening has a circumference smaller than the circumference of the base of the cup component. According to some such embodiments, the vertical window opening is smaller than the horizontal entrance opening. According to one embodiment, the cap component comprises at least one horizontal entrance opening. According to one embodiment, the cap component comprises a plurality of vertical window openings. According to one embodiment, the cap component comprises at least two vertical window openings. According to one embodiment, the cap component further comprises at least one window shield covering a vertical window opening. According to some such embodiments, the at least one window shield is made of transparent, translucent or semi-translucent plastic of similar characteristics as acrylic, polycarbonate or the like. According to one embodiment, the at least one window shield contains an exit opening. According to one embodiment, the at least one window shield is coated on its inner surface with the gel formulation of the composition comprising at least one active ingredient. According to some such embodiments, the coated inner surface of the at least one window shield is the primary platform for transfer of the at least one active ingredient to the insect.

According to one embodiment, the apparatus further comprises an insect attractant. Exemplary insect attractants that can be used in one embodiment of the apparatus of the present invention include but are not limited to chemical attractants, such as pheromones, and physical attractants, such as visual lures, for example as disclosed in Weinzierl, R. et al, "Insects Attractants and Traps", Publication no. ENY-277, Alternatives in Insect Management by the Office of Agricultural Entomology, University of Illinois at Urbana-Champaign), one of a series of the Entomology and Nematology Department, Florida Cooperative Extension Service, Institute of Food and Agricultural Sciences, University of Florida. First published: June 1995. Revised: June 2005, the entire contents of which are incorporated herein by reference.

According to one embodiment, the cup component further comprises an insect attractant. According to one such embodiment, the insect attractant is a substrate for bacterial growth. According to one such embodiment, the cup component further comprises a microbial population. According to one such embodiment, the microbial population produces an insect attractant. According to one such embodiment, the insect attractant is a chemical attractant.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any method and materials similar or equivalent to those described herein can also be used in the practice or testing of the present invention, the preferred methods and materials are now described.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be considered as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Autodissemination of an Insect-Growth Regulator for Insect Management Apparatus—Exemplary Design 1

Figure 1:
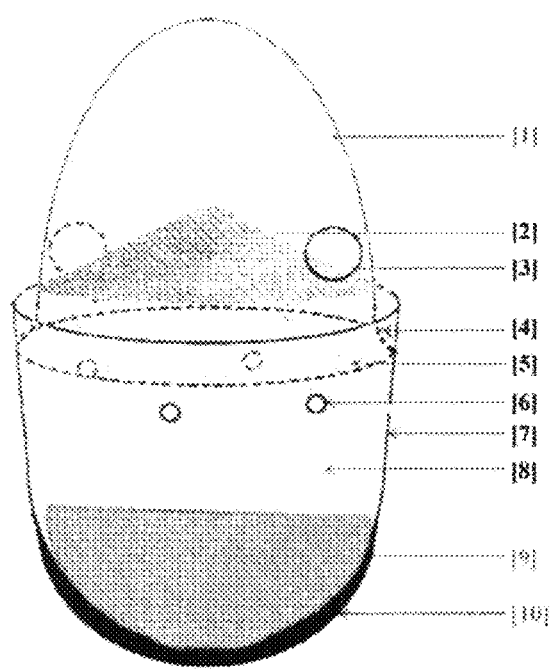

An autodissemination of an insect-growth regulator for insect management apparatus was constructed. Referring to FIG. 1, the apparatus includes a conical-shaped cap component [1] which encloses a cotton fabric mesh component [2]. This mesh component is coated with pyriproxyfen, or other suitable insect-growth regulator. The cap component further contains (i) a plurality of entrances [3], which allow entry by mosquitoes into the cap component at points above the mesh component, and (ii) a plurality of auto-filling holes [5] that are at points below the mesh component. The cap component is mated to a cup component [7]. As the cap component has a slightly smaller diameter than the cup component, when the two components are mated, a trough [4] is formed between the cap component and the cup component. This trough allows for collection of rainwater that then can enter the cup component through the plurality of auto-filling holes in the cap component. The water that enters the cup component then associates with a water absorbing gel [9], such as, for example, a saponified starch-graft polyacrylonitrile copolymer. Upon contact with water, this material swells into a gel, absorbing hundreds of times its own weight in moisture. Thus, the gel can assist in conserving water and thereby extend the duration of mosquito attraction to the station. The base component further comprises a plurality of overflow protection holes [6] at points above the water reservoir [8] which allow for overflow water to escape from the apparatus if required. A weight-supported base [10] of the cup component assists with positional stability of the apparatus.

Example 2. Autodissemination Apparatus—Exemplary Design 2

A prototype autodissemination station to topically contaminate oviposition-seeking mosquitoes was developed consisting of two main sections: a bottom water reservoir and an upper transfer chamber. FIG. 2 shows an image and schematic drawing for a prototype autodessemination station. The sections were constructed by molding wet shredded cardboard with corn starch as a binder, a technology commonly used in the manufacture of disposable plant containers. Peat moss, egg cartons, rice hulls, newspaper, straw, natural polymers, and other materials and binders can also be used.

The reservoir component [20] is flask-shaped to maximize water-holding capacity (e.g. 600 ml). The reservoir's role is to present a lure (water) to attract gravid females. The reservoir also holds an organic food substrate (e.g., dried shredded oak leaves, yeast, rabbit pellets, etc.) for bacteria that produce volatile cues females use in oviposition sites selection (Ponnusamy, P., Xu, N., Nojima, S., Wesson, D. M., Schal, C. & Apperson, C. S. (2008) Identification of bacteria and bacteria-associated chemical cues that mediate oviposition site preferences by Aedes aegypti. *Proceedings of the National Academy of Sciences*, vol. 105, pp. 9262-9267). The food substrate was secured within a bag [21] constructed from tubular cotton gauze (Surgitube®, Surgitube Corp., Bronx N.Y. USA) and the bag fixed with paraffin to the reservoir bottom [22]. This bag design prevents food particles from obstructing the overflow holes [17] when the unit is flooded, yet nutrient release is unimpeded.

The base of the transfer chamber [13] was designed to friction-fit within the rim [18] of the reservoir [20]. The reservoir rim is slightly larger in diameter and slips several millimeters over the transfer chamber rim where the difference in diameters creates a shallow gutter [14] between reservoir and chamber. The gutter collects runoff water from the chamber, which is dome shaped to enhance rainwater and dew capture. The bottom edge of the transfer chamber [13] is scalloped to generate multiple holes that drain water from the gutter into the reservoir. End-users may elect to fill the reservoir with tap water when the station is deployed or alternatively permit the reservoir to be auto-filled with rainfall. The auto-fill feature is projected to increase the duration of attraction. A row of overflow holes [17] near the top edge of the reservoir prevent excess water from breaching the reservoir and entering the transfer chamber.

The transfer chamber holds an insecticide-impregnated cotton mesh fabric (86 $cm^2$, 39 openings/cm) [15] fashioned into a shallow cone and secured within the chamber base. The mesh is the primary platform for pyriproxyfen transfer from the station to searching gravid mosquitoes. The transfer mesh is washed to induce fraying, increasing the surface area available for toxicant loading. A secondary function of the mesh is to serve as a barrier to prevent mosquitoes from entering the reservoir. The cone shape of the transfer mesh provides additional surface area for pyriproxyfen loading and mosquito searching, as well as reducing prospects of mosquitoes exiting the transfer chamber without contacting the mesh. The overflow and gutter auto-fill holes are sufficiently large for water, but not for mosquito passage.

The transfer chamber has three portal arms [12a] each portal arm containing an opening or portal (4 cm diameter) [12b] for mosquito entry and exit. The extruded shape of the portals buffers the mesh and adhering chemical from abiotic (e.g., rain, wind, light) and biotic (e.g., children, pets, wildlife) contact.

The station is coated with paraffin wax to waterproof and extend the unit's life. The unit is designed, however, to breakdown after a single mosquito season or approximately four months for *Ae. albopictus* in New Jersey. The station's effective lifespan is proscribed by adjusting the thickness of the wall and wax coat. The inner surface of the transfer chamber is not wax coated. Because a dark, humid interior may be attractive to resting mosquitoes, this inner surface is dusted with pyriproxyfen as a secondary platform for toxicant transfer. The station is dyed a dark grey with ink.

Consideration was given to the need for the station to remain stable and upright when challenged by wind, animal and human activity, since being knocked over inactivates the unit by purging the lure. Foremost, the unit is best placed in protected, low traffic areas near vegetation that provides the shade favored by container-dwelling species in oviposition site selection (Vezzani, D. et al., 2009, "The effect of shade on the container index and pupal productivity of the mosquitoes *Aedes aegypti* and *Culex pipiens* breeding in artificial containers." Medical and Veterinary Enzymology, 23:78-84). The reservoir has a wide, flat bottom to assist the unit in maintaining an upright position. Sand embedded in the floor adds weight that also assists in stability. A cotton string implanted at the station apex permits the unit to be suspended above ground.

Example 3. Autodissemination Apparatus

Exemplary Design 3—Windows Autodissemination Station

Figure 3:
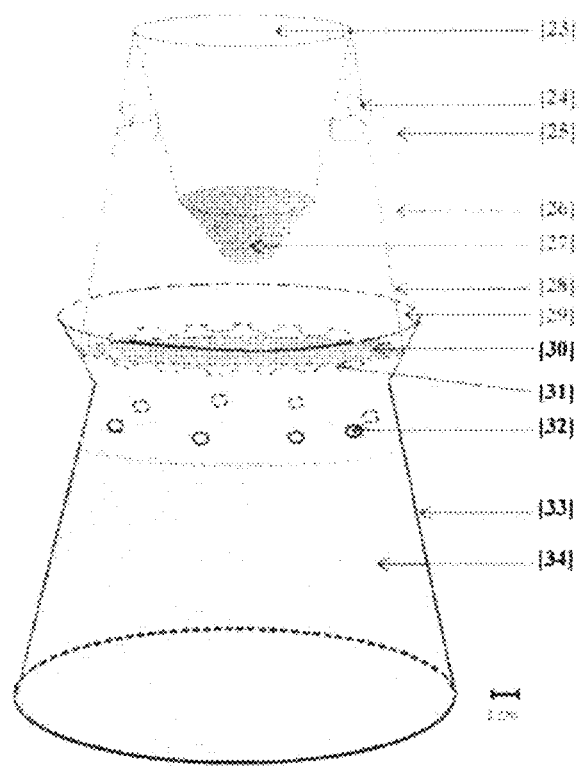

A windows autodissemination station (WADS) design consists of two major components: a reservoir and a transfer chamber. FIG. 3 shows a schematic of the WADS design. The lower reservoir chamber [33] is identical to designs 1 and 2. The upper transfer chamber [28] features a unidirectional mesh funnel and two pyriproxyfen-coated window shields [25] made of translucent plastic material covering two vertical window slits [24]. The unidirectional funnel allows the female mosquitoes seeking water for egg laying to enter the chamber through a horizontal entrance on top of the transfer chamber, but prevented from exiting back through the top entrance and/or reaching the water-filled reservoir chamber [33] on the bottom. The WADS design forces the mosquitoes unable to reach the water to try to escape via the vertical window openings due to their attraction of light. Exiting mosquitoes are thereby forced to walk on the inner surface of window shields, coated on the inner surface with pyriproxyfen, which is therefore transferred to mosquito legs. The WADS design minimizes pyriproxyfen or any other insecticide usage to a small restricted area. Further, the WADS design exploits female mosquito behavior seeking a dark, cryptic habitat to lay their eggs and then seeking light to escape the station.

Example 4. Method of Preparing a Gel Formulation for Autodissemination

A gel formulation of a composition comprising pyriproxyfen was prepared by the following method. Technical pyriproxyfen (400-600 mg) was dissolved in a sticking agent, such as corn oil (1.5 mL-2.5 mL) with continuous magnetic blending in a 250 mL glass beaker. Upon complete dissolution, an emulsifying agent/surfactant (1.5 mL-2.5 mL), such as Tween 80 was added to the solution with continuous blending for an additional 3 min. An emulsifying agent/surfactant, such as petroleum jelly (2 g-5 g) was then added to the solution with magnetic blending for 10 min, followed by hand mixing with a stainless steel spatula for an additional 10 min to yield a gel emulsion. Additional particulate ingredients, such as silica powder (1 g-2 g) and talc powder (1 g-2 g) and/or a combination thereof were then optionally added to the gel emulsion with continuous hand mixing with a stainless steel spatula for 5 min to yield a uniformly mixed gel formulation. The gel formulation was then stored in a 250 mL glass bottle at 4° C. for future use.

Example 5. Gel Formulation I

Gel formulation I was prepared by the method explained in Example 1 using 480 mg Technical Pyriprophen in 2.5 g petroleum jelly, 2 ml corn oil, 2 ml an emulsifying agent with 1.5 g silica powder (0.5 µM-10 µM) and 1.5 g talc powder (0.5 µM-10 µM).

Example 6. Gel Formulation II

Gel formulation II was prepared by the method explained in Example 1 using 480 mg Technical Pyriprophen in 4 g petroleum jelly, 2 ml corn oil, and 2 ml emulsifying agent without any additional ingredients.

Example 7. Powder Formulation I

Powder formulation I, used as a comparative control, was prepared by the method similar to one explained in Example 1, but without using an emulsifying agent. Powder formulation I was prepared using 490 mg Technical Pyriprophen in 0.4 ml corn oil, 1 ml an emulsifying agent with 3.7 g silica powder (0.5 µM-10 µM).

Example 8. Powder Formulation I

Powder formulation II, used as a second comparative control, was prepared by the method similar to one explained in Example 4, but without using an emulsifying agent. Powder formulation II was prepared using 490 mg Technical Pyriprophen in 0.4 ml Corn Oil, 1 ml an emulsifying agent with 2.0 g talc powder (0.5 µM-10 µM).

Example 9. Use of Authodessimination Station

Materials and Methods
Station Design.
Exemplary design 2 was used.
The transfer chamber comprised an insecticide-impregnated cotton mesh fabric (86 cm$^2$, 39 openings/cm) fashioned into a shallow cone and secured within the chamber base. The mesh was the primary platform for pyriproxyfen transfer from the station to searching gravid mosquitoes. The transfer mesh was washed to induce fraying, increasing the surface area available for toxicant loading. FIG. 4 shows a micrograph, obtained with a compound microscope (Olympus SZX16, Japan) and a digital camera (ProgRes CF Scan, Jenoptic, Germany), showing a transfer mesh (platform for insect growth regulator transfer to adult mosquitoes entering an autodessimination station) uncoated (FIG. 4A) and coated (FIG. 4) with pyriproxyfen-impregnated silica particles.

Laboratory Colony.
Larvae of *Ae. albopictus* for bioassays were obtained from a colony established from eggs collected in Mercer County, N.J., U.S.A. in 2008 and supplemented during 2009 and 2010. The colony was maintained at 26° C. and a relative humidity of 75% with a 16L:8D photoperiod. Adults were held in 30×30×30 cm aluminum screen cages and supplied with 10% sucrose solution on cotton wicks. Restrained guinea pigs were used to blood feed females and subsequent eggs were collected on seed germination paper and stored at 26° C. Eggs were hatched as needed by flooding egg papers and the larvae held in enamel trays with 1 liter of deionized water and 0.15 g of Brewer's yeast: lactalbumin (50:50). Third instars were used in all bioassays.

Attraction of Gravid Females.
The attractiveness of the station design was tested against alternate oviposition sites in 1.3×1.3×1.3 m cages covered with cotton mesh. Each cage held an autodissemination station and two 360 ml capacity black oviposition cups (experimental lethal ovitrap cups lacking toxicant from SpringStar Inc., Woodinville, Wash. USA), each containing 200 ml of oak infusion water as a lure to attract gravid female (Trexler, J. et al., 1998, "Laboratory and field evaluations of oviposition responses of *Aedes albopictus* and *Aedes triseriatus* (Diptera: Culicidae) to oak leaf infusions", Journal of Medical Entomology, 35:967-976). The station and ovicups were placed equidistant apart at 80 cm with a sucrose solution at the cage center. A 5 cm wide strip of Whatman No. 1 filter paper lined the inner wall of the station reservoir and the cups, with the bottom 3 cm submerged into the infusion and the upper 2 cm portion available for oviposition. The transfer mesh was not inserted into the station so females could access the oviposition paper. No pyriproxyfen was used. Twenty gravid *Ae. albopictus* were introduced into each cage. After 48 hr, the eggs on each paper strip as well as any deposited on the water surface were counted. The experiment was repeated three times with three replicates (cages) per experiment at 21-27° C., 60-75% RH, and a 16L:8D photoperiod. Egg deposition in the station and ovicups was compared with one-way ANOVA (<0.05) using Least Significant Difference (LSD) among the means.

Formulation.

The source of pyriproxyfen for all experiments was a mixture of technical compound and NyGuard® IGR (10% a.i.) (2-[1-methyl-2-(4-phenoxyphenoxy) ethoxy] pyridine), from MGK Chemical Co (Minneapolis, Minn., U.S.A.) as an emulsifiable concentrate. The technical permitted high loading of active ingredient, whereas the commercial product provided a source of emulsion to aid pyriproxyfen release when contaminated females made contact with water. A formulation was prepared for each station with 500 mg of silica particles (silicon dioxide, 3-30μm diameter), 500 mg of technical pyriproxyfen, 200 μl of the NyGuard® EC 10, and 200 μī corn oil as a sticker. The technical compound was dissolved in 3 ml of reagent grade acetone before mixing with the other components. Air drying the mixture at room temperature for 24 hr resulted in a powder formulation of pyriproxyfen-impregnated particles.

The powder was used to treat the transfer mesh and inner wall of the transfer chamber. To enhance adherence of the powder, these surfaces were first lightly brushed with corn oil. The mesh was blotted to remove excess oil, whereas this was unnecessary for the chamber wall due to absorbance. The mesh was then attached to the chamber, the chamber inverted, the pyriproxyfen powder added, the chamber sealed with plastic film, and then agitated to distribute the powder before joining the transfer and reservoir chambers. Each station was treated with 520 mg of active ingredient at a concentration of 1.63 mg/cm.

Transfer from Station to Females.

Station effectiveness in transferring pyriproxyfen powder to visiting females was tested by counting the particles attached to individual test mosquitoes. Forty gravid females were introduced into pyriproxyfen-treated station, the entrances blocked, and the station placed into a cubic 2.2 m screened cage provisioned with sucrose solution. The station portals were reopened after 30 min, permitting the mosquitoes to quickly exit the station and enter the cage. The station was then removed. Five gravid females were individually captured with an aspirator after 0, 1, 2, 6, 12, 24, and 48 hr, transferred into centrifuge tubes, and killed by freezing at $-4°$ C. for 4 hr. The mosquitoes were placed into individual 200 μī drops of 0.1% detergent (Sparkleen®, Fisher Scientific, Pittsburgh, Pa. USA) to remove adhering powder, and the retrieved particles counted. The experiment was replicated three times with environmental conditions of 26-28° C., 60-75% RH, and 16L:8D photoperiod. To assess whether transfer efficacy from the station would be reduced as the formulation aged due to water sorption, the work was repeated with stations placed in a 100% RH environment for 7 d.

Transfer from Females to Larval Habitat.

The efficacy of pyriproxyfen-contaminated females in transferring lethal concentrations of the toxicant to water-holding containers (i.e., larval habitats) was tested in cage and small room experiments. A 10% sucrose solution was provided in all tests.

In the cage experiment, an autodissemination station equipped with a pyriproxyfen-treated transfer mesh and 450 ml of oak leaf infusion water was centered in a cubic 2.2 m$^3$ cage. A 360 ml capacity plastic cup was placed in each cage corner 15 cm from the walls. Each of the four cups was filled with 200 ml tap water and oviposition paper strips aligned as described above. Controls used a station with an untreated transfer mesh. Fifty gravid females were then introduced into the cage. After five days, the test was terminated, oviposition papers and eggs discarded, and containers were removed and the water assessed for pyriproxyfen transfer by larval bioassay (see 'insecticide bioassays' below). There were three treatment and one control cage per experiment and the experiment was repeated three times, providing a total of 36 test and 12 control ovicups for bioassay. Environmental conditions were 21-28° C., 60-75% RH, and a 16L:8D photoperiod.

In the room trial, the test arena was scaled-up to a larger area with dimensions of 2.1 (W)×2.6 (H)×5.7 (L) m (31.1 m$^3$). A station was placed in the center of the room and ovicups with oak infusion and ovistrips were positioned at each corner 30 cm from the walls. Fifty gravid females were introduced for a five day test. The ovistrips and eggs were discarded and the water from each container was tested for insecticidal activity by larval bioassay, with four additional untreated cups as controls. Environmental conditions of 26-28° C., 60-75% RH, and 16L:8D photoperiod. Inhibition of emergence in the cage and room trials was analyzed against their respective controls with a t-test ($P \leq 0.05$).

Venereal Transfer.

This experiment determined whether contaminated mosquitoes could transfer pyriproxyfen to uncontaminated individuals via mating behaviors. To ensure virginity, pupae were individually transferred to 50 ml centrifuge tubes until emergence, and then caged by gender before testing 5-7 days post-emergence. Adult males were exposed to pyriproxyfen-treated filter paper (8×10 cm Whatman No. 1) lining a 50 ml test tube. The paper was coated with 1.5 ml of corn oil as a sticker, blotted to remove excess oil, and then dusted with our pyriproxyfen powder formulation at 0.26 mg/cm of a.i. After ten minutes of exposure, males were transferred from the tube by aspirator to mating containers (450 ml capacity, 7.5 cm depth) covered with mosquito-proof mesh, and allowed to mate with uncontaminated females in pairs. After 48 hr, females were collected by aspirator from cage sides and transferred briefly to a holding container (450 ml plastic container), before a second transfer to individual oviposition chambers (two 450 ml containers joined with tape to form an enclosure) holding 200 ml of tap water and lined with an oviposition paper. The upper portion of the oviposition chamber was perforated for aeration and a portal was provided for cotton wicks used in sugar feeding. The dual transfer increased handling but reduced prospects for inadvertent transfer of pyriproxyfen to the chambers. Environmental conditions were 25-29° C., 60-75% RH, and 16L:8D photoperiod. Oviposition chamber water was collected after five days and assayed for inhibition of adult emergence using methods described below. The experiment was repeated twice with three replicates each. T-test was used to test for significant differences ($p < 0.05$).

Insecticide Bioassays.

All insecticidal activity tests were conducted in adult emergence units—450 ml plastic containers with a screen-covered lid and 200 ml of water (water lost via evaporation was replaced before assay). Each container held twenty 3rd instar *Ae. albopictus*. Test containers were incubated at 26° C. and 16L:8D photoperiod. At 2-day intervals, ground rat chow (30 mg/L) was provided as food, water lost due to evaporation was replenished, dead and emerged individuals were removed, and successful adult emergence was recorded. Incomplete emergence or adults with attached exuviae were recorded as dead.

Results & Discussion

The first criterion for an autodissemination station is effectiveness at luring the target insect. Earlier designs did not compete effectively with ovicups for the attention of females. Attraction increased, however, with subsequent designs that increasingly simulated tree holes in portals, texture, color, etc. Later designs were successful in attracting gravid females as in our cage experiment we found no difference in the proportion of eggs recovered from the station (mean±SE=38.25±4.63%) compared against two competing ovicups (34.04±3.12 & 27.71±4.15%) (df=2, F=1.15, p=0.33).

The station's efficacy in suppressing container-dwelling mosquitoes rests heavily on its ability to compete with the numerous artificial containers characteristic of urban environments. An exemplary main target, *Ae. albopictus*, is a highly anthropophilic and ecologically flexible species that has adapted from tree holes to colonize discarded tires, bird baths, flower pots and saucers, vases, rain gutters, tarps, catch basins, cemetery urns, toys, cans and trash (Hawley, W. A., 1988, "The biology of *Aedes albopictus*", Journal of the American Mosquito Control Association, Supplement 1: 1-40).

Although the oak leaf infusion we tested was effective in attracting *Ae. albopictus* females, the response of gravid container-dwelling species to organic infusions varies with the plant species, biomass and duration of fermentation (Ponnusamy, P. et al., 2010, "Oviposition responses of the mosquitoes *Aedes aegypti* and *Aedes albopictus* to experimental plant infusions in laboratory bioassays", Journal of Chemical Ecology, 36:709-719). Optimal attraction to the station will require species-specific attractants.

The second criterion for autodissemination is toxicant transfer to the target insect which will disperse the agent. The station has design elements to maximize transfer. Whereas the reservoir attracts females, the transfer mesh prevents visiting females from reaching the water and ovipositing. This serves dual functions. Most importantly, visiting females searching unrewardingly for a conduit to the water below will maximize visit time, contact with the mesh, and presumably toxicant loading. Because egg compliment is undiminished, females must visit additional proximal larval habitats, providing more opportunities to transmit the chemical. And, because oviposition in the station is precluded, the station will not reach a threshold of egg deposition that deters females.

The powder formulation proved effective in initial attachment to *Ae. albopictus* females. Microscopic examination demonstrated that particles adhered topically to every body part, including the tarsi and tip of the abdomen. FIG. 5 shows a micrograph, obtained with a compound microscope (Olympus SZX16, Japan) and a digital camera (ProgRes CF Scan, Jenoptic, Germany), showing an abdomen (FIG. 5A) and a foreleg tarsi (FIG. 5B) showing adherence of pyriproxyfen-impregnated particles (arrows) to *Aedes albopictus* female mosquitoes. These are the locations most likely to make contact with container water and release the insecticide. An average of 65.5±6.92 particles per female were counted from mosquitoes exiting the station and flying to the cage netting before being captured. Powder was lost over time, declining to 40.3±3.84, 29.3±4.13, 22.0±1.78, 5.5±0.96, 2.0±0.71 0 and 2.2±0.67 particles per female after 1, 2, 6, 12, 24 and 48 hours, respectively. Losses are attributable to a combination of activities including flight, aspiration, and post-capture handling. However, we attributed lost particles in large part to the grooming behaviors frequently observed in the resting females. Walker, E. D. et al. (1988) recorded 12 different grooming behaviors in female *Ae. triseriatus* Say in which tibial combs were used for cleaning (Walker, E. D. et al., 1988, "Sequential organization of grooming behaviors of the mosquito *Aedes triseriatus*", Journal of Insect Behavior, 1: 197-109). Grooming frequency increases when insects are exposed to silica dust (El-Awami, I. O., et al., 1995, "The interaction of surface and dust particle size on the pickup and grooming behavior of the German cockroach Blattella germanica", Entomologia Experimentalis et Applicata, 77:81-87). Although generally disadvantageous for autodissemination, in some circumstances grooming could prove beneficial, notably when resting and oviposition sites converge as in tires.

Powder exposure to high humidity can result in water sorption and plasticization (Fox, P. F., et al., 1998, "Dairy Chemistry and Biochemistry", Kluwer Academic/Plenum Publishers, New York, 479 pp.). The outcome can be 'caking', the change of a powder into a solid mass. Caking would interfere with particulate adherence to visiting mosquitoes and could be a legitimate threat for a station in which continuous exposure to high humidity is an intrinsic condition. Maintaining the station with a full reservoir for a week, however, did not reduce the number of silica powder particulates adhering to mosquitoes or in visible caking. Nevertheless, given the potential significance of caking, factors that impact the water sorption of powders, including formulation components, particle size, and exposure duration must be considered.

The third autodissemination step is toxicant transfer from contaminated individuals to target habitats. In cage experiments, pyriproxyfen-charged stations resulted in 100% inhibition of adult emergence in all 36 ovicups tested whereas control mortality was 6.51±4.72%. The room trial was more challenging by presenting a test arena of 0.62 m$^3$/female or more than 14 times that of the cage study. The increase in area from cage to room was reflected in a reduced level of inhibition achieved: 81.25%±2.39% compared to 10.0±2.04% in the control ovicups. All of the experimental ovicups had been visited by females as the smallest reduction in adult emergence was 75%. These results bolster earlier work with *Ae. aegypti* in demonstrating the potential of mosquitoes as a vehicle to carry pyriproxyfen to larval habitats, and extends the concept to *Ae. albopictus*. (Itoh, 1994, "Utilization of bloodfed females of *Aedes aegypti* as a vehicle for the transfer of the insect growth regulator, pyriproxyfen, to larval habitats", Tropical Medicine, 36; 243-248; Chism, B. D. et al., 2003, "Horizontal transfer of the insect growth regulator pyriproxyfen to larval microcosms by gravid *Aedes albopictus* and *Ochlerotatus triseriatus* mosquitoes in the laboratory", Medical and Veterinary Entomology, 17:211-220; Devine, G. J., et al, 2009, "Using adult mosquitoes to transfer insecticides to *Aedes aegypti* larval habitats", Proceedings of the National Academy of Sciences, USA, 106: 11530-11534).

Transfer of lethal pyriproxyfen concentrations from mosquitoes to water-holding containers was inversely related to time and container volume. Consider time first. Immediately after exiting the station, each female retained an estimated average of 0.524 µg of a.i., which declined to 0.324, 0.234, 0.176, 0.044, 0.016 and 0.018 µg after 1, 2, 6, 12, 24 and 48 hours, respectively. Because the LC$_{50}$ for pyriproxyfen against *Ae. albopictus* is a mere 0.012 ppb (unpublished data), a single mosquito could theoretically transfer lethal pyriproxyfen concentrations into most containers colonized by *Ae. albopictus*. Next, consider container volume. The Asian tiger mosquito prefers small to medium-sized containers (Hawley, W. A., 1988, "The biology of *Aedes albopictus*", Journal of the American Mosquito Control Association, Supplement 1:1-40). Carrieri et al. (2003) found *Ae. albopictus* tended to colonize small containers, even those holding just a few milliliters of water; most (80%) containers had a volume of less than five liters (Carrieri, M. et al., 2003. "On the competition occurring between *Aedes albopictus* and *Culex pipiens* (Diptera: Culicidae) in Italy", Environmental Entomology, 32: 1313-1321). Discarded tires are an important *Ae. albopictus* larval habitat and hold an average of one liter of water (Schreiber, E. et al., 1992, "Surveys on artificial container inhabiting mosquitoes in Sarasota and Tallahassee, Fla. I: characterizations of larval habitats", Journal of the Florida Mosquito Control Association, 63:7-15). Considering time and volume together, it is estimated that if a single contaminated female were to release all adhering pyriproxyfen into a single container, this could induce 50% mortality in containers of 28.3 liters up to six hours after becoming contaminated, declining to 3.5 liters after 12 hours, and 0.13 liters after 24 hours. These estimates are useful only in demonstrating that (1) females contaminated with our current formulation have a limited time span for transferring lethal pyriproxyfen concentrations to larval habitats; and (2) the concentrations of pyriproxyfen potentially to be carried into drinking water would not approach the 300 ppb limit recommended by WHO (2002).

The hypothesis that mating behavior results in venereal transfer was tested and horizontal mechanical transfer of pyriproxyfen powder from contaminated males to virgin females was visually established. FIG. 6 shows a micrograph, obtained with a compound microscope (Olympus SZX16, Japan) and a digital camera (ProgRes CF Scan, Jenoptic, Germany), showing the distal view of a virgin *Aedes albopictus* female (FIG. 6A) and the distal view of a an oviposition-seeking *Aedes albopictus* female (FIG. 6B) showing pyriproxyfen-impregnated particles (arrows) transferred by mating from contaminated males to females. Acquired particles were observed clinging to various body regions, including the tarsi, and were often found attached to the adult female's last two segments (7 and 8), that is the ovipositor. Males first grasp females with the tarsi before swinging their abdomen up. The venter-to-venter position is then assumed with the ovipositor extruded for mating, making these terminal segments particularly vulnerable to mechanical transfer from contaminated males. The ovipositor is then retracted, the normal condition, where a degree of shelter for particulates from grooming is provided. When extruded again, for oviposition site selection and egg deposition, this area can contact water and release the adhering insecticide. In bioassays to assess whether venereally acquired pyriproxyfen could subsequently be transferred to water-holding containers at lethal concentrations, we recorded 48.33±5.87% inhibition of emergence, a significant difference from control mortality of 5.0±1.83% (df=5, t-test value=7.05, p=0.00003).

Venereal transmission of pathogens in mosquitoes, notably infectious viruses including chikungunya (Mavale, M. et al, 2010, "Venereal transmission of chikungunya virus by *Aedes aegypti* mosquitoes (Diptera: Culicidae)", American Journal of Tropical Medicine & Hygiene, 83: 1242-1244); LaCrosse (Thompson, W. H. et al., 1978, "Venereal transmission of LaCrosse virus from male to female *Aedes triseriatus*", American Journal of Tropical Medicine & Hygiene, 27: 187-196), and Sindbis (Ovenden, J. R. et al, 1984, "Venereal transmission of Sindbis virus between individuals of *Aedes australis* (Diptera: Culicidae)", Journal of Medical Entomology, 21:292-295) is well documented and is believed to play a role in the infection cycle. Vail et al. (1993) showed male Indian meal moths contaminated with a powder formulation of a granulosis virus transferred this insect pathogen to adult females during copulation, with larval food subsequently becoming contaminated during oviposition (Vail, P. V. et al., 1993, "Autodissemination of *Plodia interpunctella* (Hiibner) (Lepidoptera: Pyralidae) granulosis virus by healthy adults", Journal of Stored Products Research, 29:71-74). Moya et al. (2010) reported male fruit flies fed the chemosterilant lufenuron subsequently transferred the compound to females. Venereal transference of a chemical insecticide by mechanical means and subsequently to an oviposition site has not been previously reported (Moya, P. et al, 2010, "Evaluation of lufenuron as a chemosterilant against fruit flies of the genus *Anastrepha* (Diptera: Tephritidae)", Pest Management Science, 66:657-663). The contribution of venereal transmission to mosquito population reduction is unclear but might play a significant if modest role as it has been found that males are attracted to oak infusion water, use the station for resting and carry more particles than females (unpublished data).

Key features of one embodiment of an autodissemination station include:

Zero maintenance. The station is a user-friendly station that once deployed into the urban environment requires no further effort over the container-dwelling mosquito season. The unit will replenish the reservoir automatically from rain and dew. Oviposition cannot occur in the station, so there are no oviposition papers to replace as they fill with eggs-container-dwelling mosquitoes tend to shun sites containing eggs of conspecifics (Chadee, D. D. et al., 1990, "Egg-laying yellow fever mosquitoes avoid sites containing eggs laid by themselves or by conspecifics", Entomologia Experimentalis et Applicata, 57:295-298). The toxicant will not have to be refreshed since it shows outstanding persistence under normal field conditions (Sihuincha, M. et al., 2005, "Potential use of pyriproxyfen for control of *Aedes aegypti* (Diptera: Culicidae) in Iquitos, Peru", Journal of Medical Entomology, 42:620-630) and will be buffered from damaging environmental extremes including flushing, sunlight and microbial action within the station. And there is no need for labor-intensive season-end retrieval because the unit is designed to structurally breakdown.

Biodegradable. The station is intended for a single season of use. Components are designed thereafter to degrade (resulting in leaking) and disintegrate into the soil, precluding the unit from becoming a source for mosquito production. A station can also be constructed from nondegradable materials so the station could be reused; however, the unit would need periodic recharging with insecticide or it would become a source.

Low cost. The station must be economical to manufacture so an adequate number of units can be deployed to compete with natural oviposition sites. A cost-of-goods analysis estimates that, considering the inexpensive components required for manufacture, a unit might be produced for less than one dollar (U.S.).

Low Risk. Pyriproxifen is an U.S. Environmental Protection Agency-designated 'low risk' insecticide that is virtually nontoxic to mammals and birds. Containing the chemical within stations bars access to wildlife, pets and children, which reduces risk further. More significantly, mosquito autodissemination requires a small amount of insecticide which precisely targets water-holding containers, and therefore presents less exposure than broadcast sprays used by homeowners and local mosquito control agencies.

High attraction. Every effort was made to enhance the station's ability to lure gravid females and compete with alternate containers. The embodiment of the station simulates a treehole, is provisioned with a food substrate for bacterial growth, and has a water reservoir. The unit was acceptable to females seeking to oviposit in our lab studies.

Extended attraction. The effectiveness of the station depends on maintaining moisture to attract gravid females for the greatest possible duration. Accordingly, the water reservoir is designed to be renewed via rain and dew collection-5.5 cm of rainfall is sufficient to fill the unit. The design also reduces evaporative loss-the station retains water for more than seven weeks at 26° C. and 50% RH. These features will assist the unit in bridging periods of low rainfall and magnify its effectiveness in competing with alternative oviposition sites.

Lethal Ovitrap. Devine and Killeen (2010) identify the key advantages of "lure and disseminate" (i.e., autodissemination) over a "lure and kill" (i.e., lethal ovitrap-Perich et al., 2003) as the potential amplification of coverage at the larval habitat and the use of a chemistry for which resistance has not yet developed. Nevertheless, our station could be modified to kill mosquitoes attempting to oviposit simply by treating the transfer mesh with an adulticide such as a pyrethroid rather than with an IGR. That is, the station could function as a lethal ovitrap because it offers many of the same features including ability to lure gravid females, in addition to new advantages such as extended insecticidal activity, inability to serve as a larval habitat when insecticidal activity fails, the elimination of egg papers, and reduced nontarget exposure to insecticides.

Example 10. Removal of Powder Particulates

Figure 7:
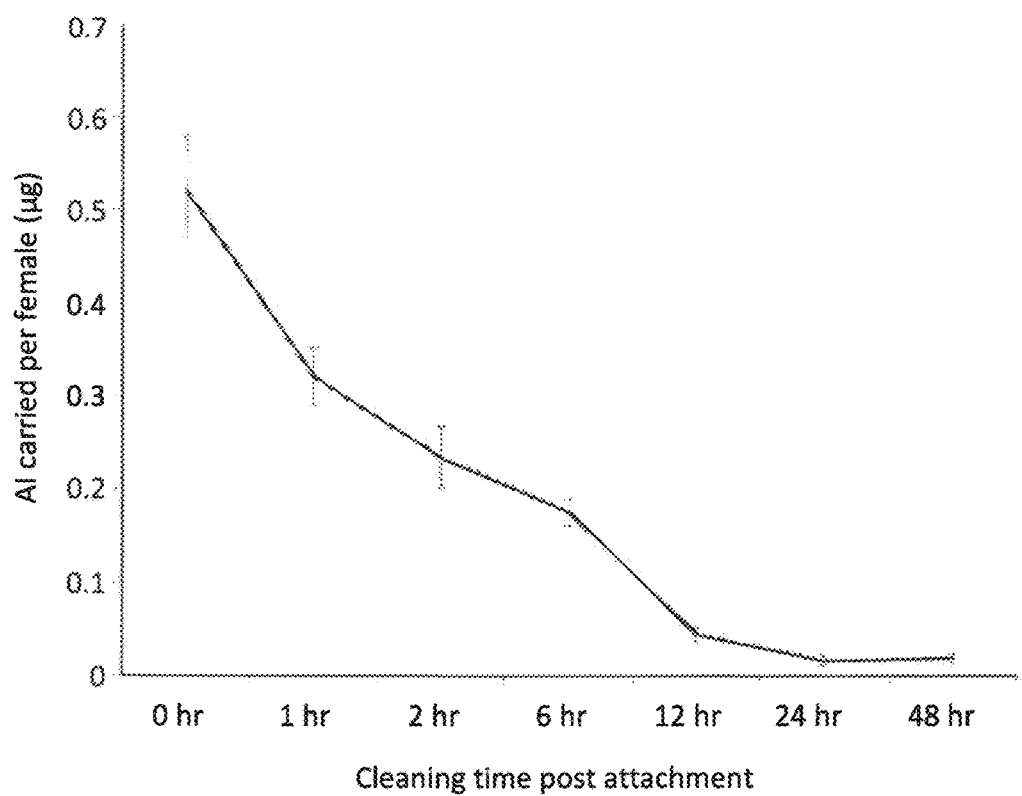
FIG. 7 shows a graphical representation of reduction of active ingredient per female μg/female) with time due to mosquito grooming behavior when using particulate formulations.

This example demonstrates that female mosquitoes are able to remove particulate formulations over time due to their grooming behavior. Forty gravid females were introduced into an autodissemination station charged with powder formulation, the entrances blocked, and the station placed into a cubic 2.2 m screened cage provisioned with sucrose solution. The station portals were reopened after 30 min, permitting the now powder-contaminated mosquitoes to quickly exit the station and enter the cage. The station was then removed. Five gravid females were individually captured with an aspirator after 0, 1, 2, 6, 12, 24, and 48 hr, transferred into centrifuge tubes, and killed by freezing at −4° C. for 4 hr. The mosquitoes were placed into individual 200 µl drops of 0.1% detergent (Sparkleen®, Fisher Scientific, Pittsburgh, Pa. USA) to remove adhering powder, and the retrieved particles counted. The experiment was replicated three times with environmental conditions of 26-28° C., 60-75% RH, and 16L:8D photoperiod. FIG. 7 shows a graphical representation of reduction of active ingredient per female µg/female) with time due to mosquito grooming behavior when using particulate formulations.

Figure 8:
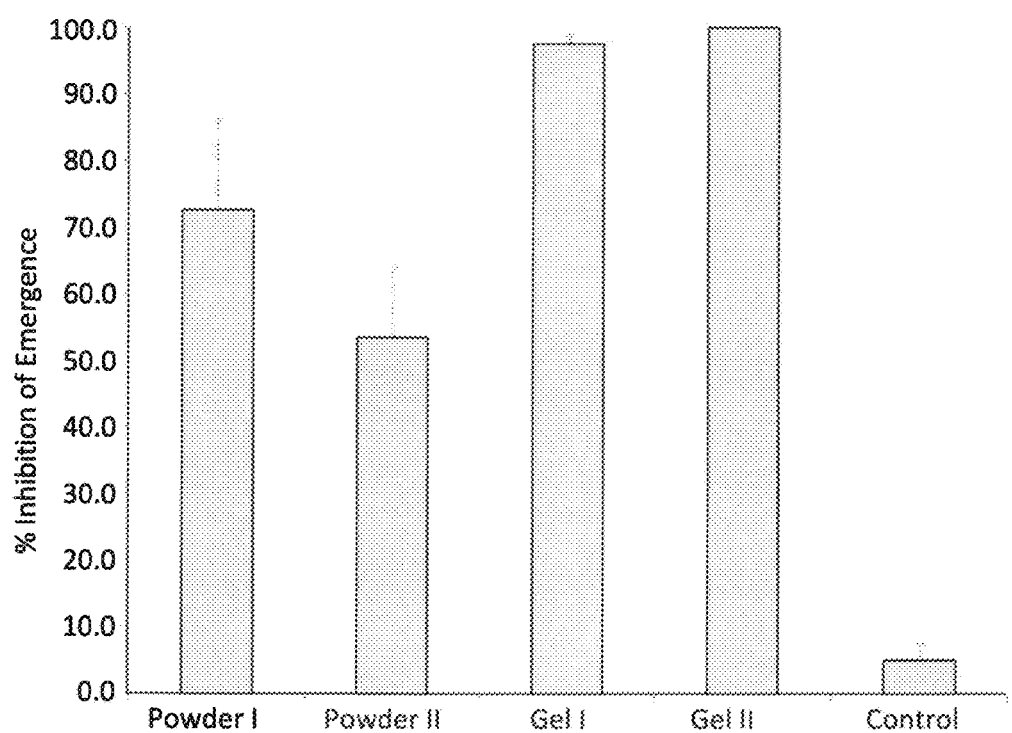
FIG. 8 shows a bar graph representation of percentage inhibition of emergence from autodissemination station with powder formulation I, powder formulation II, gel formulation I and gel formulation II, and a control.
Figure 9A:
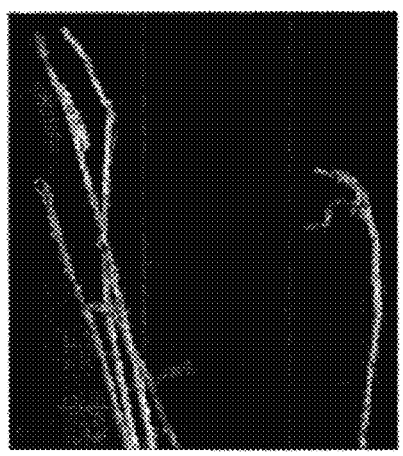
FIGS. 9A-9D shows pictures of mosquito legs under normal (FIG. 9A) and UV light (FIG. 9A, FIG. 9B, FIG. 9C and FIG. 9D) demonstrating effective transfer of gel formulation to legs of mosquitoes visiting autodissemination stations.
Figure 9B:
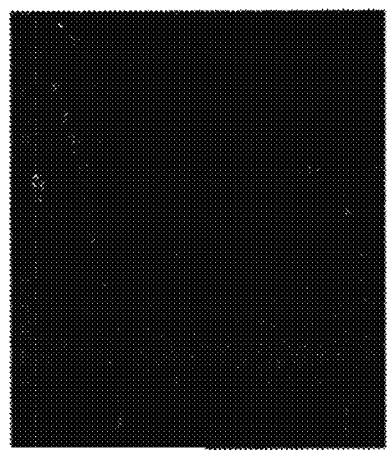
Figure 9C:
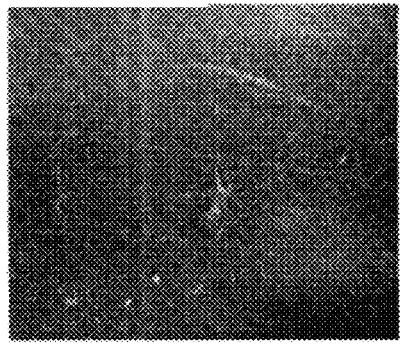
Figure 9D:
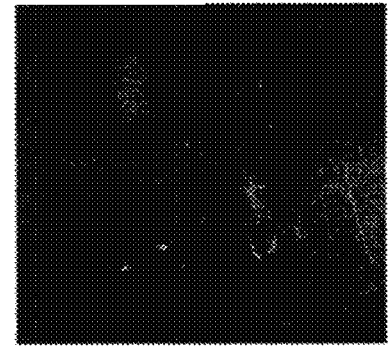

Example 11. Efficacy of Gel Formulations in Transferring Effective Concentrations of Active Ingredient to Larval Habitats This example demonstrates the efficacy of gel formulations of a composition comprising an active ingredient over particulate formulations of the composition comprising an active ingredient in transferring lethal concentrations of an active ingredient, such as a toxicant from females to water-holding containers (i.e., larval habitats) was tested in cage experiments. An autodissemination station equipped with a pyriproxyfen-treated transfer mesh (powder, gel or untreated) and 450 ml of oak leaf infusion water was centered in a cubic 2.2 m cage. A 360 ml capacity plastic cup was placed in each cage corner 15 cm from the walls. Each of the four cups was filled with 200 ml tap water and oviposition paper strips aligned as described above. Fifty gravid females were then introduced into the cage. After five days, the test was terminated, oviposition papers and eggs discarded, and containers were removed and the water assessed for pyriproxyfen transfer by larval bioassay (see 'insecticide bioassays' below). There were three treatment and one control cage per experiment and the experiment was repeated three times, providing a total of 36 test (that is, 36 powder and 36 gel) and 12 control ovicups for bioassay. Environmental conditions were 21-28° C., 60-75% RH, and a 16L:8D photoperiod. FIG. 8 shows a bar graph representation of percentage inhibition of emergence from autodissemination station with powder formulation I, powder formulation II, gel formulation I and gel formulation II, and a control. Bioassay: Larval bioassays were conducted in adult emergence units—450 ml plastic containers with a screen-covered lid and 200 ml of water (water lost via evaporation was replaced before assay). Each container held twenty 3rd instar *Aedes. albopictus*. Test containers were incubated at 26° C. and 16L:8D photoperiod. At 2-day intervals, ground rat chow (30 mg/L) was provided as food, water lost due to evaporation was replenished, dead and emerged individuals were removed, and successful adult emergence was recorded. Incomplete emergence or adults with attached exuviae were recorded as dead.

Larval bioassays were conducted in adult emergence units—450 ml plastic containers with a screen-covered lid and 200 ml of water (water lost via evaporation was replaced before assay). Each container held twenty 3rd instar *Aedes. albopictus*. Test containers were incubated at 26° C. and 16L:8D photoperiod. At 2-day intervals, ground rat chow (30 mg/L) was provided as food, water lost due to evaporation was replenished, dead and emerged individuals were removed, and successful adult emergence was recorded. Incomplete emergence or adults with attached exuviae were recorded as dead.

Example 12. Transfer of Gel formulation to Legs of Mosquitoes Visiting Autodissemination Station This example demonstrates the effective transfer of a gel formulation of a composition comprising an active ingredient to legs of mosquitoes visiting autodissemination stations. To detect gel transfer to the mosquito body parts when the gravid females exited the bamboo cut station, 1% UV-florescent dye was added to the formulation and mixed well. The gel then was applied to the window of the station via brush. Ten gravid females were then added to the station from the top opening and then the opening was covered with a plastic film. Gravid females were captured after they exited the station using a mosquito aspirator and frozen at −4 C. in a 14 ml centrifuge tube. The killed mosquitoes were observed under a compound microscope with regular light or UV light from. The UV light enabled the viewer to easily visualize gel adhering to mosquitoes. FIG. 9 shows pictures of mosquito legs under normal (FIG. 9A and FIG. 9C) and UV light (FIG. 9B and FIG. 9D) demonstrating effective transfer of gel formulation to legs of mosquitoes visiting autodissemination stations.

Example 13. Emulsifying Agent/Surfactants Results in Release of Gel into Aqueous Phase This example demonstrates that an emulsifying agent or surfactant results in release of the gel formulation of the composition into an aqueous body. The gel formulation of the composition comprising an active agent was again mixed with UV-florescent dye. A thin paper strip was dipped into the gel, thereby transferring formulation to the strip. The paper strip was then lightly touched to the water surface and visualized under a UV light. FIG. 10 shows before and after snapshots of a gel formulation being touched upon an aqueous surface demonstrating the effective and immediate release of the gel formulation to the aqueous phase and its subsequent dispersal.

Example 14. Effect of Gel Formulation on Pupal Mortality Rate

This example demonstrates that a gel formulation of the composition comprising an active ingredient is effective in maintaining a high mortality rate of up to at least about 80% inhibition of emergence, 48 hours after exposure. The percent inhibition of emergence was tested in cage experiments. An autodissemination station equipped with a pyriproxyfen-treated transfer mesh (powder, gel or untreated) and 450 ml of oak leaf infusion water was centered in a cubic 2.2 m cage. A 360 ml capacity plastic cup was placed in each cage corner 15 cm from the walls. Each of the four cups was filled with 200 ml tap water and oviposition paper strips aligned as described above. Fifty gravid females were then introduced into the cage. After five days, the test was terminated, oviposition papers and eggs discarded, and containers were removed. These females were then killed by freezing and placed individually in 450 ml plastic cups containing 200 ml of water and twenty 3rd instar Aedes albopictus. Test containers were incubated at 26° C. and 16L:8D photoperiod. At 2-day intervals, ground rat chow (30 mg/L) was provided as food, water lost due to evaporation was replenished, dead and emerged individuals were removed, and successful adult emergence was recorded. Incomplete emergence or adults with attached exuviae were recorded as dead. This experiment was repeated three times. FIG. 11 demonstrates that a gel formulation is resistant to removal of active ingredient by grooming behavior.

Example 15. Stability of a Gel Formulation

Physical stability of a gel formulation of a composition comprising an active ingredient prepared by the method of the present invention is assessed by measuring the initial viscosity and taking viscosity measurements over a period of six months with an interval of 1 week at different temperatures, such as 25° C., 37° C. and 45° C., using a commercial viscometer.

Example 16. Biphasic Dual Treatment Autodissemination Station Enhanced Transfer of Insect Growth Regulator to Mosquito Oviposition Sites After testing, the present inventors realized that the single pass ADS described in the prior examples possessed certain drawbacks. Accordingly, the improved bi-phase ADS was produced and tested. The present example describes the surprisingly superior results obtained with a biphasic treatment approach and apparatus suitable therefor which exhibits enhanced autodissemination efficacy. Significant improvements were observed which included, without limitation, increased contamination rate, improved formulation attachment and persistence of the larvacide. Widespread adoption of this novel technology should facilitate control of certain mosquitoes which is more targeted and less environmentally damaging than currently available methods.

Container mosquito *Aedes albopictus* (Skuse), an invasive species, has been reported to be a secondary vector responsible for several human diseases such as dengue, yellow fever and chikungunya (Gratz N G (2004) Med Vet Entomol; 18(3): 215-227. The mosquito is a tree-hole species that has adapted to urban containers generated by human activities (Raharimalala F N et al. (2012) Parasit Vectors; 5: 56). The cryptic larval habitat preferred by this species is difficult to reach by traditional pesticide spray and is the major reason of failure for the container mosquito control (Devine G J et al., (2009) Proc Natl Acad Sci; 106(28): 11530-11534. The gravid mosquito of *Ae. albopictus* possesses skip oviposition behavior and tends to distribute her eggs in different containers (Trexler J D et al., (1998) J Med Entomol; 35(6): 967-976). Scientists have been trying to use the gravid females as a vehicle to transfer insect growth regulator (IGR) into their larval habitat to kill mosquito larvae, an idea adapted from the insect biological control method with beneficial microbial agents (Itoh T, (1994) Trop Med; 36:243-248).

Pyriproxyfen, a juvenile hormone mimic, is highly toxic to the mosquito larvae, which disrupt the adult emergence from the pupa. The $LC_{50}$ of pyriproxyfen to *Ae. aegypti* and *Ae. albopictus* was reported to be as low as 0.012 ppb (Gaugler R. et al., (2012) Med Vet Entomol; 26(1): 37-45; Sihuincha M. et al. (2005). J Med Entomol; 42(4): 620-630). Since Itoh (1994) demonstrated that the pyriproxyfen can be transferred by gravid mosquito, *Ae. aegypti*, from a source point to their larval breeding habitat, different attempts have been made to utilize the concept and technology in combating container mosquitoes. Devine et al. (supra, 2009) achieved 42-98% emergence inhibition of *Ae. aegypti* adults in a field study at a public cemetery with pyriproxyfen dusted plastic containers. Caputo et al. (2012)) PLoS Negl Trop Dis; 6(8): e1793) obtained 40-70% mortality using modified sticky trap dusted with manually grained 5% pyriproxyfen powder in a warehouse field study. A novel autodissemination station has been developed by the present inventors and is described in the previous examples, using biodegradable materials, which possess good features such as low maintenance, environmental friendliness, low cost and auto refilling. However, there were some limitations that affected the ADS efficacy. 1. This station had wide openings that allow mosquitoes to enter and exit without being contaminated. 2. Contaminated mosquitoes could easily remove the powder formulation from their body parts since minimum amount of sticker oil (10%) could be added into the powder formulation due to caking problem. Due to these problems, the study achieved 82.5% pupal mortality of *Ae. albopictus* in their 31 $m^3$ room assay against 4 oviposition containers containing 200 ml water each, which indicated that improvements in formulation and ADS design are needed.

An effective ADS design should possess these criteria: 1. It should be more attractive than other containers in the same environment so that the gravid mosquitoes come to the ADS first before visiting others. 2. It should be effective in attaching the formulation to the insect body parts. 3. The formulations should resist mosquito cleaning behavior. 4. The formulation should be easy to release from mosquito body parts into the larval breeding site once the mosquitoes land on the water. Additional criteria such as longevity of efficacy and resistance to weather should be considered as well.

To improve the efficacy of previous ADS version, we designed a biphasic dual treatment system that maintained the good features or the previous version such as biodegradability and auto refilling. The core feature for this design was to direct the mosquitoes to exit from a designed path where they were treated with oil phase first and followed by the treatment of powder formulation, which improved the efficacy by increasing the contamination rate of mosquitoes, and a.i. load and persistence.

The following materials and methods are provided to facilitate the practice of Example 16.

ADS Design and Optimization

A biphasic autodissemination station (ADS) was developed to enhance attraction and contamination of gravid mosquitoes based on the previous version as described in the prior examples with modifications on the transfer chamber, which provided the attracted gravid mosquitoes a unidirectional path and biphasic formulations. The ADS consists of two main parts comprising of a water reservoir at the bottom [35] (adapted from previous version), above which was a transfer chamber [37] with a unidirectional cone [39] inserted in the transfer chamber (FIGS. 12, A & B). The reservoir could hold 600 mL water, which contains dried shredded oak leaves and other materials producing attractants to the gravid mosquitoes. There were overflow protection holes [40] located in the upper part of the reservoir as described in the previous examples. The transfer chamber was constructed with a cardboard mailing tube (101.5×155 mm; Office Depot, N.J. USA), a cotton mesh fabric [42] (39 openings/$cm^2$) secured within the chamber base by hot glue, a vertical fabric band [43] (20 mm width) glued on top portion inside the transfer chamber and a horizontal flat ring [44] (20 mm width) mounted on the top of the chamber (FIG. 12, B) to provide the base for powder band [46]. The cotton mesh functioned as a barrier to prevent mosquitoes from entering the reservoir. After a screening of seven fabric materials (Polyester fleece, Polyester fusible interfacing, Insul-Bright®, Worm Blend, Worm & Nature, Toner Grabber and Versi-DRY Lab Soakers), Versi-DRY lab soaker (Thermo Fisher Scientific, USA) was selected as liquid phase substrate band (2.5 cm width) carrying oil formulation [47] (corn oil: Tween 80=1: 1; 0.054 g/$cm^2$), and Insul-Bright® (Fabric Land, N.J.) was selected as the substrate material (2.5 cm width) for powder formulation (Esteem® 35 WP Insect Growth Regulator, 0.015 g/$cm^2$) mounted on top of the flat ring, which was constructed with plywood. Four spacers [48] (6+1 mm height, 10 mm D) created with wood blocks were fixed on top of each band with hot glue to maintain an accurate gap to allow mosquito to exit by walking and not by flying. The spacer size was determined by preliminary study in which the gap size allowed maximum contamination of mosquitoes and minimum number of mosquitoes trapped. The cup shape unidirectional cone consisted of a cup (mouth 9.5 cm, D; bottom 6.0 cm, D; height 8.0 cm), a cotton mesh fabric (39 openings/$cm^2$) fashioned into a shallow funnel and secured within the bottom of the cone, and an oil band [47] as described above surrounding the outside of the cup and a cover plate (FIG. 12, B, Unidirectional cone). The opening (10 mm D) at the bottom of the mesh funnel allows mosquito to enter the chamber. The cover plate [36] encircled unidirectional cone (plastic plate used in this prototype) was used to make an exit mechanism creating a slit (6±1 mm) between the cover plate and the top of the powder band. Cover plate was used to protect the powder band [46] from rain, and collect rainwater to refill the reservoir. After assembling of all parts, a fully functional station attracts gravid mosquitoes to enter from top opening into the chamber where females attempt to reach the water surface for oviposition. After failure in oviposition, mosquitoes exit the chamber by walking thru the oil band and get the tarsi treated with oil formulation that worked as sticker. Then, oil treated mosquitoes picked up the powder formulation by walking on the powder band before exiting the station for next subsequent oviposition site. ADS construction material was biodegradable and the station was paraffin wax coated to waterproof it and to extend its life. The unit was designed, however, to break down after a single mosquito season, which, for *Ae. albopictus* in New Jersey, amounts to approximately 4 months. The station's effective lifespan was proscribed by adjusting the thickness of the wall and wax coat. The station was dyed dark grey with ink. A prototype of a simpler version of the ADS was also constructed with the same materials with the consideration of easy manufacturing and formulation coating. The key feature and principle remain unchanged but the difference was that both oil band and powder band were mounted horizontally adjacent to each other on a wider horizontal plate of ring where the inner ring was coated with oil formulation and the outer ring was coated with powder formulation. A ridge just about the same height with the fabric materials was created with aluminum foil between the two bands to prevent from mixing (FIG. 12, C).

Mosquito Colony and Maintenance

*Aedes albopictus* larvae for bioassays were obtained from a colony established from eggs collected in Mercer County, N.J., U.S.A. in 2008 and supplemented during 2009 and 2010. The colony was maintained at 26±1° C., at a relative humidity (RH) of 75% under an LD 16:8 h photoperiod. Adults were held in 30×30×30 cm aluminum screen cages and supplied with 10% sucrose solution on cotton wicks *ad libitum*. Restrained guinea pigs were used to blood-feed females (Rutgers University Animal Use Protocol #86-129) and subsequent eggs were collected on seed germination paper and stored at 26±1° C. Eggs were hatched as needed by flooding egg papers and the larvae were held in enamel trays with 1 L of deionized water and 0.3 g of Brewer's yeast was provided every other day. Third instars were used in all bioassays.

Pyriproxyfen Activity Bioassay

Larval bioassays for pyriproxyfen were conducted in adult emergence units (450 ml plastic Deli containers lid on) under the standard laboratory conditions as described above under the heading, Mosquito colony and maintenance. Each container received twenty early 3$^{rd}$ instar *Ae. albopictus* in 200 ml sample water. Larvae were inoculated gently using dropper before placing the lid on. Five slots (4 cm each) were cut into the lid with a clean blade for aeration. Larval food (30 mg yeast/L) was provided twice a week which was freshly prepared every time. An additional lab control group was setup in triplicate using dichlorinated water. The bioassays were conducted in the sequence of lab control and treatment to minimize the chance of contamination. Water lost due to the evaporation during bioassay was replenished. Adult emergence and pupal mortality were accessed after there was no live lava or pupa in the water. Incomplete emergence or adult with attached exuvia was recorded as pupal death. If lab control had mortality higher than 20% in larval or pupal stages, results were discarded and the experiment was repeated. The experiments were conducted under environmental conditions of 26-28° C., 60-75% RH and LD 16:8 h.

ADS Attraction to Gravid Mosquito Assay

The new ADS prototype was tested for its attraction to *Ae. albopictus* gravid mosquitoes in a small cage (1.3×1.3×1.3 m) against the version described in the previous examples. The mosquito exit openings of the new prototype were blocked by removing all spacers to trap the mosquitoes entering the chamber. The previous version was modified by inserting a chamber with unidirectional funnel between the tri-arm transfer chamber (original transfer mesh was removed) and reservoir to trap the attracted mosquitoes. Twenty gravid females were release into the cage for 24 h and number of mosquitoes in each station was counted. The experiment was repeated 3 times with 3 replicates in each experiment.

Attachment and Persistence of IGR Formulations Assay

To test the formulation attachment and persistence over time, fifteen gravid females were allowed to exit from the ADS as described above into a cage (50×50×50 cm) and 3 of them were taken with an aspirator at each time interval (0, 2, 4, 8 and 24 h). Each of the 3 mosquitoes was released into a Deli cup (450 mL) containing 250 mL of water with lid on. To make sure the formulation on the mosquito body was fully released into the water, gently shook the container so that the mosquito was touching the water surface. The mosquito then was removed with a dropper and 50 mL of the water sample was withdrawn from the cup for residue analysis. The samples for residue analysis were stored in a brown glass bottle at −20° C., and shipped to Golden Pacific Laboratories (California, USA) in thermal box packed with dry ice for residue analysis at the end of the assay. The rest of the 200 mL water in the container was used for bioassay as described above. The above experiment was repeated twice and the control group used dechlorinated water.

Room Assay

The test area was scaled up to a larger room (31 m$^3$) measuring 2.1 m in width, 5.7 m in length and 2.6 m in height. A station was placed in the center of the room and 10 Deli cups (450 mL, black painted from outside) containing 250 ml water were positioned 30 cm from the walls along each side of the room. Fifty gravid females were introduced for a 5-day test. The experiment was conducted under environmental conditions of 26-28° C., 60-75% RH and LD 16:8 h. The cups then were tested for pyriproxyfen activity using larval bioassay as described above. Ten additional untreated cups were included as controls. The pupal mortality in the room trials was analyzed against their respective controls with a t-test (P≤0.05).

Green House Assay

Green house with 2 bays (8×5×2.5 m each) was used for the semi-field assay. One ADS was positioned in the center of each bay and 6 Deli cups (450 mL, black painted from outside) containing 250 mL water each were setup as shown in FIG. 5 and 10% sugar solution was provided in a plastic cup with cotton wick. In each bay, 100 gravid mosquitoes (2 days post blood feeding) were released after the setup of ADS and oviposition containers. The containers were collected and sent for lab bioassay as described above after the 5 day experiment. The percent contamination of oviposition sites was accessed by calculating the percentage of the containers contaminated with pyriproxyfen after the bioassay. The temperature of 22-30° C. and relative humidity of 45-70% were recorded during the experiment. The photoperiod was controlled as LD 16:8 h.

Efficacy of pyriproxyfen was expressed as mean + standard error % of pupal mortality, which was corrected with control using Abbott's formula (Abbott W. S. (1925) J Econ Entomol; 18: 265-267). If any control had higher than 20% mortality in any stage, data were discarded and experiment was repeated. The pupal mortality from treatment group was compared with control using T-test at the significant level of p<0.05.

Attraction to Gravid Mosquitoes

The biphasic ADS showed significantly higher attraction (73.28+16.47%) than the one phase version described in the previous example, (26.72+6.92%) among the 64+14.5% trapped gravid mosquitoes in a small cage competing test. The result indicated that the open cup shaped ADS was more attractive than the previous tri-arm design Attachment and Persistence of IGR Formulation Residue analysis data clearly indicate that each individual gravid female of *Ae. albopictus* carried 0.08+0.02 µg pyriproxyfen right after exiting from the bi-phase dual treatment ADS. Although the amount of the chemical a.i. decreased over time, each gravid mosquito still carried 0.03+0.01 µg pyriproxyfen after 24 h post-treatment, which is sufficient to kill 100% of the larvae in a container filled with 250 ml of water (FIG. 13, A). The bioassay result confirmed the above finding, where 100% of emergence inhibition was achieved up to 8 h post exposure and 96+1.7% mortality was observed 24 h post exposure (FIG. 13, B).

Room Assay

The ADS achieved 100% pupal mortality in each of the 10 oviposition cups in a room of 31.1 m$^3$ where 50 gravid mosquitoes were allowed to oviposit for 5 days (FIG. 14). Footprints of gravid mosquitoes were visualized with UV light from some of the containers, which indicated physical transfer of pyriproxyfen a.i. (FIG. 15). The second prototype described in 2.1 was also tested in this big room assay. The same 100% pupal mortality was achieved in each of the 10 oviposition cups, which indicated that this design performed the same efficacy but possessed advantage of easier manufacturing.

Greenhouse Assay

Average of 57.1+11.4% pupal mortality was achieved by each ADS against 6 oviposition containers in a greenhouse assay in each bay (100 m$^3$) despite drag of cups with low mortality (0-30%) located in the area (the bottom side of FIG. 16) with high disturbance of human activities and unfavorable conditions (low RH and less shady). Interestingly, the pyriproxyfen had been transferred to 91.7% of the containers tested although some containers achieved as low as 10-30% pupal mortality.

Discussion

The bi-phase dual treatment design maintained the advantages of the previous version such as low maintenance, biodegradability, and auto refilling features, and greatly improved upon this design by resolving the problems of passive treatment, low attraction, poor attachment and poor persistence. This weather-proof design, with its high efficacy, possesses advantages over the devices developed and tested for the same purposes by other researchers. The success of the dual phase ADS is attributed to 3 key features: attraction, attachment, and persistence.

The open cup shaped design made this ADS more attractive to gravid mosquitoes than the previous design with side openings. While oak leaf attractant was used in these assays, other attractants could be employed. However, it has been demonstrated that the gravid females of *Ae. albopictus* showed preferences to certain chemical cues associated with different plant leaf infusions and bacterial activities (Ponnusamy L. et al., (2010) J Chem Ecol; 36(7): 709-719; Ponnusamy L. et al., (2008) Proc Natl Acad Sci USA; 105(27): 9262-9267). The plant-derived chemical cue, oviposition pheromone, luring gravid mosquitoes of *Culex* species has been described and synthesized (Olagbemiro T. O. et al., (2004) J Chem Ecol; 30(5): 965-976; Das S. et al., (2012) Carbohydr Res; 358:7-11). The chemical n-heneicosane extracted from conspecific larval conditioned water also showed activity for attracting gravid mosquitoes of *Ae. Aegypti* (Mendki, M. J. G. et al. (2000) Curr Sci; 78(11): 1295-1296).

Significantly improved attachment and persistence were achieved by directing the attracted gravid mosquitoes to walk thru bi-phasic dual treatment system where the mosquitoes were treated with oil formulation first to maximize the sticker load. This resolved the problem of the previous version that only 10% of oil sticker could be applied to the powder formulation due to caking. With 0% of a.i. in the oil formulation and 35% a.i. in the powder formulation, we have quantified the amount of a.i. carried by each individual gravid mosquito of *Ae. albopictus* using GC/MS with the confirmation of bioassay. We have detected as much as 0.10 and 0.04 µg of a.i. from a single mosquito zero and 24 h post-exit from the ADS, respectively. The amount of a.i. carried by a mosquito is enough to kill 100% of the larvae in a container with 250 ml water. Moreover, the efficacy can be further improved by increasing the concentration of a.i. in the powder formulation and adding a.i. to the oil formulation. We have recently shown that with newly developed formulations, a.i. can be increased up to 20% and 60% in the oil and powder formulations, respectively, without altering the attaching and unloading behavior of the formulations. The second advantage is that gravid mosquitoes treated with high concentration of pyriproxyfen in oil formulation will live significantly shorter lives than will untreated mosquitoes and thereby reduce the chance for disease transmission.

With this new and improved ADS, we have achieved 100% pupal mortality in the big room assay against 10 oviposition sites, demonstrating significantly higher efficacy than the uniphase version that produced only 81% pupal mortality against 4 containers. While the maximum number of containers one ADS can contaminate with 50 gravid females was not tested in the present example, our current serial transfer study showed that one individual gravid female was able to contaminate at least 3 containers with 100% mortality right after it exited the ADS, which is indicative of successful serial transfer.

In our greenhouse study, we achieved an average of 57.1% pupal mortality against 6 containers with one ADS. The efficacy was lower than big room assay. The Greenhouse we used in this study was more complex where plants covered about 50% of the area tested. Mosquitoes may have had more opportunities to unload the formulations by resting anywhere with high humidity or water droplets from watering the plants. However, cups with lower or no pupal mortality such as the 2 cups on the bottom of Bay 2 (FIG. 16) were located in the south side of the greenhouse where there was bright sunlight during day time, lower humidity all day and night due to the heating system mounted on the wall. The other factor affecting the performance of these cups was the disturbance of human activities while maintaining the plant such as watering. These cups were located in the habitat unfavorable to gravid mosquitoes since the mosquitoes prefer shaded areas with high humidity for resting and oviposition. Our field study shown that the pyriproxyfen can be transferred as far as 200 m distance and produced 100% pupal mortality in a container with 250 ml water. In a different field study conducted the same year (2012), more than 60% of the containers were contaminated with variable pupal mortality.

The bi-phase ADS with both oil and powder bands mounted on a single plate is easier to construct when compared to the ADS of the previous examples. The plate feature facilates coating with the oil and powder formulations. Moreover, the plates can be modified into a reloadable cartridge for a reusable station.

Pyriproxyfen is highly toxic to certain species of insect pest but extremely safe for mammals. Using this chemical for autodissemination against other insect pests, such as house flies, other than mosquitoes has also been attempted with promising results. However, as size, behavior and breeding habitat varies among different insect species, modifications on ADS, attractants and formulations are needed to suite different pests.

In conclusion, dual treatment in biphasic ADS system, a novel technology, enhanced the autodissemination efficacy by forcing the visiting mosquitoes to be treated with sticker oil formulation first and then attached the powder formulation upon exiting and therefore increased the contamination rate, enhanced the IGR attachment and improved the persistence. The device has achieved superior results in room and semi field assays. This technology will fully utilize the high and largely untapped potential of a relatively new insecticide, providing the public health and vector control fields with a new tool that is more effective and less environmentally damaging than currently available methods. The expansion of the technology will advance the pest management with reduced and more targeted pesticide application in combating disease vectors as well as other insect pests such as house flies, whose breeding habitats are cryptic and difficult to reach by conventional pesticide spray.

Example 17

We were able to improve upon the ADS station described in the previous examples. During field applications, certain issues were encountered, including for example, blockage of the opening with falling leaves or spider webs, short lasting attraction to gravid mosquitoes, low tolerance to high temperature and difficulties in powder formulation coating and packing. Accordingly, the present Example provides a new design and improved associated components which resolve these issues.

Infusion Reservoir

A key feature of our new design is a larger unidirectional funnel (56) that allows any falling leaves to come through the exterior opening (53) at the top instead of blocking it. To facilitate leaf containment, the water reservoir (51) was designed as a circular tank (55) with a hollow cylindrical center (57) (FIG. 17, Reservoir). Leaves fall in from the top opening (53) all the way to the bottom as shown in blue line labeled Leaf path (61). The depth of the leaf chamber (63) should be sufficient to capture falling leaves throughout the season. The device can also be relocated and the accumulated leaves which pass through the hollow center (57) can be left at the original location if necessary. Mosquito path (65) (red line) also includes entry through the top opening (53) lured by the attractant. The mosquito will go up and end up exiting the gap (78) in the transfer plate (73) formed between the formulation ring (79) and the transfer plate cover (73), the insect growth regulator in the form of gel formulation (75) being embedded in the formulation ring (79) to contaminate the exiting mosquitoes before they leave the station.

This new design has been tested for mosquito attraction against the ADS of the prior examples. Results indicated that the new design attracted 4 times as many mosquitoes as the previous version (FIG. 18). Our data also indicated that mosquitoes entering the device go up trying to exit from top. FIG. 19 showed that the mosquitoes got trapped on the top of the transfer chamber (69) trying to exit from top through the exit gap (78). This design itself can be used together with sticky paper (77) for mosquito surveillance and control.

Transfer Plate

Another improved feature is the transfer plate (71). The improved transfer plate contains a transfer plate cover (73) and a formulation ring (79) which is filled with gel formulation (75) comprising insect growth regulator as shown in FIG. 20. The formulation ring (79) is as narrow as 5 mm which allows exiting mosquitoes to come across with minimum of effort. Only one gel formulation (75) was used which contains 40% of a.i. Sealed position is for packing, shipping and shelf storage. Open position is in active status in the field. The gap size varies according to the mosquito species, (body size), which is adjustable by rotating the cover along the threads. FIG. 20 shows the transfer plate (71) in the closed and open position—without and with an exit gap (78) respectively.

The transfer plate (71) was tested for contamination with 15 mosquitoes introduced into the transfer chamber (69) and allowed to exit through the exit gap (78) of the transfer plate (71). Formulation was embedded with 0.1% of oil based florescent dye and legs and body contamination was evaluated under UV light. The result showed that there was no significant difference from the previous dual treatment ADS (FIG. 21).

Formulation

Gel formulation was specifically developed for this purpose, which contains 40% pyriproxyfen as a.i, 36% methylated seed oil and 14% fumed silica as carrier, 4% of polysorbete-20 and 6% of Sodium Dodecyl Sulfate as emulsifier. The formulation appears stable under extreme field weather conditions such as high humidity and high or low temperature. Components of the formulations can be varied slightly as set forth below.

| Formulation # | % Silicon | % a.i | % Tween 20 | % Meth oil |
| --- | --- | --- | --- | --- |
| 1 | 10 | 18 | 7.2 | 64.8 |
| 2 | 6 | 18.8 | 7.52 | 67.68 |
| 3 | 5 | 19 | 7.6 | 68.4 |
| 4 | 0 | 20 | 8 | 72 |
| 5 | 10 | 13.5 | 7.2 | 69.3 |
| 6 | 6 | 14.1 | 7.52 | 72.38 |
| 7 | 5 | 14.25 | 7.6 | 73.15 |
| 8 | 0 | 15 | 8 | 77 |

Infusion Pouch

We also significantly improved the attractant for use in the ADS. Conventional oak leaf infusion typically works for about 2 weeks on container mosquitoes such as *Aedes albopictus*. Infusion attractivity to the mosquito peaks after one week preparation and deteriorates quickly thereafter. After two weeks, very little attractant remains. Although we have developed a better recipe (15 gm oak leaves, 30 gm oak wood and 1 L water) which shows significantly higher attraction to container mosquito gravid females, the attraction to these mosquitoes lasted for only 2 to 4 weeks. To extend the attraction for a season, we have developed a pouch (85) containing the same recipe in a porous fabric bag and a cotton wick (87). The infusion pouch (85) hangs above the water in the reservoir (51), such as on a platform (89) with a wick (87) in contact with the water to keep the pouch (85) moisturized but not completely soaked (FIG. 22). The attraction to *Aedes albopictus* was tested over time with plain water and one week old infusion of the same recipe described above. The results showed that the pouch (85) was more attractive up to week 5 in comparison with one week old infusion. While some deterioration was observed, attractivity was still comparable with one week old infusion up to week 10 (FIG. 23), thereby providing the lure function for the ADS throughout the whole season.

EQUIVALENTS

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. An apparatus for autodissemination, the apparatus comprising:
    (a) a reservoir housed within a circular tank, said circular tank reservoir having a hollow cylindrical center;
    (b) a wide mouth unidirectional funnel having a top and a bottom inserted within said hollow cylindrical center, said wide mouth unidirectional funnel being wide enough to permit leaf passage into said hollow cylindrical center through an exterior opening of said wide mouth unidirectional funnel;
    (c) a mesh cover over said reservoir, said mesh cover encircling the hollow cylindrical center and preventing insects from entering said reservoir;
    (d) a transfer plate having a formulation ring;
    (e) a transfer plate cover arranged over said formulation ring to provide an exit gap between said transfer plate cover and said formulation ring, said formulation ring of said transfer plate having an insect population controlling active ingredient affixed thereto in a gel formulation suitable for transfer to any insect passing through said exit gap,
wherein the top of the wide mouth unidirectional funnel, the transfer plate, the transfer plate cover, and a top rim of the circular tank share a common axis, and said exit gap is formed by including spacers between said transfer plate and said transfer plate cover.

2. The apparatus according to claim 1, wherein at least one of the reservoir, the unidirectional funnel, the mesh cover, the transfer plate, or the transfer plate cover is a molded biodegradable material.

3. The apparatus according to claim 2, further comprising a water-proofing agent.

4. The apparatus of claim 3, wherein said water proofing agent is paraffin wax.

5. The apparatus of claim 2, wherein the biodegradable material is selected from the group consisting of wet shredded cardboard, a pasteboard, a cellulose-based material, and combinations thereof; and a binder, wherein the binder is a binder selected from the group consisting of a corn starch, peat moss, an egg carton, rice hulls, a newspaper, straw, a natural polymer(s), and combinations thereof.

6. The apparatus of claim 1, wherein said reservoir comprises water below said mesh cover, said reservoir further comprising an infusion pouch hanging above said water with a wick in contact with said water, thereby keeping said infusion pouch moisturized, wherein said infusion pouch comprises an attractant containing 15 gm oak leaves, 30 gm oak wood or pheromones.

7. The apparatus of claim 6, wherein said infusion pouch hangs above said water on a platform.

8. The apparatus of claim 1, wherein said exit gap is 4 mm.

9. The apparatus of claim 1, wherein said exit gap is 5 mm.

10. The apparatus of claim 1, wherein said insect population controlling active ingredient in said gel formulation comprises an insecticide.

11. The apparatus of claim 10, wherein said gel formulation further comprises at least one carrier, at least one sticking agent and at least one emulsifying agent.

12. The apparatus of claim 10, wherein said insecticide is selected from the group consisting of an insect growth regulator, an organophosphate, a carbamate, a chlorinated diphenyl alkane, a cyclodiene, a rotenoid, an organic fluoride compound, a nicotinoid, a hexachlorocyclohexane, and a combination thereof.

13. The apparatus of 1, wherein said gel formulation comprises five components, pyriproxyfen, methylated seed oil, fumed silica, polysorbate-20 and Sodium Dodecyl Sulfate, said formulation being stable under extreme field weather conditions.

14. The apparatus of claim 13, wherein said gel formulation comprises the following four components of the five components comprising fumed silica which is Silicon, pyriproxyfen, polysorbate-20 which is Tween 20, and methylated seed oil which is Meth oil, the following four components comprising in combination at percentages selected from the group consisting of:

| % Silicon | % pyriproxyfen | % Tween 20 | % Meth oil |
|---|---|---|---|
| 10 | 18 | 7.2 | 64.8 |
| 6 | 18.8 | 7.52 | 67.68 |
| 5 | 19 | 7.6 | 68.4 |
| 0 | 20 | 8 | 72 |
| 10 | 13.5 | 7.2 | 69.3 |
| 6 | 14.1 | 7.52 | 72.38 |
| 5 | 14.25 | 7.6 | 73.15 |
| 0 | 15 | 8 | 77. |

15. A method for autodisseminating an insect population controlling active ingredient for control of insect populations comprising dispersing one or more apparatus of claim 1 in an area where control of insect populations is desirable.

16. The method of claim 15, wherein said insect population controlling active ingredient is an insect growth control regulator.

17. The method of claim 16, wherein said regulator is pyriproxyfen.

18. The method of claim 15, wherein said insect population controlling active ingredient is an insect pathogen.

19. The method of claim 18, wherein said pathogen is selected from the group consisting of a fungi, bacteria, and virus.

* * * * *